(12) United States Patent
Leturcq et al.

(10) Patent No.: US 9,222,070 B2
(45) Date of Patent: Dec. 29, 2015

(54) CELL THERAPY METHOD FOR THE TREATMENT OF TUMORS

(75) Inventors: Didier J. Leturcq, San Diego, CA (US); Ann M. Moriarty, Poway, CA (US); Michael R. Jackson, Del Mar, CA (US); Per A. Peterson, Basking Ridge, NJ (US); Jon M. Richards, Glenview, IL (US)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 499 days.

(21) Appl. No.: 11/782,264

(22) Filed: Jul. 24, 2007

(65) Prior Publication Data

US 2009/0004142 A1 Jan. 1, 2009

Related U.S. Application Data

(63) Continuation of application No. 10/289,566, filed on Nov. 7, 2002, now abandoned, which is a continuation-in-part of application No. 10/080,013, filed on Feb. 19, 2002, now abandoned.

(60) Provisional application No. 60/270,252, filed on Feb. 20, 2001.

(51) Int. Cl.
| | |
|---|---|
| C12N 5/071 | (2010.01) |
| C12N 5/0783 | (2010.01) |
| A61K 48/00 | (2006.01) |
| A61K 38/20 | (2006.01) |
| A61K 38/21 | (2006.01) |
| A61K 39/00 | (2006.01) |
| A61K 41/00 | (2006.01) |
| C12N 5/07 | (2010.01) |
| A61K 35/12 | (2015.01) |

(52) U.S. Cl.
CPC .......... *C12N 5/0636* (2013.01); *A61K 38/2013* (2013.01); *A61K 38/212* (2013.01); *A61K 39/0011* (2013.01); *A61K 41/00* (2013.01); *A61K 48/00* (2013.01); *C12N 5/0601* (2013.01); *A61K 2035/124* (2013.01); *A61K 2039/5154* (2013.01); *A61K 2039/5156* (2013.01); *A61K 2039/5158* (2013.01); *A61K 2039/55527* (2013.01); *A61K 2039/55533* (2013.01); *A61K 2039/55538* (2013.01); *C12N 2501/23* (2013.01); *C12N 2501/515* (2013.01); *C12N 2502/99* (2013.01); *C12N 2510/00* (2013.01)

(58) Field of Classification Search
USPC .......... 424/93.1, 93.2, 93.21, 277.1; 530/300; 435/373, 372.3
See application file for complete search history.

(56) References Cited

U.S. PATENT DOCUMENTS

| | | |
|---|---|---|
| 4,401,756 A | 8/1983 | Gillis |
| 4,407,945 A | 10/1983 | Gillis |
| 4,473,642 A | 9/1984 | Gillis |
| 4,530,901 A | 7/1985 | Weissmann |
| 4,695,623 A | 9/1987 | Stabinsky |
| 4,897,471 A | 1/1990 | Stabinsky |
| 4,992,367 A | 2/1991 | Cullen |
| 5,314,813 A | 5/1994 | Peterson et al. |
| 5,397,703 A | 3/1995 | De Boer et al. |
| 5,487,974 A | 1/1996 | Boon-Falleur et al. |
| 5,529,921 A | 6/1996 | Peterson et al. |
| 5,583,031 A | 12/1996 | Stern |
| 5,585,461 A | 12/1996 | Townsend et al. |
| 5,587,289 A | 12/1996 | Lurquin et al. |
| 5,637,483 A | 6/1997 | Dranoff et al. |
| 5,645,837 A | 7/1997 | Jameson et al. |
| 5,662,907 A | 9/1997 | Kubo et al. |
| 5,759,783 A | 6/1998 | Lurquin et al. |
| 5,820,866 A | 10/1998 | Kappler et al. |
| 5,827,642 A | 10/1998 | Riddell et al. |
| 5,827,737 A | 10/1998 | Peterson et al. |
| 5,843,648 A | 12/1998 | Robbins et al. |

(Continued)

FOREIGN PATENT DOCUMENTS

| | | |
|---|---|---|
| CA | 2069541 | 11/1993 |
| EP | 0814838 | 5/2003 |

(Continued)

OTHER PUBLICATIONS

Lollini et al. (Curr. Cancer Drug Targets. May 2005; 5 (3): 221-228).*

(Continued)

*Primary Examiner* — Stephen Rawlings
(74) *Attorney, Agent, or Firm* — Myra H. McCormack

(57) ABSTRACT

T cell responses are often diminished in humans with a compromised immune system. We have developed a method to isolate, stimulate and expand naïve cytotoxic T lymphocyte precursors (CTLp) to antigen-specific effectors, capable of lysing tumor cells in vivo. This ex vivo protocol produces fully functional effectors. Artificial antigen presenting cells (AAPCs; *Drosophila melanogaster*) transfected with human HLA class I and defined accessory molecules, are used to stimulate CD8+ T cells from both normal donors and cancer patients. The class I molecules expressed to a high density on the surface of the *Drosophila* cells are empty, allowing for efficient loading of multiple peptides that results in the generation of polyclonal responses recognizing tumor cells endogenously expressing the specific peptides. The responses generated are robust, antigen-specific and reproducible if the peptide epitope is a defined immunogen. This artificial antigen expression system can be adapted to treat most cancers in a significant majority of the population.

8 Claims, 35 Drawing Sheets

(56) References Cited

U.S. PATENT DOCUMENTS

| | | | |
|---|---|---|---|
| 5,844,075 | A | 12/1998 | Kawakami et al. |
| 5,874,560 | A | 2/1999 | Kawakami et al. |
| 5,994,523 | A | 11/1999 | Kawakami et al. |
| 6,075,122 | A | 6/2000 | Cheever et al. |
| 6,140,050 | A | 10/2000 | Sahin et al. |
| 6,355,479 | B1 | 3/2002 | Webb et al. |
| 2006/0234310 | A1 | 10/2006 | Cai et al. |

FOREIGN PATENT DOCUMENTS

| | | |
|---|---|---|
| JP | 2001-89389 | 4/2001 |
| WO | WO 97/32970 | 2/1992 |
| WO | WO 93/17095 | 9/1993 |
| WO | WO 95/34817 | 12/1995 |
| WO | WO 96/05287 | 2/1996 |
| WO | WO 96/06929 A2 | 3/1996 |
| WO | WO 96/27392 | 9/1996 |
| WO | WO 96/34015 A1 | 10/1996 |
| WO | WO 97/10002 | 3/1997 |
| WO | WO 92/01459 | 9/1997 |
| WO | WO 99/37313 A1 | 7/1999 |
| WO | WO 99/54345 | 10/1999 |
| WO | WO 00/25722 | 5/2000 |
| WO | WO 01/57068 A1 | 8/2001 |
| WO | WO 01/59073 A2 | 8/2001 |
| WO | WO 02/04603 A2 | 1/2002 |
| WO | WO 02/065992 | 8/2002 |

OTHER PUBLICATIONS

Lollini et al. (Trends Immunol. Feb. 2003; 24 (2): 62-66).*
Bins et al. (J. Immunother. Feb.-Mar. 2007; 30 (2): 234-239).*
Rosenberg et al. (J. Immunol. 2005; 175: 6169-6176).*
Harlin et al. (Cancer Immunol. Immunother. 2006; 55: 1185-1197).*
Mortarini et al. (Cancer Res. May 15, 2003; 63: 2535-2545).*
Wang et al. (Exp. Opin. Biol. Ther. 2001; 1 (2): 277-290).*
Bodey et al. (Anticancer Research. 2000; 20: 2665-2676).*
Cox et al. (Science. 1994; 264: 716-719).*
Ezzell (Journal of NIH Research. 1995; 7: 46-49).*
Spitler (Cancer Biotherapy. 1995; 10: 1-3).*
Mellman (The Scientist. 2006; 20 (1): 47; published on the Internet; pp. 1-8).*
Lee et al. (Journal of Immunology. 1999; 163: 6292-6300).*
Zaks et al. (Cancer Research. 1998; 58: 4902-4908).*
Gao et al. (Journal of Immunotherapy. 2000; 23: 643-653).*
Bocchia et al. (Haematologica. 2000; 85; 1172-1206).*
Gura (Science. 1997; 278: 1041-1042).*
Lens (Expert Opin. Biol. Ther. Mar. 2008; 8 (3): 315-323).*
Xia et al. (Cell. Res. Mar. 2006; 16 (3): 241-259).*
Schietinger et al. (Semin. Immunol. Oct. 2008; 20 (5): 276-85).*
Prehn (Cancer Cell Int. Aug. 1, 2005; 5 (1): 25; pp. 1-5).*
Morris et al. (Surg. Oncol. Clin. N. Am. Oct. 2007; 16 (4): 819-831).*
Finke et al. (Immunol. Today. Apr. 1999; 20 (4):158-160).*
Albert et al., "Dendritic Cells Acquire Antigen from Apoptotic Cells and Induce Class I-Restricted CTLs", Nature, 1998, 392: pp. 86-89.
Alderson, M.R., et al. "Interleukin 7 Enhances Cytolytic T Lymphocyte Generation and Induces Lymphokine-activated Killer Cells from Human Peripheral Blood", 1990. J. Exp. Med. vol. 172:577-587.
Alters, et. al, Immunotherapy of cancer: Generation of CEA specific CTL using CEA peptide pulsed dendritic cells, Dendritic cells in Fundamental and Clinical Immunology (excerpt from book), 1997, 417, 519-524.
Altman et al, "Phenotypic Analysis of Antigen-Specific T Lymphocytes", Science, vol. 274, Oct. 4, 1996, pp. 94-97.
Angelichio et al, "Comparison of Several Promoters and Polyadenylation Signals for Use in Heterologous Gene Expression in Cultured *Drosophilia* Cells", Nuc. Acids Res., vol. 19, No. 18, pp. 5037-5043, 1991.
Baxevanis et al, "Tumor-Specific CD4+ T Lymphocytes from Cancer Patients are Required for Optimal Induction of Cytotoxic T Cells against the Autologous Tumor," J. Immun. (2000) 164:3902-3912.
Bellone et al, "In Vitro Priming of Cytotoxic T Lymphocytes against Poorly Immunogenic Epitopes by Engineered antigen-presenting Cells", Eur. J. Immunology 24: 2691-2698, 1994.
Bhardwaj et al., IL-12 in Conjunction with Dendritic Cells Enhances Antiviral CD8+CTL Responses in Vitro, J. of Clinical Investigation, vol. 98, No. 3, Aug. 1996, pp. 715-722.
Boog et al, "Specific Immune Responses Restored by Alteration in Carbohydrate Chains of Surface Molecules on Antigen-Presenting Cells", Eur. J. Immunol. 1989. 19:537-542.
Brown, J.P. et al, Protein Antigens of Normal and Malignant Human Cells Identified by Immunoprecipitation with Monoclonal Antibodies, 1980 Issue of Jun. 10, J. of Biological Chemistry, vol. 255, No. 11: 4980-4983.
Burshtyn et al., "High Occupancy Binding of Antigenic Peptides to Purified, Immuno-adsorbed H-2Db$\beta$2 m Molecules", J. of Immunol. vol. 151, 3070-3081, No. 6, Sep. 15, 1993.
Celis E., et al, Induction of Anti-tumor Cytotoxic T Lymphocytes in Normal Humans Using Primary Cultures and Synthetic Peptide Epitopes, PNA, vol. 91, pp. 2105-2109.
Cai et al "Probing the activation requirements for naïve CD8 + T cells with *Drosophilia* cell transfectants an antigen presenting cells," Immunological Reviews, 1998, 165: 249-265.
Cai et al., Requirements for Peptide-Induced T Cell Receptor Down-regulation on Naïve CD8 + T Cells., J. Exp. Med, vol. 185, No. 4, Feb. 17, 1997 pp. 641-651.
Cai, et al, "Influence of Antigen Dose and Costimulation on the Primary Response of CD8 + T Cells in Vitro," J. Exp. Med. 1996, 183, 2247-2257.
Chen et al., "Costimulation of T Cells for Tumor Immunity", Imm. Today vol. 14, No. 10:1993 pp. 483-485.
Chikamatsu et al, "Generation of Anti-p53 Cytotoxic T Lymphocytes from Human Peripheral Blood Using Autologous Dendritic Cells", Clinical Cancer Res, vol. 5 1281-1288, Jun. 1999.
Corr, M. et al, "T Cell Receptor-MHC Class I Peptide Interactions: Affinity, Kinetics, and Specificity", Science, vol. 265, Aug. 12, 1994, pp. 946-949.
Darrow, T.L. et al., "The role of HLA class I antigens in recoginition of melanoma cells by tumor-specific cytotoxic T lymphocytes", Journal of Immunology, 1989, vol. 142, 3329-3335.
De Bruijn et al., "Peptide Loading of Empty Major Histocompatibility Complex Molecules on RMA-S Cells Allows the Induction of Primary Cytotoxic T Lymphocyte Responses", Eur. J. Immunol. 1991, 21: 2963-2970.
De Wall Malefyt et al., "CD2/LFA-3 or LFA-1/1CAM-1 but not CD28/B7 Interactions can Augment Cytotoxicity by Virus-Specific CD8+ Cytotoxic T Lymphocytes", Eur. J. Immunol. 1993, 23: 418-424.
Gagliardi, et al, "Presentation of Peptides by Cultured Monocytes or Activated T Cells Allows Specific Priming of Human Cytotoxic T Lymphocytes in Vitro", Int. Immunol. vol. 7, No. 11, pp. 1741-1752. (1995).
Germain, "MHC-Dependent Antigen Processing and Peptide Presentation: Providing Ligands for T Lymphocyte Activation", Cell, vol. 76, 287-299, Jan. 28, 1994.
Goldstein et al, Cytotoxic T cell activation by class I protein on cell-size artificial membranes: antigen density and LYT-2/3 function, Journal of Immunology 138(7):2034-2043 1987.
Godeau, F.,et al, "Expression of a mouse class I MHC molecule in insect cells using a baculovirus vector", Journal of Cell Biology, 1079( ): Abstract # 2092, 1988.
Godeau, F., et al., "Expression and Characterization of Recombinant Mouse $\beta$2-Microglobulin Type A in Insect Cells Infected with Recombinant Baculoviruses", Res. Immunol. 142, 409-416, 1991.
Godeau, F., et al., "Purification and Ligand Binding of a Soluble Class I Major Histocompatibility Complex Molecule Consisting of the First Three Domains of H-2Kd Fused to $\beta$2-Microglobulin Expressed in the Baculovirus-Insect Cell System", J. of Biological Chem., vol. 267, No. 34, Dec. 5, 1992 pp. 24223-24229.
Ho et al, "Adoptive therapy with CD8+ T cells: it may get by with a little help from its friends", Journal of Clinical Investigation (2002) 110(10): 1415-1417.

(56) References Cited

OTHER PUBLICATIONS

Hom, Sophia et al, "Common expression of melanoma tumor-associated antigens recognized by human tumor infiltrating lymphocytes: Analysis by Human Lymphocyte antigen Restriction", Journal of Immunol. 10:153-164, 1991.
Hortsch M., et al, "Sticky molecules in not-so sticky cells", TIBS 16—Aug. 1991, pp. 283-287.
Huang,et al, "TCR-mediated internalization of peptide-MHC complexes acquired by T cells," Science, Oct. 1999, 286(5441), 952-954.
Ioannides Constantin et al, "T-Cell recognition of oncogene products: A new strategy for Immunotherapy", Molecular Carcinogenesis; 6:77-82 (1992).
Jackson et al, Empty and peptide-containing conformers of class I major histocompatibility complex molecules expressed in *Drosophila melanogaster* cells, Proceedings of the National Academy of Sciences USA 89:12117-12121 1992.
Kawakami, Y. et al, "T-cell recognition of human melanoma antigens", Journal of Immunology. 14:88-93, 1993.
Kluger, Harriet, et al., "Her2/neu is not a commonly expressed therapeutic target in melanoma—a large cohort tissue microarray study", Melanoma Research 2004, 14:207-210.
Lanzavecchia, A., "License to Kill", Nature 1998, 393:413.
Levy et al., "Co-expression of the Human HLA-B27 Class I Antigen and the E3/19K Protein of Adenovirus-2 in Insect Cells using a Baculovirus Vector", Int. Immunol., vol. 2, No. 10, pp. 995-1002, 1990.
Luxembourg, Alain, et al., "Biomagnetic Isolation of Antigen-Specific CD8+T Cells Usable in Immunotherapy", Nature Biotechnology, vol. 16, Mar. 1998, pp. 281-285.
Matsumura, M.. et al., In vitro peptide binding to soluble empty class I major histocompatibility complex molecules isolated from transfected *Drosophila melanogaster* Cells., Journal of Biol. Chem., vol. 267, No. 33, 23589-23595, 1992.
Maziarz et al, "Co-expression after Gene Transfer of Human HLA Heavy Chain and Humanβ2-Microglobulin in Mouse L Cells", Regulation of the Immune System: Abstract # 0336, Proceedings of the Dana-Farber Cancer Institute, Boston, MA 1983.
Mescher, Matthew, "Molecular Interactions in the Activation of Effector and Precursor Cytotoxic T Lymphocytes", Immunol. Review, 1995, No. 146, pp. 177-210.
Nepom, J. T., Acquisition of Syngeneic I-A Determinants by T Cells Proliferating in Response to Poly (Glu60 Ala30 Tyr10), J. of Immunol. vol. 127, pp. 888-892 Sep. 1981.
Noelle, R. et al. "Cognate Interactions between Helper T Cells and B Cells", Immunology Today, vol. 11, No. 10, 1990, pp. 361-368.
Nordon et al, "Ex Vivo Cell Therapy",, Academic Press: San Diego, Chapter 11:215-243 1999.
Osband et al, "Problems in the Investigational Study and Clinical Use of Cancer Immunotherapy", Immunol. Today, vol. 11, No. 6, 1990: pp. 193-195.
Penninger et al., "The Actin Cytoskeleton and Lymphocyte Activation", Cell, vol. 96, 9-12, Jan. 8, 1999.
Preckel et al., "Altered Hapten Ligands Antagonize Trinitrophenyl-Specific Cytotoxic T Cells and Block Internalization of Hapten-Specific receptors", J. Exp. Med, vol. 185, No. 10, May 19, 1997 pp. 1803-1813.
Riddel et al., "Principles for Adoptive T Cell Therapy of Human Viral Diseases", Annu. Rev. Immunol. 1995, 13:545-86.
Riddel et al. "Therapeutic reconstitution of Human Viral Immunity by Adoptive Transfer of Cytotoxic T Lymphocyte Clones", Current Topics in Microbiol. and Immuol., vol. 189, 1994 pp. 9-34.
Rivoltini, L. et al, "Induction of tumor-reactive CTL from peripheral blood and tumor-infiltrating lymphocytes of melanoma patients by in vitro stimulation with an immunodominant peptide of the human melanoma antigen MART-1", J. of Immunol. 1995, vol. 154: pp. 2257-2265.
Rosenberg, S. et al, "Use of tumor-infiltrating lymphocytes and interleukin-2 in the immunotherapy of patients with metastatic Melanoma", New England Journal of Medicine, Dec. 22, 1988, pp. 1676-1680.

Schumacher et al. "Peptide Selection by MHC Class I Molecules", Nature, vol. 350, Apr. 25, 1991, pp. 703-706.
Schwartz, Ronald, "Costimulation of T Lymphocytes: The Role of CD28, CTLA-4, and B7/BB1 in Interleukin-2 Production and Immunotherapy", Cell, vol. 71, 1065-1068, Dec. 1992.
Storkus, W. et al, "Identification of human melanoma peptides recognized by class I restricted tumor infiltrating T lymphocytes", Journal of Immunology, vol. 151, 3719-3727, No. 7, Oct. 1, 1993.
Schultze J.L. et al, "Autologous tumor infiltrating T cells cytotoxic for follicular lymphoma cells can be expanded in vitro", Blood May 1997, vol. 89, No. 10 pp. 3806-3816.
Sykulev Y. et al., "High-Affinity Reactions between Antigen-specific T-Cell Receptors and Peptides Associated with Allogeneic and Syngeneic Major Histocompatibiliy Complex Class I Proteins", Proc. Natl Acad. Sci., vol. 91, pp. 11487-11491, Nov. 1994.
Sparano, J.A. et al, "Randomized phase III trial of treatment with High-dose interleukin-2 either alone or in combination with interferon alfa-2a in patients with advanced melanoma", J. Clin. Oncol, vol. 11, No. 10, Oct. 1993, pp. 1969-1977.
Sprent et al., "Constructing Artificial Antigen-Presenting Cells from *Drosophila* Cells", Journal of Advances in Experimental Medicine and Biology, vol. 41, pp. 249-254, 1997.
Stryhn, A., et al., "Preformed Purified Peptide-Major Histocompatibility Class I Complexes are Potent Stimulators of Class I-Restricted T Cell Hybridomas", Eur. J. Immunol. 1994. 24:1404-1409.
Swain, S. et al., "Transforming Growth Factor-β and IL-4 Cause Helper T Cell Precursors to Develop into Distinct Effector Helper Cells that Differ in Lymphokine Secretion Pattern and Cell Surface Phenotype", J. of Immunology, vol. 147, 2991-3000, No. 9 Nov. 1, 1991.
Tureci, O., et al, "Identification of a Meiosis-Specific Protein as a Member of the Class of Cancer/Testis Antigens", Proc. Natl. Acad. Sci. vol. 95, pp. 5211-5216, Apr. 1998.
Udaka, K. et al, "Self-MHC Restricted Peptides Recognized by an Alloreactive T Lymphocyte Clone", J. of Immunology, 1996, 157: 670-678.
Weber, S., et al, "Specific Low-Affinity Recognition of Major Histocompatibility Complex Plus Peptide by Soluble T-Cell Receptor", Nature, vol. 356, Apr. 30, 1992, pp. 793-796.
Wentworth et al., "In Vitro Induction of Primary, Antigen-Specific CTL from Human Peripheral Blood Mononuclear Cells Stimulated with Synthetic Peptides", Mol. Immunol., vol. 32, No. 9 pp. 603-612, 1995.
Whiteside, T. L, et al,, "Generation and characterization of ex vivo propagated autologous CD8+Cells Used for Adoptive Immunotherapy of patients infected with human immunodeficiency virus", Blood, vol. 81, No. 8 (Apr. 15, 1993): pp. 2085-2092.
Wolfel, T. et al, Analysis of antigens recognized on human melanoma cells by A2-restricted cytolytic T lymphocytes (CTL): Int. J. Cancer: 55, 237-244 (1993).
Wolfel, T. et al, Isolation of Naturally Processed Peptides Recognized by Cytolytic T Lymphocytes (CTL) on Human Melanoma Cells in Association with HLA-A2.1, Int. J. Cancer: 57, 413-418 (1994).
Yang et al, "Major Histocompatibility Complex (MHC)-encoded HAM2 is Necessary for Antigenic Peptide Loading onto Class I MHC Molecules", J. of Biol. Chem., vol. 267, No. 17, Jun. 15, 1992, pp. 11669-11672.
Zhang, Xiaohong et al, "Control of CD4 Effector Fate: Transforming Growth Factor β1 and Interleukin 2 Synergize to Prevent Apoptosis and Promote Effector Expansion", J. Exp. Med, vol. 182, Sep. 1995, 699-709.
Brichard, Vincent et. al. "The Tyrosinase Gene Code for an Antigen Recognized by Autologous Cytolytic T. Lymphocytes on HLA-A2 Melanomas", J. Exp. Med.,1993 178(2) p. 489-495.
Guelly C., et al 'Activation Requirements of Circulating Antigen-Specific Human CD8+ Memory T Cells Probed with Insect Cell-Based Artificial Antigen-Presenting Cells' Eur.J.Immunol. vol. 32, Jan. 2002, pp. 182-192.
Latouche, Jean Baptiste, "Induction of Human Cytotoxic T Lymphocytes by Artificial Antigen-Presenting Cells", Mat. Biotechnol., 2000, 18 (4) p. 405-409.

(56) References Cited

OTHER PUBLICATIONS

Mackensen, Andreas, et. al., "Phase 1 Study in Melanoma Patients of a Vaccine with Peptide-Pulsed Dendritic Cells Generated In Vitro from CD34+ Hematopoietic Progenitor Cells", Int. J. Cancer, 2000, 86(3) p. 385-392.
Mitchell, Malcolm S. et al.: "Phase 1 trial of adoptive immunotherapy with cytolytic Tlymphocytes immunized against a tyrosinase epitope." Journal of Clinical Oncolgy: Official Journal of the American Society of Clinical Oncology, Feb. 15, 2002, vol. 20, No. 4, pp. 1075-1086, XP002354241, ISSN: 0732-183X.
Sun, Siquan, et. al., "Dual Function of *Drosophila* Cells as APCs for Naïve CD8+ T Cells: Implications for Tumor Immunotherapy", Immunity, 1996, 4 (6), p. 555-564.
Allison, et al. "Manipulation of Co-Stimulatory Signals to Enhance Anti-Tumor T-Cells Responses", Curr. Op. Immunology (1995) 7(5): pp. 682-686.
Bakker, et al. "Melancocyte-Lineage-specific Antigen gp100 is Recognized by Melanoma-Derived Tumor-Infiltrating Lymphocytes", J. Exp. Med. (1994) 179 (3): pp. 1005-1009.
Brossart, et al. "Identification of HLA-A2-Restricted T-Cell Epitopes Derived from the MUC1 Tumor Antigen for Broadly Applicable Vaccine Therapies", Blood, (1999) 93(12): pp. 4309-4317.
Gaugler, et al. "Human Gene MAGE-3 Codes for an Antigen Recognized on a Melanoma by Autologous Cytolytic T Lymphocytes", J. Exp. Med. (1994) 179(3): pp. 921-930.
Kawakami et al., "Recognition of Multiple Epitopes in the Human Melanoma Antigen gp100 by Tumor-Infiltrating T Lymphocytes Associated with In Vivo Tumor Regression", J. Immunol. (1995) 154(8) pp. 3961-3968.
Kawakami et al. Identification of the Immunodominant Peptides of the MART-1 Human Melanoma Antigen Recognized by the Majority of HIA-A2-Restricted Tumor Infiltrating Lymphocytes:, J. Exp. Med. (1994) 180(1): pp. 347-352.
Robbins, et al. "Recognition of Tyrosinase by Tumor-Infiltrating Lymphocytes from a Patient Responding to Immunotherapy", Cancer Res. (1994) 54: pp. 3124-3126.
Schneider, I. et al. "Differentiation of Larval *Drosophila* Eye-Antennal discs in Vitro", Exp. Zool. (1964) 156(1) pp. 91-104.
Skipper, et al. "An HLA-A2-Restricted Tyrosinase Antigen on Melanoma Cells Results from Post Translations Modification and Suggests a Novel Pathway for Processing of Membrane Proteins", J. Exp. Med. (1996) 183(2): pp. 527-534.
Zeling Cai, et. al. Transfected *Drosophila* cells as a probe for defining the minimal requirements for stimulating unprimed CD8+ T cells, Proc. Natl. Acad. Sci. U.S. A,. vol. 93, pp. 14736-14741. Dec. 1996, Immunology.
Agarwala, S.S. et al. "Melanoma", Immunotherapeutic Approaches, BioDrugs, 1999, (Sep.) 12,(3) pp. 193-208.
Babcock, B. et al. "Ovarian and Breast Cytotoxic T Lymphocytes Can Recognize Peptides from the Amino Enhancer of Split Protein of the Notch Complex", Molecular Immunology, 35, (1998) pp. 1121-1133.
Brichard, V. et al. "The Tyrosinase Gene Codes for an Antigen Recognized by Autologous Cytolytic T Lymphocytes on HLA-A2 Melanomas", J. Exp. Med. vol. 178, Aug. 1993, pp. 489-495.
Brossart, P. et al. "Identification of HLA-A2-Restricted T-Cell Epitopes Derived from the MUC1 Tumor Antigen for Broadly Applicable Vaccine Therapies", Blood Journal, vol. 93, No. 12 (Jun. 15, 1999), pp. 4308-4317.
Chen, Ji-Li et al. "Identification of NY-ESO-1 Peptide Analogues Capable of Improved Stimulation of Tumor-Reactive CTL", The Journal of Immunology, 2000, 165: pp. 948-955.
Creagan, E.T. et al. "Phase II Study of Recombinant Leukocyte A Interferon (rIFN-αA) in Disseminated Malignant Melanoma", Cancer 54 (1984) pp. 2844-2849.
Dorval, T. et al. "Clinical Phase II Trial of Recombinant DNA Interferon (Interferon Alfa 2b) in Patients with Metastatic Malignant Melanoma", Cancer 58 (1986) pp. 215-218.

Fisk, B. et al. "Identification of an Immunodominant Peptide of HER-2/neu Protooncogene Recognized by Ovarian Tumor-Specific Cytotoxic T Lymphocyte Lines", J. Exp. Med. vol. 181, Jun. 1995, pp. 2109-2117.
Kawashima, I. et al. "The Multi-Epitope Approach for Immunotherapy for Cancer: Identification of Several CTL Epitopes from Various Tumor-Associated Antigens Expressed on Solid Epithelial Tumors", Human Immunology 59, (1998) pp. 1-14.
Kirkwood, J.M. et al. "High- and Low-Dose Interferon Alfa-2b in High-Risk Melanoma: First Analysis of Intergroup Trial E1690/S9111/C9190", Journal of Clinical Oncology, 18 (12) Jun. 2000, pp. 2444-2458.
LaTouche, J-B et al. "Induction of Human Cytotoxic T Lymphocytes by Artificial Antigen-Presenting Cells", Nature Biotechnology, vol. 18, Apr. 2000, pp. 405-409.
Legha, S.S., "Interferons in the Treatment of Malignant Melanoma, a Review of Recent Trials", Cancer 57: (1986) pp. 1675-1677.
Mackensen, A. et al. "Phase I Study in Melanoma Patients of a Vaccine with Peptide-Pulsed Dendritic Cells Generated In Vitro From CD34 Hematopoietic Progenitor Cells", Int. J. Cancer: 86, (2000) pp. 385-392.
Stimpfli, M. et al. "Expression of Mucins and Cytokeratins in Ovarian Cancer Cell Lines", Cancer Letters 145 (1999) pp. 133-141. Elsevier Science, Ireland.
Sun, S. et al. "Dual Function of *Drosophila* Cells as APCs for naïve CD8+ T Cells: Implications for Tumor Immunotherapy", Immunity, vol. 4, Jun. 1996, pp. 555-564. The Scripps Research Institute, La Jolla, California.
Vonderheide, R.H. et al. "Equivalent Induction of Telomerase-Specific Cytotoxic T Lymphocytes from Tumor-Bearing Patients and Healthy Individuals", Cancer Research 61, Dec. 1, 2001, pp. 8366-8370. Departments of Adult Oncology Boston, MA.
Vissers, J.L. et al. "The Renal Cell Carcinoma-Associated Antigen G250 Encodes a Human Leukocyte Antigen (HLA)-A2.1-Restricted Epitope Recognized by Cytotoxic T Lymphocytes", Cancer Research 59, Nov. 1, 1999, pp. 5554-5559. University Hospital Nijmegen St. Radboud, the Netherlands.
Yee, C. et al. "Melanocyte Destruction After Antigen-Specific Immunotherapy of Melanoma: Direct Evidence of T Cell-Mediated Vitiligo", J. Exp. Med. vol. 192, No. 11, Dec. 4, 2000, pp. 1637-1643. Clinical Research Division Seattle, Washington.
deVries, I. Jolanda M. et al. "Maturation of Dendritic Cells is a Prerequisite for Inducing Immune Responses in Advanced Melanoma Patients", Clinical Cancer Research, vol. 9, Nov. 1, 2003, pp. 5091-5100.
Rosenberg, S.A. et al. "Adoptive Cell Therapy for the Treatment of Patients with Metastatic Melanoma", Current Opinions in Immunology, 2009, 21, pp. 233-240. Elsevier.
Japanese Pat App No. 2012-20842 Filed Feb. 2, 2012, Japanese Office Action Dated Oct. 25, 2013.
Kim et al., Folate Binding Protein Peptide 191-199 Presented on Dendritic Cells Can Stimulate CTL from Ovarian and Breast Cancer Patients:, Anticancer Res. (1999) 19(4B); 2907-2916.
Chen et al., "Marked Differences in Human Melanoma Antigen-Specific T Cell Responsiveness after Vaccination Using a Functional Microarray" PLOS Medicine 2(10) 1018-1030 (2005).
Robbins et al., "A Mutated 62-Catenin Gene Encodes a Melanoma-specific Antigen Recognized by Tumor Infiltrating Lymphocytes" Journal of Experimental Medicine 183; 1185-1192 (1996).
Yee et al., "Prospects for adoptive T cell therapy" Current Opinion Immunology 9; 702-708 (1997).
Richards et al, "Therapeutic and Immunologic Evaluation of Autologous CTL Generated Using Transgenic Drosphila Cells as APC's for the Treatment of Melanoma", Amer. Soc. Clin Oncol. 20 Abstract 1015, pp. 254A (May 2001).
Gong et al., "Induction of Antitumor Activity by Immunization with Fusions of Dendritic and Carcinoma Cells", Nature Medicine, Nature Publishing Group, New York, NY, US, vol. 3, No. 5, pp. 558-561, May 1, 1997.
Uwe Trefzer et al., Hybrid cell vaccination for cancer immune therapy: First clinical trial with metastatic melanoma:, International Journal of Cancer, vol. 85, No. 1, p. 618, Mar. 1, 2000.

(56) References Cited

OTHER PUBLICATIONS

Hans W Nijman et al., "Identification of peptide sequences that potentially trigger HLA-A2. 1-restricted cytotoxic T lymphocytes", Eur. J. Immunol., vol. 23, pp. 1215-1219, Jan. 1, 1993.

Brossart Peter, et al., "Induction of cytotoxic T-lymphocyte responses in vivo after vaccinations with peptide-pulsed dendritic cells", Blood, American Society of Hematology, US, vol. 96, No. 9, pp. 3102-3108, Nov. 1, 2000.

European Search Report for EP14187466 dated Feb. 3, 2015.

\* cited by examiner

Figure 2
Panel A
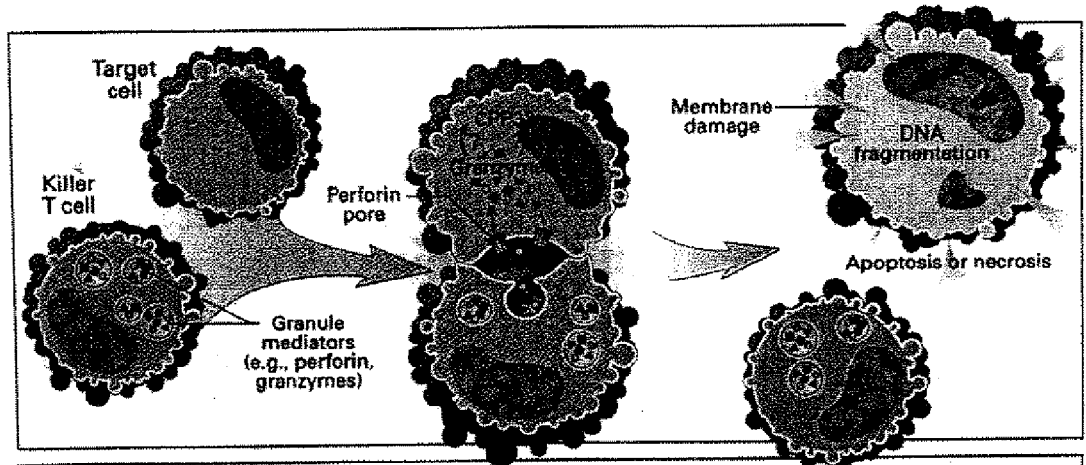
Panel B
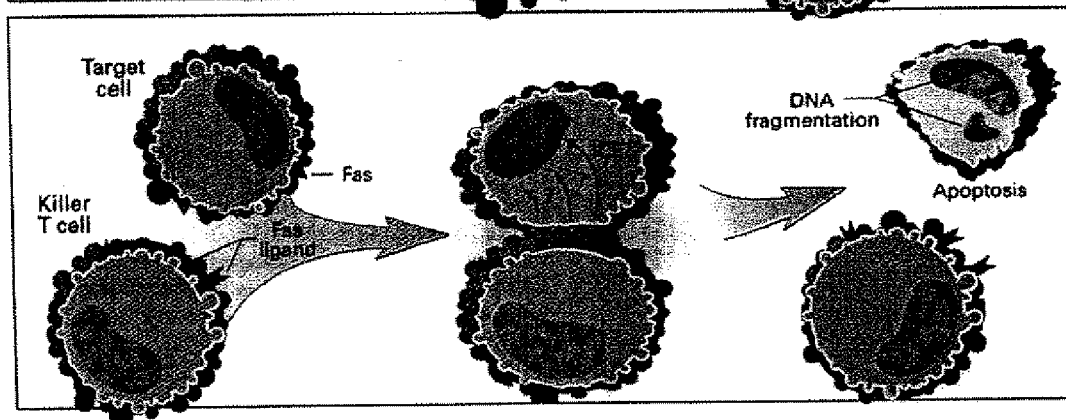

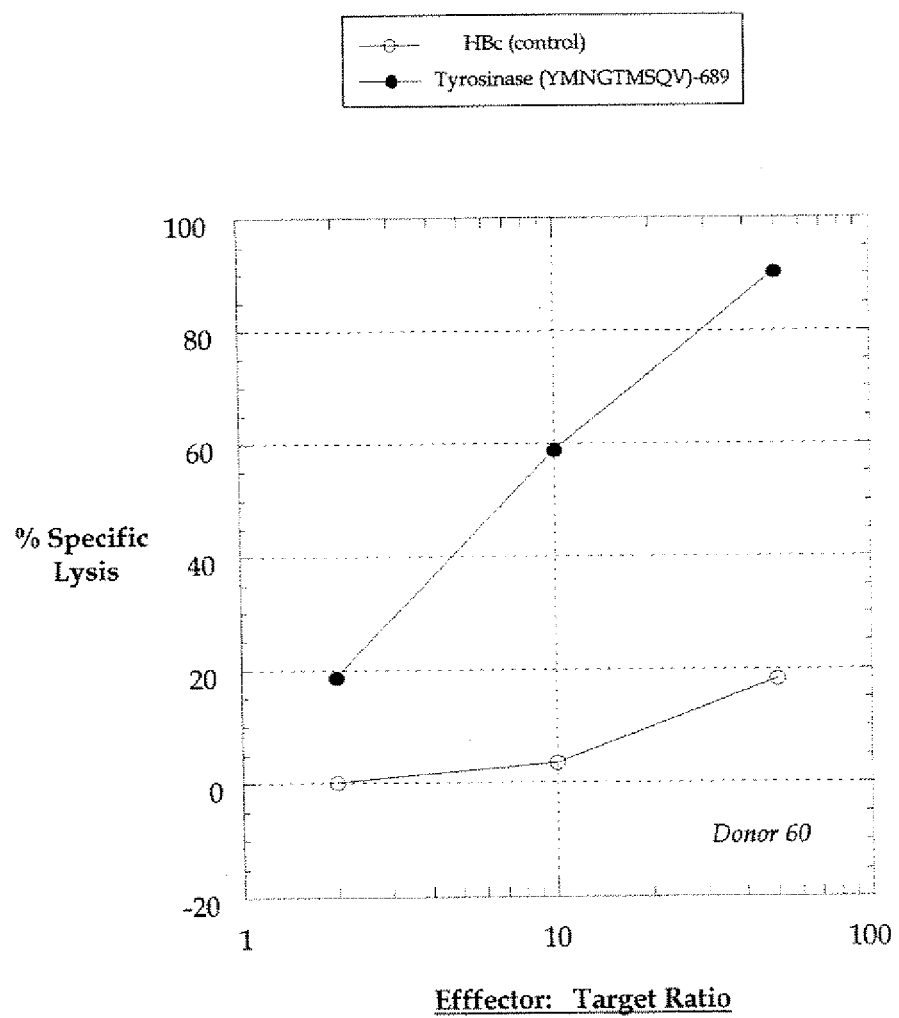

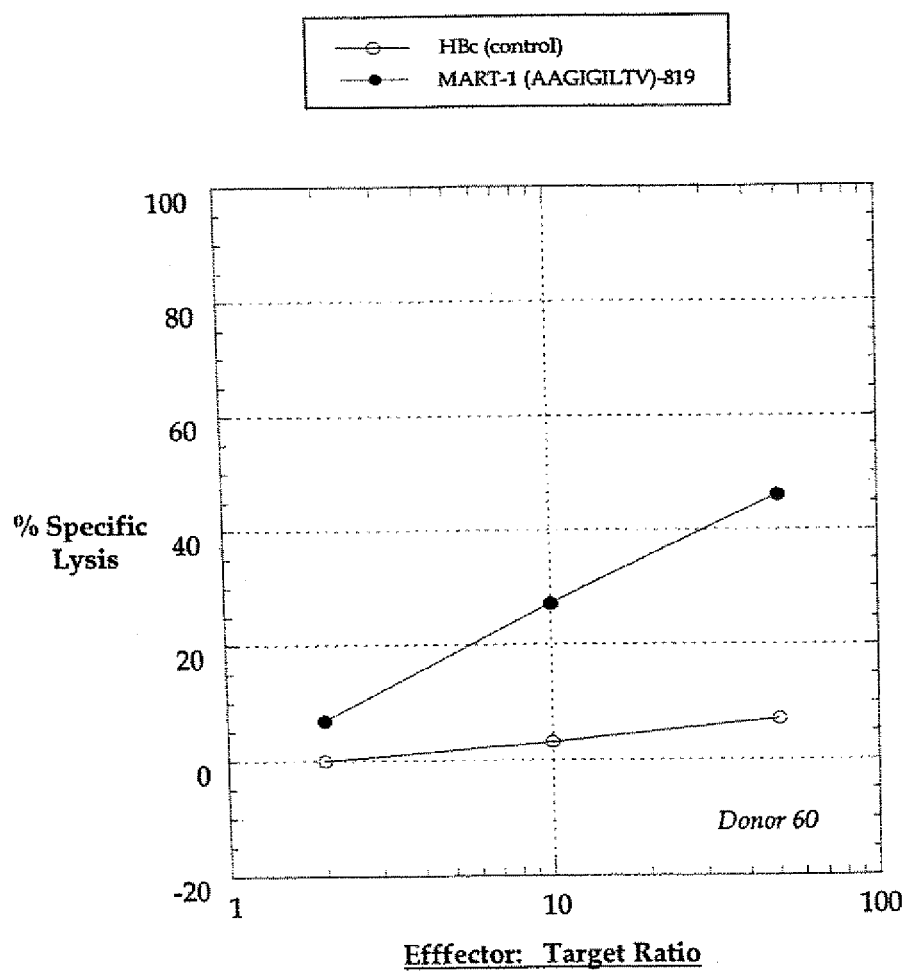

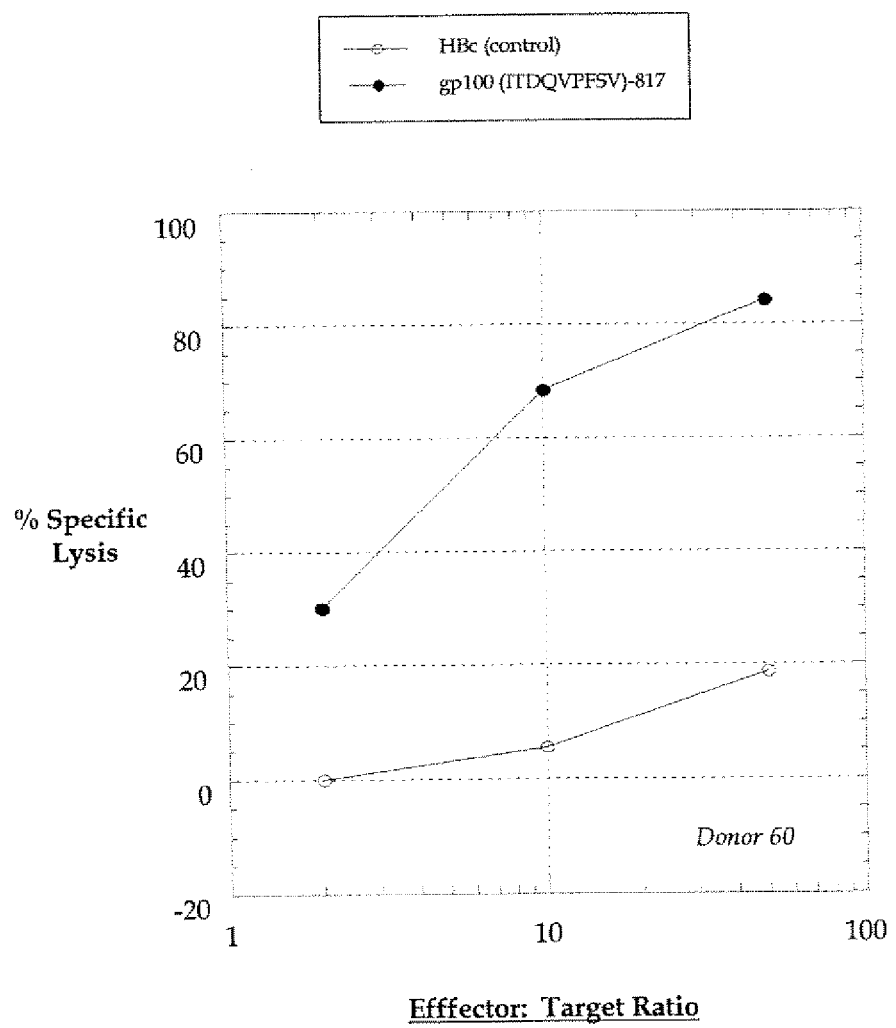

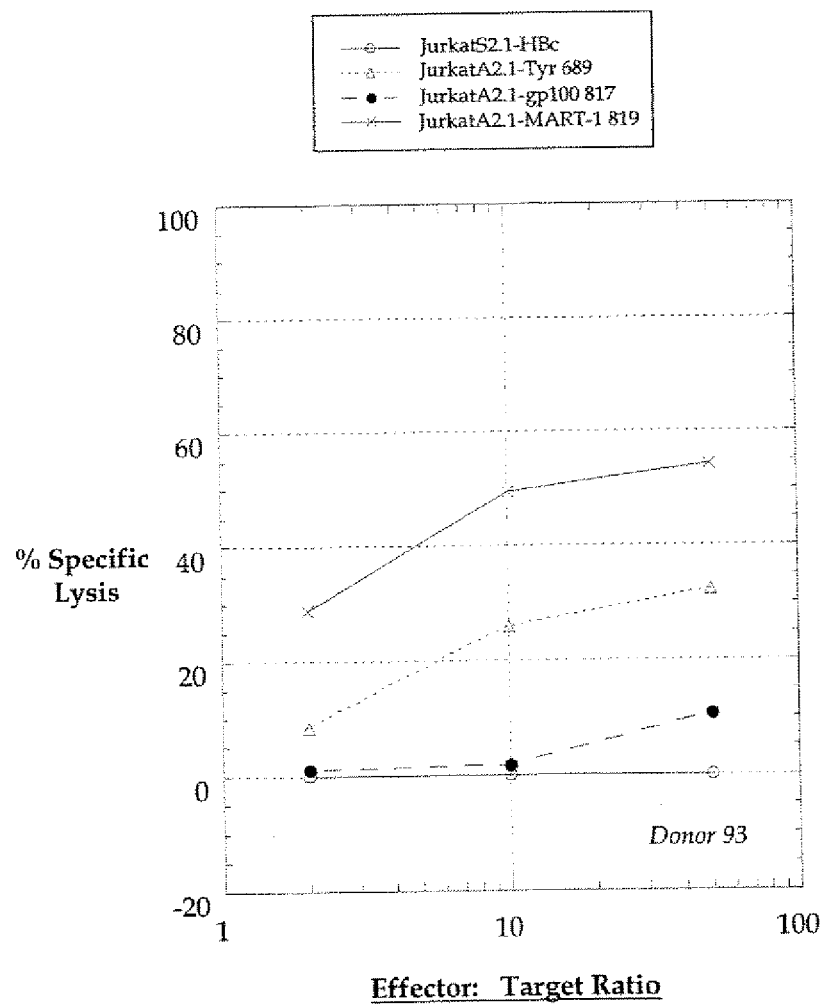

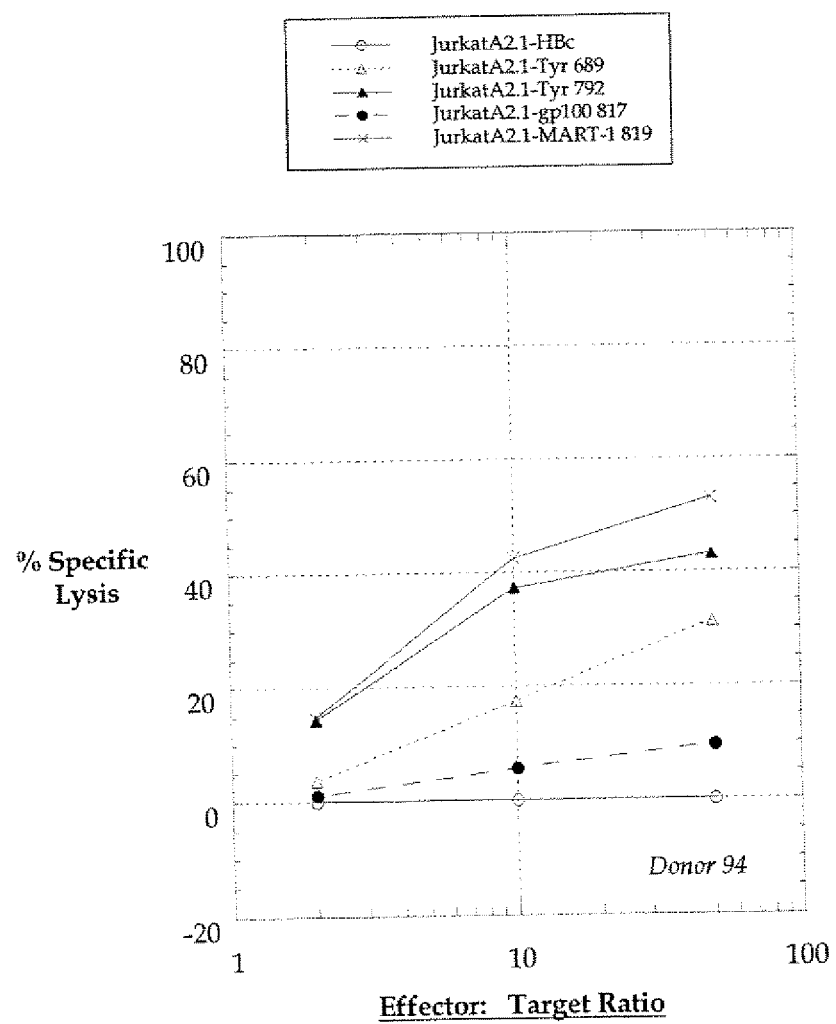

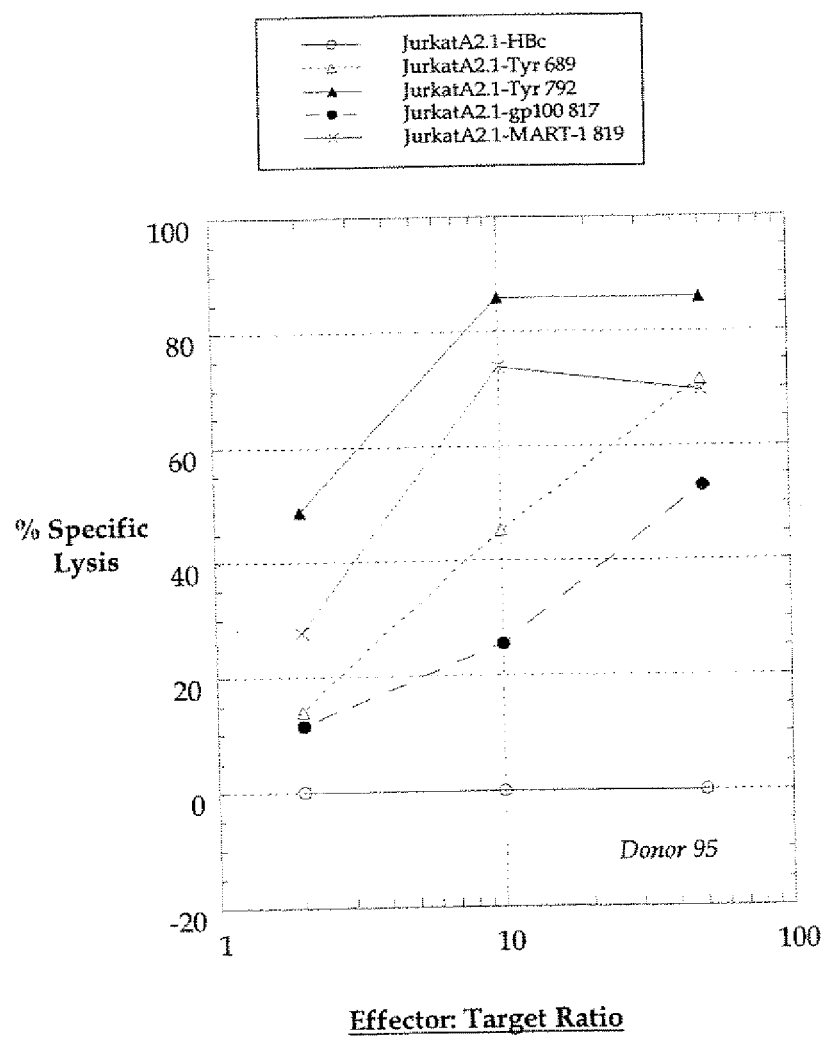

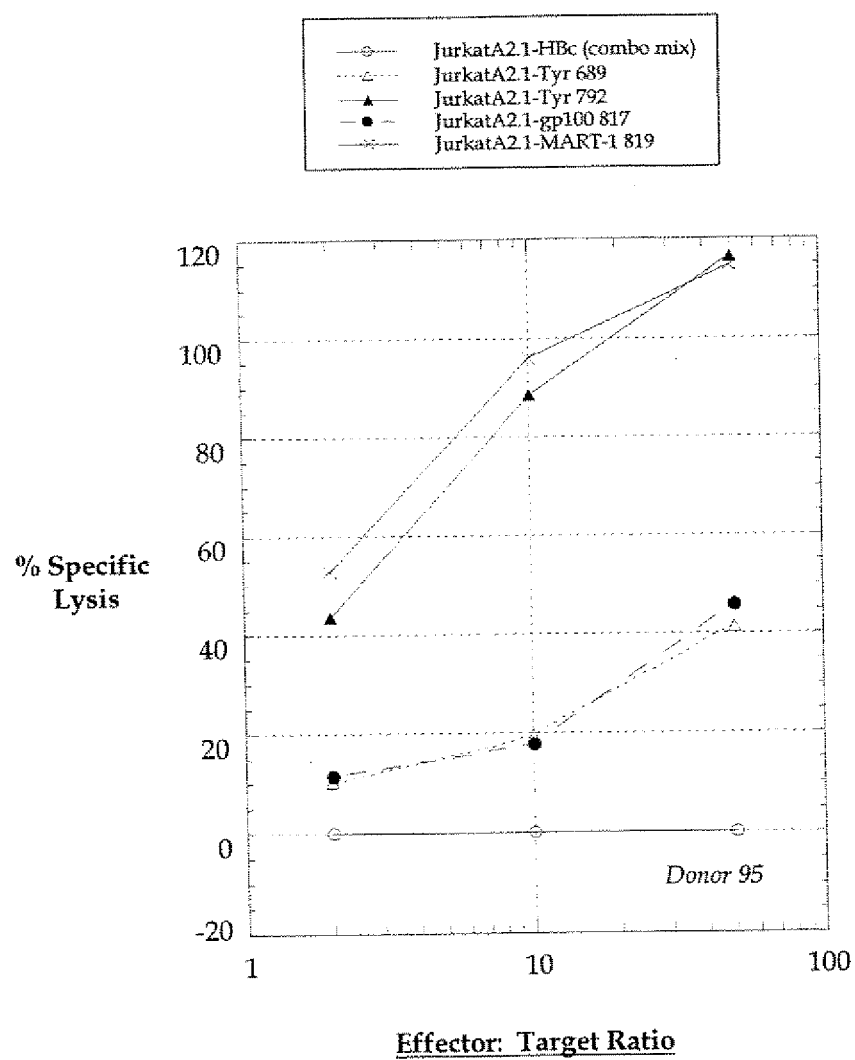

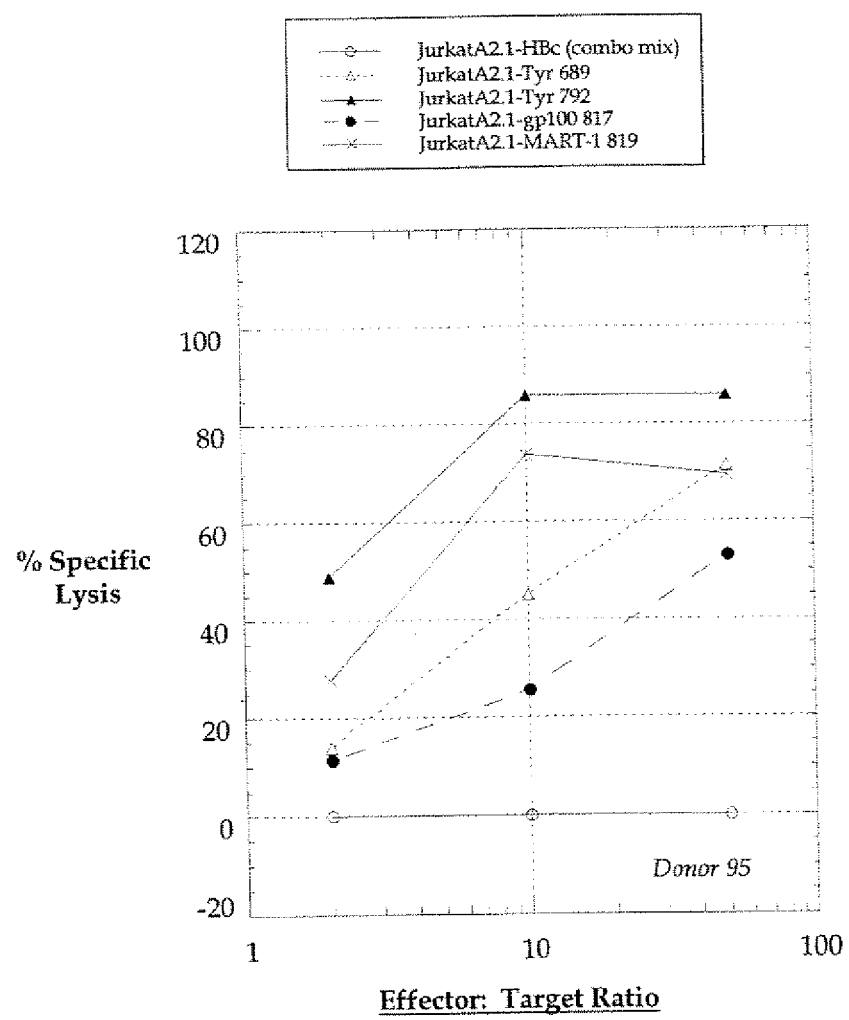

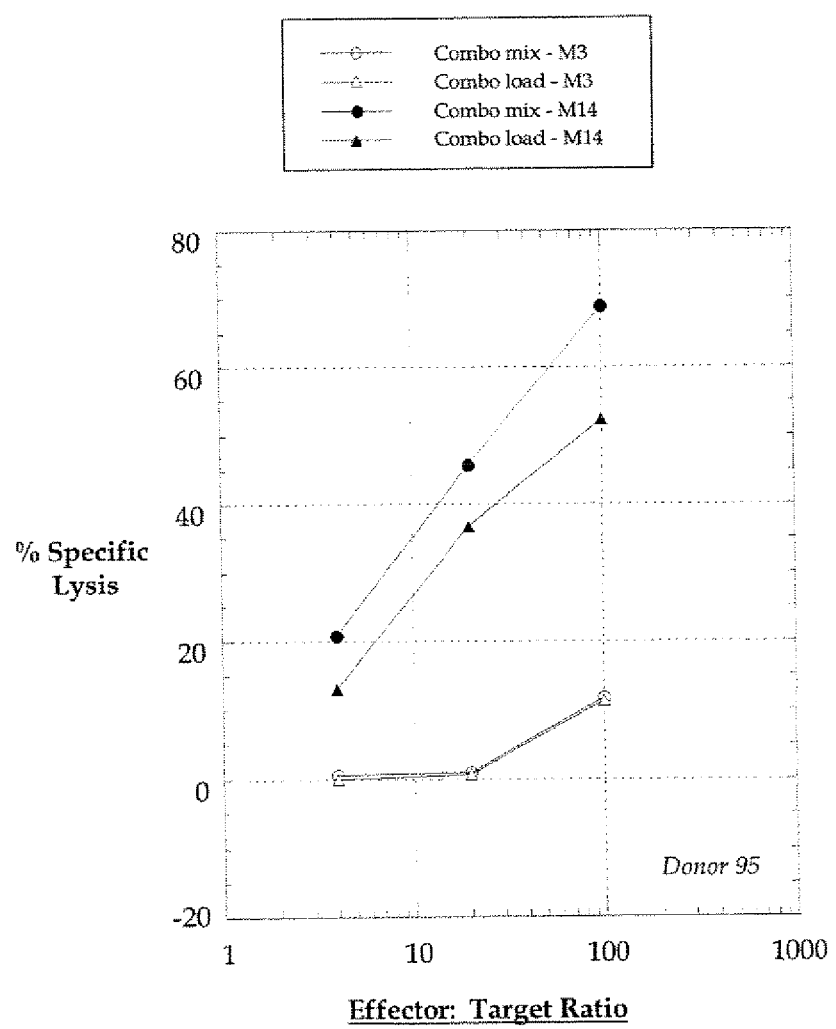

Figure 7
Panel A
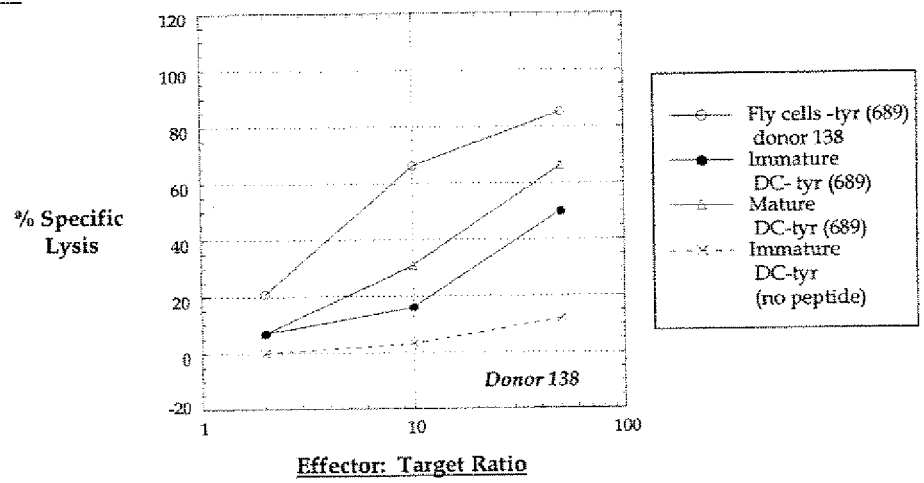
Panel B
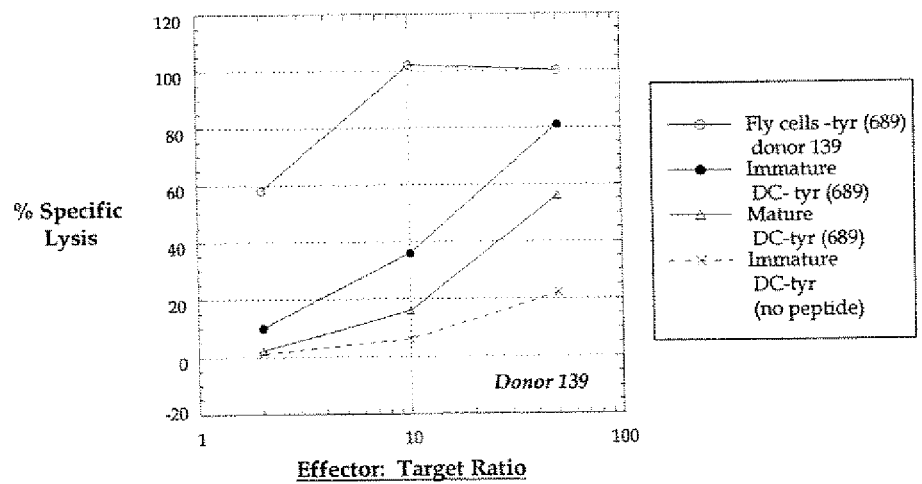

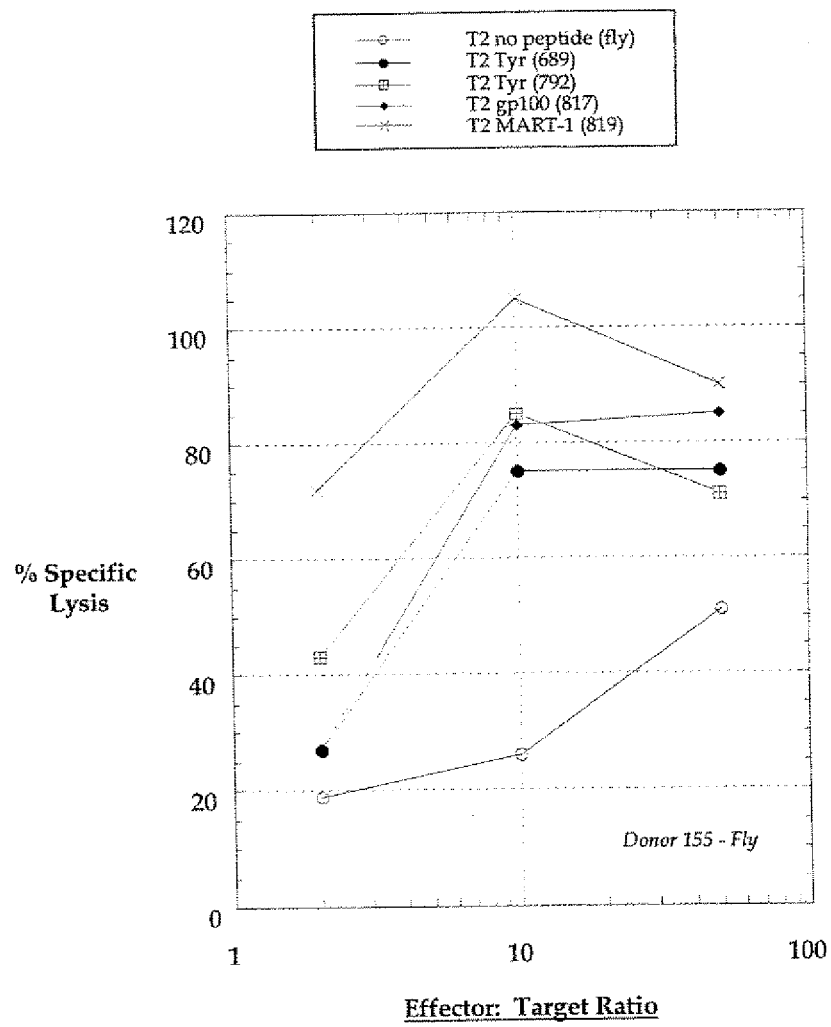

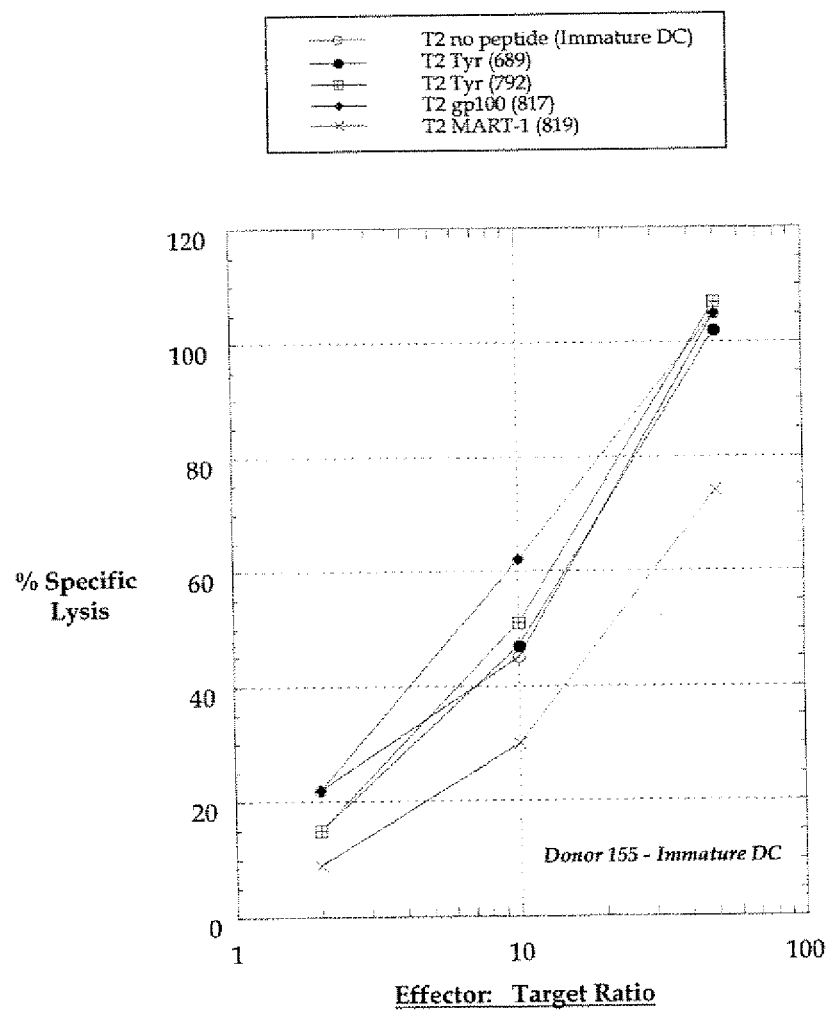

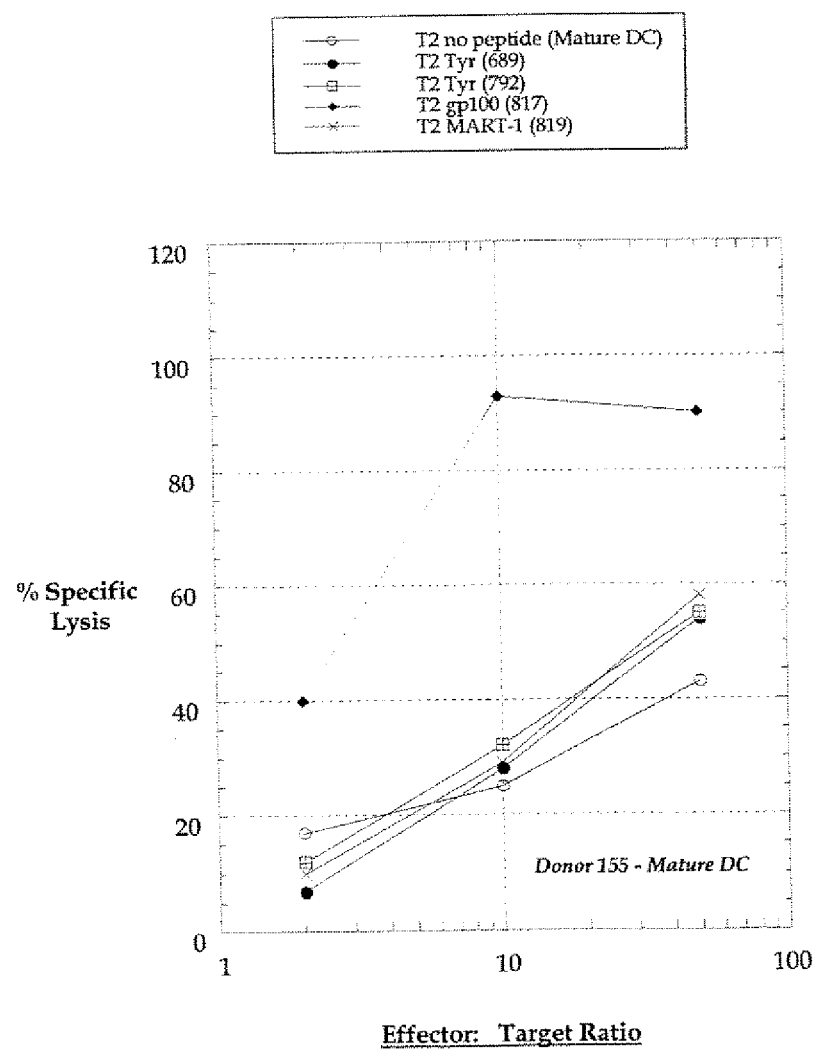

Figure 10
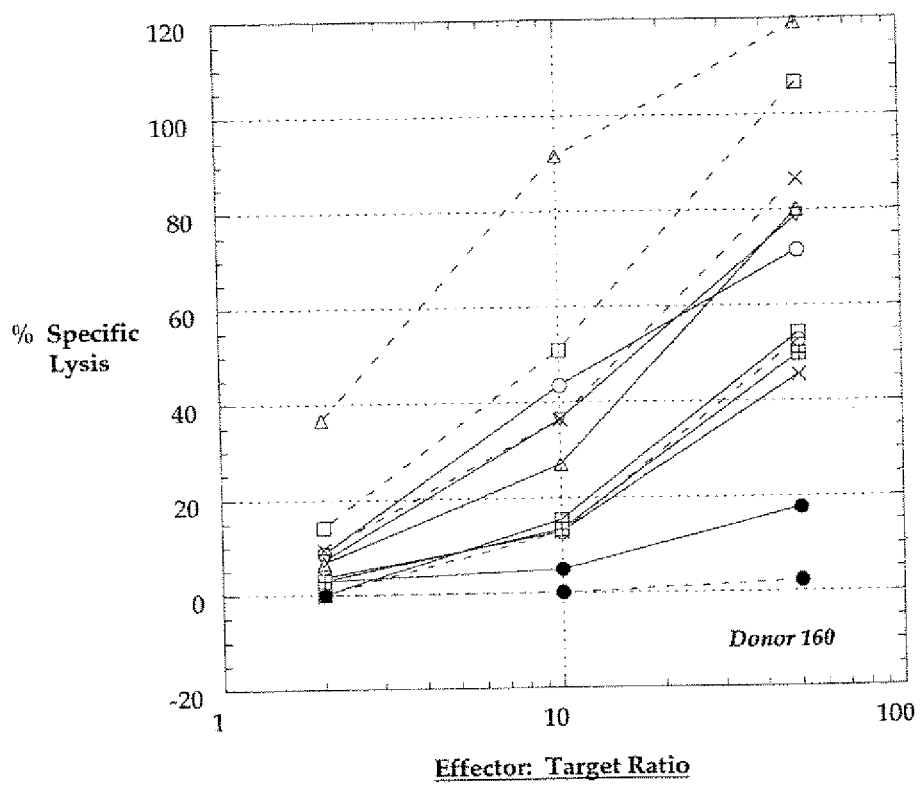
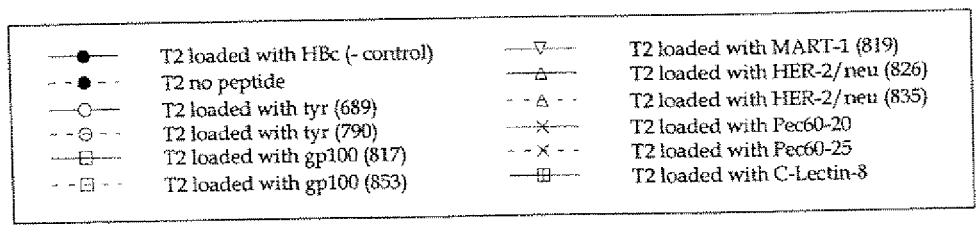

Panel A

Panel B

Figure 15
Panel A
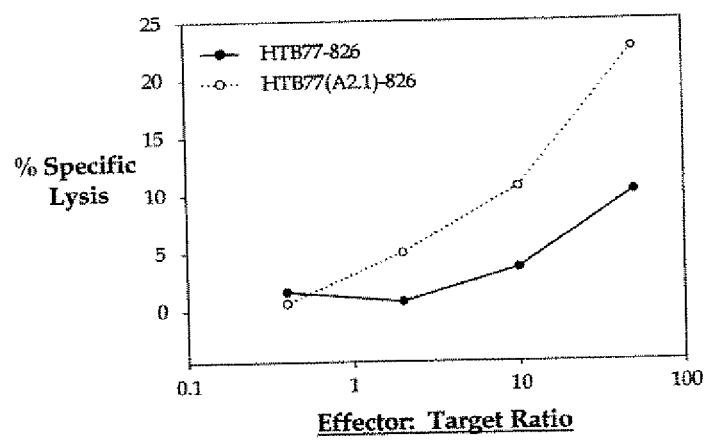
Panel B
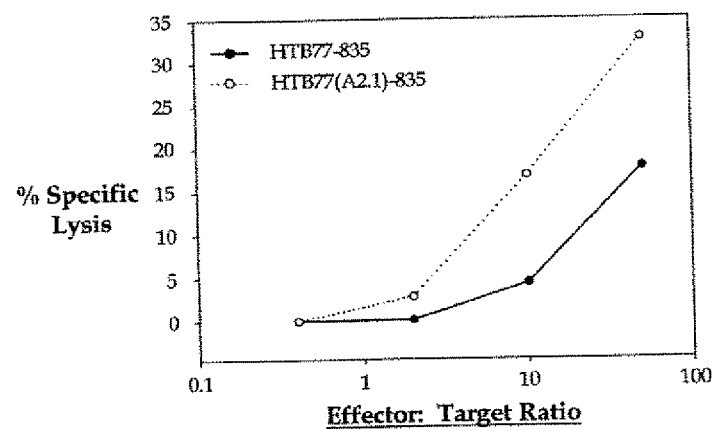

Figure 15
Panel C
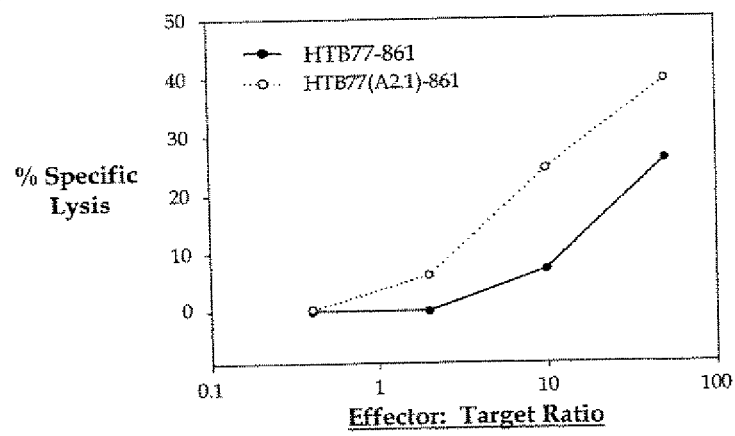
Panel D
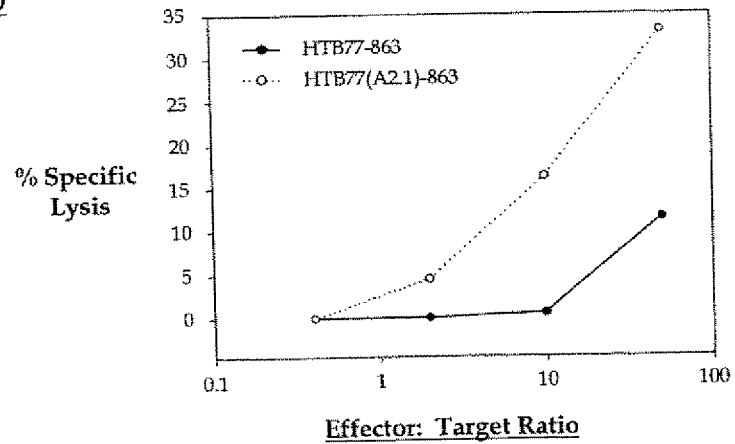

Figure 18
Panel A
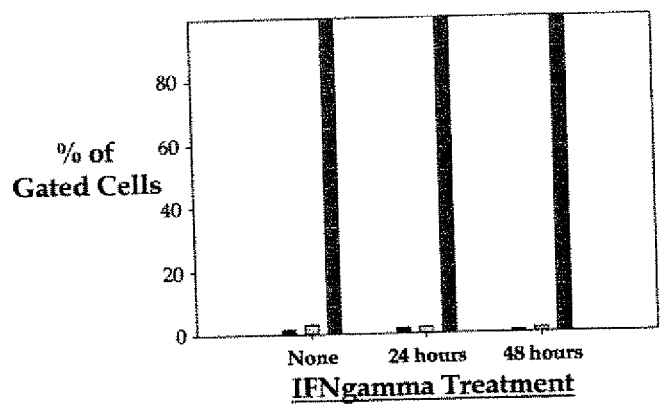
Panel B
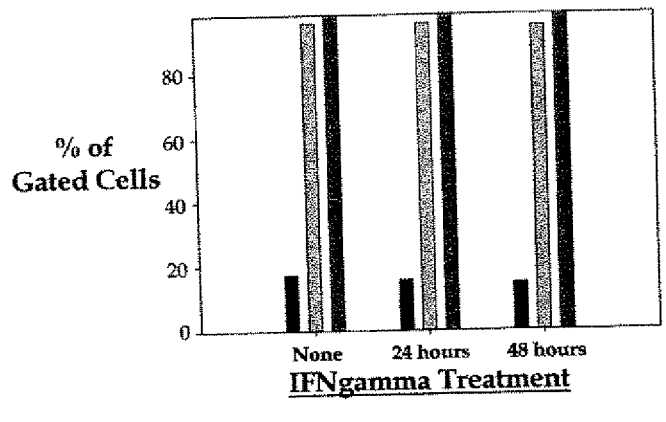
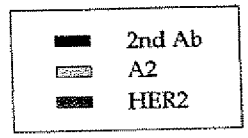

Figure 21
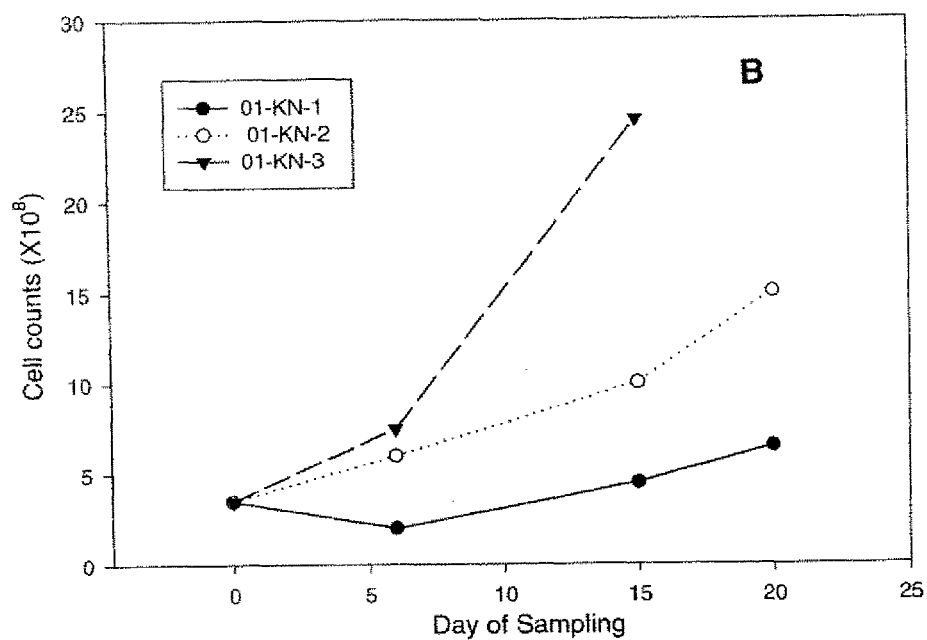
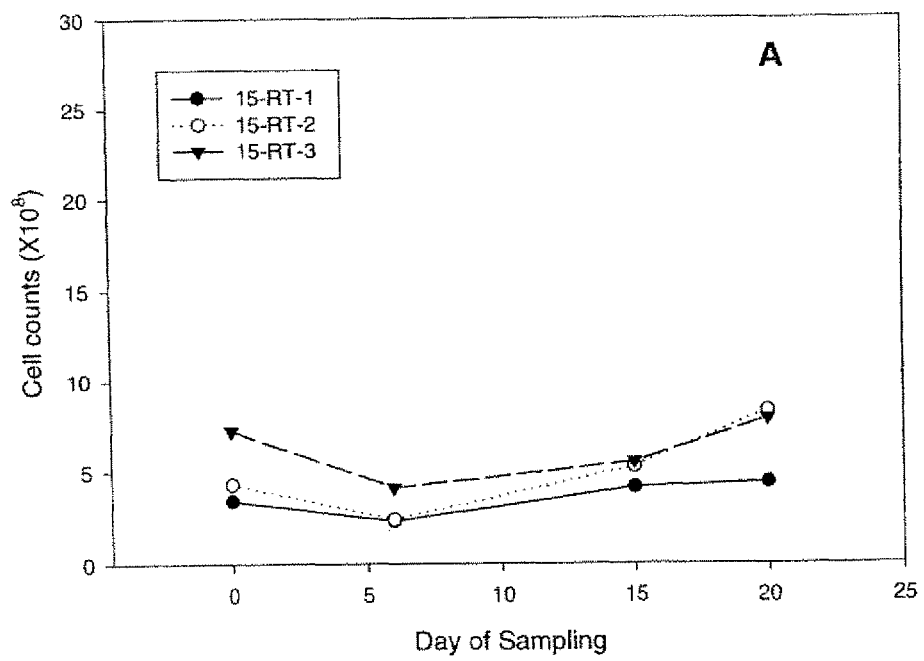

CELL THERAPY METHOD FOR THE TREATMENT OF TUMORS

CROSS REFERENCES

This application is a continuation of U.S. patent application Ser. No. 10/289,566, filed Nov. 7, 2002 now abandoned, which is a continuation-in-part of U.S. patent application Ser. No. 10/080,013 filed on Feb. 19, 2002 now abandoned, which in turn claims priority from Provisional Patent Application Ser. No. 60/270,252, filed Feb. 20, 2001, the contents of these applications is hereby incorporated by reference in their entirety.

FIELD OF THE INVENTION

The present invention relates to a cell therapy method for the treatment of tumors. In particular, the present invention relates to a treatment regimen for melanoma using ex vivo-generated autologous T lymphocytes with specificity for melanoma-associated target antigen.

BACKGROUND OF THE INVENTION

Cancer continues to be a major health problem, despite significant progress made in the area of treatment. The standard treatment regimes of chemotherapy, radiation therapy, surgical intervention and combinations of the three, often fail to produce a long lasting cure. In many cases, the cancer patient having undergone the treatment often relapses back to the disease condition after some period of time, further exacerbating the problem.

Another factor complicating development of a cancer treatment is that cancers have been found to be caused not by a single biological agent or factor, but rather by a combination of agents and factors. Unlike most medical treatments where a single causative agent or event is the focus of the treatment, cancer therapy requires addressing a plurality of biological factors.

In recent years, research has been directed to developing cancer therapies that utilize the patient's own immune system. One such approach is adoptive immunotherapy. Adoptive immunotherapy calls for using the patient's own cells to generate cytotoxic T lymphocytes CTLs) to treat a tumor or cancerous cells.

Since melanoma is known for it's potential to elicit immune responses and is resistant to currently used regimens of systemic treatment, such as chemotherapy and hormone-therapy, most preclinical and clinical studies of immunotherapy regimes target this malignancy. Melanoma is a significant health problem. Over the past four decades the incidence of melanoma has been increasing at a higher rate than any other type of cancer. Although most melanomas are managed by routine surgical excision, for patients with malignant melanoma not amenable to surgical extirpation, treatment options are limited. Dacarbazine remains the drug of choice in disseminated melanoma, but remissions are usually short lived. Interleukin and biochemotherapy have yielded good results but the percentage of patients benefiting this therapy is small. Although high dose interferon increases survival rates in some patients, interferon remains a controversial drug that is not easily tolerated. Sequential chemotherapy has promise, but, current treatment options for individuals suffering from metastatic melanoma are unsatisfactory.

Current immunotherapeutic approaches for treating metastatic melanoma include the administration of melanoma-associated peptides alone, or in combination with exogenous cytokines, gene-modified tumor cells, Dendritic cells loaded with defined peptides or dendritic cells presenting a full complement of antigenic epitopes resulting from internally processed proteins. These approaches attempt to boost T and/or B cell responses in an effort to cure the disease. These approaches remain largely unproven as viable clinical treatment regimes for human patients. Aside from the problem of identifying the proper epitopes with which to immunize the CTL's, the current approaches do not provide for a method of presenting a sufficient number of different epitopes to APCs in order to adequately target multiple antigens to effectively treat the cancer.

The present invention fulfills unmet needs, by providing a cell therapy method for the treatment of tumors. In particular, the present invention relates to a treatment regimen for melanoma using ex vivo-generated autologous T lymphocytes with specificity for melanoma-associated target antigen. Concomitant administration of either IFN-α or IL-2, or both cytokines at specific times and doses can benefit the priming of tumor cells for lysis by the antigen-specific T cells and the in vivo persistence of the CTLs.

SUMMARY OF THE INVENTION

The present invention provides a non-naturally occurring antigen-presenting cell (nnAPC) capable of presenting up to ten or more different peptides simultaneously, methods of manufacturing nnACP, methods of using said nnACP for the treatment of cancer, particularly malignant melanoma.

In a first aspect, the present invention relates to a method for treating a viral infection in a subject comprising:

preparing a non-naturally occurring antigen-presenting cell line(nnAPC), wherein said nnAPC is capable of presenting up to about fifteen different peptide molecules associated with said viral infection simultaneously wherein said peptide molecules are each about six to twelve amino acids in length, harvesting $CD8^+$ cells from the subject or a suitable donor;

stimulating said $CD8^+$ cells with an nnAPC cell line;

adding the $CD8^+$ cells to media that contains a cytokine selected from the group consisting of IL-2, IL-7 or conditioned growth medium (CGM), wherein said cytokines can be used individually or in combination;

mixing unsuspended peripheral blood monocytes, or CD-8 depleted peripheral blood monocytes collected from said subject or a suitable donor with about 1 to 50 μg/ml of one of the peptides that the nnAPC can simultaneously present;

irradiating the peripheral blood monocyte suspension with a sufficient dose of γ-radiation necessary to sterilize all components in the suspension, except the desired peripheral blood monocytes;

isolating adherent peripheral blood monocytes;

loading the adherent peripheral blood monocytes with about 1 ug/ml to 50 μg/ml of each peptide;

combining the $CD8^+$ cells with the adherent peripheral blood monocytes at a ratio of about ten $CD8^+$ cells to one peripheral blood monocyte; and introducing the $CD8^+$ suspension into the subject.

In one embodiment of this method the nnAPC is capable of presenting up to about ten peptide molecules and preferably the peptide molecules are about eight to ten amino acids in length. Preferably the molecules are in a concentration range of about 10 nM to 100 μM. Also preferably the cytokine component is IL-2 or IL-2 and IL-7 in combination. In another embodiment of this method the dose of γ-radiation is about 3,000 to 7,000 rads and preferably about 5,000 rads.

The invention also relates to a method for treating a subject with melanoma, comprising the steps of:

administering to the subject an effective amount of interferon-alfa that is capable of enhancing the expression of tumor antigen on the surface of the tumor; and inoculating said subject with an effective amount of autologous cytotoxic T lymphocytes with specificity for melanoma-associated target antigen.

In a preferred embodiment of this method, the method further comprises the step of administering to the subject an effective amount of interleukin-2 that is capable of enhancing the in vivo maintenance of the autologous cytotoxic T lymphocytes with specificity for melanoma-associated target antigen. Preferably the interferon-alfa is selected from interferon-alfa-2a or interferon-alfa-2b and the effective amount of interferon-alfa is about 10 $MU/m^2$/day and is subcutaneously administered to the subject consecutively from day 5 to day 1 prior to inoculating said subject with the effective amount of autologous cytotoxic T lymphocytes with specificity for melanoma-associated target antigen. Also preferably the effective amount of autologous cytotoxic T lymphocytes with specificity for melanoma-associated target antigen is about 1–10×$10^9$ cells/infusion. Also preferably the autologous cytotoxic T lymphocytes with specificity for melanoma-associated target antigen are obtained by a method comprising steps of: preparing a non-naturally occurring antigen-presenting cell line (nnPAC), wherein the nnAPC is capable of presenting up to about fifteen different epitopes associated with the melanoma simultaneously where each epitope is a peptide of eight to ten amino acids in length; loading the nnAPC with up to about fifteen different epitopes associated with the melanoma; harvesting CDS8+ cells from the subject, stimulating the CD8+ cells with the epitope-loaded nnAPC cell line to obtain CD8+ cells specific for the melanoma; growing the CD8+ cells specific for the melanoma in media containing IL-2 and IL-7; mixing CD8-depleted peripheral blood monocytes collected from the subject with each epitope that the nnAPC has been loaded with; irradiating the CD8-depleted peripheral blood monocytes with γ-radiation; isolating adherent CD8-depleted peripheral blood monocytes; loading the adherent peripheral blood monocytes with each epitope that the nnAPC has been loaded with; restimulating the CD8+ cells specific for the melanoma with the epitope-loaded adherent peripheral blood monocytes; growing the restimulated CD8+ cells specific for the melanoma in media containing IL-2 and IL-7; and expanding the restimulated CD8+ cells specific for the melanoma by OKT3 antibody stimulation.

Preferably the restimulating step can be repeated at least one more time. In another preferred embodiment of is method, the non-naturally occurring antigen-presenting cell line is loaded with epitopes that are peptides derived from tyrosinase, gp100, and MART-1 and preferably the non-naturally occurring antigen-presenting cell line is loaded with epitopes comprising amino acid sequences of SEQ ID NO: 1, SEQ ID NO: 2, SEQ ID NO: 4, SEQ ID NO: 5, and SEQ ID NO: 6. Also preferably the effective amount of interleukin-2 is about 3 MIU/day and is subcutaneously administered to the subject consecutively from day 0 to day 28 after inoculating said subject with the effective amount of autologous cytotoxic T lymphocytes with specificity for melanoma-associated target antigen. Also preferably the method is repeated at an interval of about 2 months. In a preferred embodiment the method is repeated for at least two cycles and further comprises the step of evaluating a response in said subject after each cycle.

In yet another preferred embodiment of this method, the method comprises the steps of: subcutaneously administering to the subject 10 $MU/m^2$/day of interferon-alpha-2b consecutively from day 5 to day 1 prior to inoculating said subject with autologous cytotoxic T lymphocytes with specificity for melanoma-associated target antigen; infusing about 1–10×$10^9$ cells/infusion of the autologous cytotoxic T lymphocytes with specificity for melanoma-associated target antigen, and subcutaneously administering to the subject about 3 MIU/day of interleukin-2 consecutively from day 0 to day 28 after inoculating said subject with the autologous cytotoxic T lymphocytes with specificity for melanoma-associated target antigen.

BRIEF DESCRIPTION OF THE DRAWINGS

FIG. 2, Panels A and B: This figure is a two panel graphical depiction of mechanisms of lymphocyte-mediated cytosis.

FIG. 4, Panels A, B and C:

This figure shows the result of an experiment where three melanoma peptides, Tyrosinase (YMNGTMSQV; SEQ ID NO: 1)-689 in Panel A, MART-1 (AAGIGILTV; SEQ ID NO: 6)-819 in Panel B, and gp 100 (ITDQVPFSV; SEQ ID NO: 4)-817, were tested for the ability to raise CTLs when added as single epitopes on Drosophila cells. In this donor (#60), CTL activity was elicited to each of the peptides when added alone to three different Drosophila preparations. The specificity of the response was compared with control HBc peptide, a high affinity binder.

FIG. 5, Panels A, B and C: This figure shows the results of a series of experiments where up to four different peptides were added to single Drosophila cells. CTL activity against each of the represented peptides was seen after a three-week stimulation protocol and is graphically depicted in this figure. Results from three different donors (#93, 94, 95) are represented.

FIG. 6, Panels A, B and C: This figure shows CTL activity after two different primary in vitro stimulation protocols.

FIG. 7, Panels A and B: This figure compares the ability of Drosophila cells versus dendritic cells to elicit CTL responses to a single peptide epitope following standard stimulation protocols.

Figure 8:
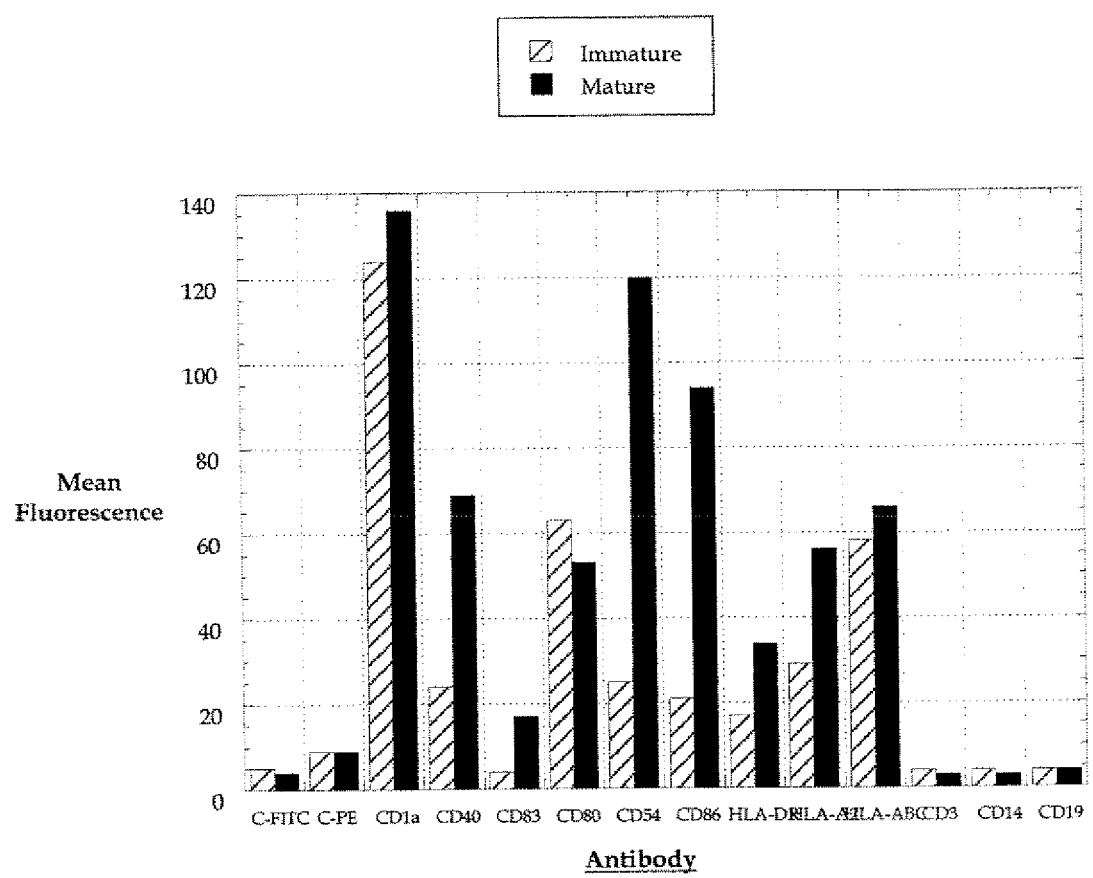

FIG. 8: This figure shows that the dendritic cells displaying either a mature or immature phenotype were not as efficient as Drosophila cells in eliciting specific CTL responses when defined peptides were used to pulse the cells.

FIG. 9, Panels A, B and C:

This figure shows CTL activity generated by a single donor to three different in vitro stimulation protocols presenting four peptides.

Figure 11:
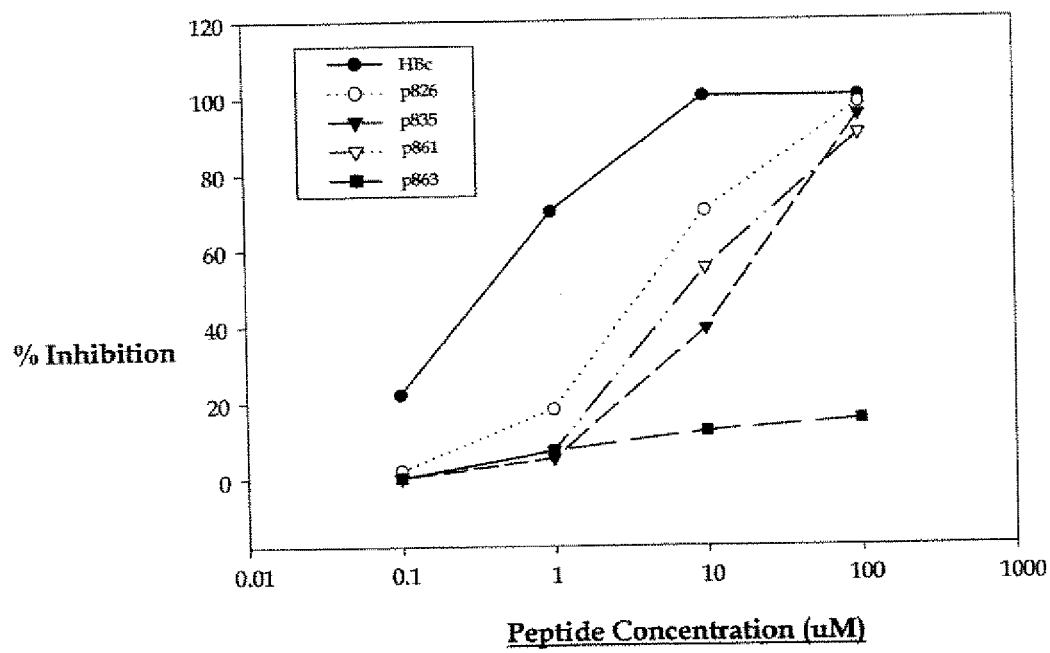

FIG. 10: This figure show CTL activity generated to ten (10) peptides loaded, in combination, to Drosophila cells, FIG. 11: This figure shows the peptide binding capacity of the HER-2 peptides (826, 835, 861 and 863) on the *Drosophila* cells transfected with the human HLA-A2.1 class I molecule.

Figure 12:
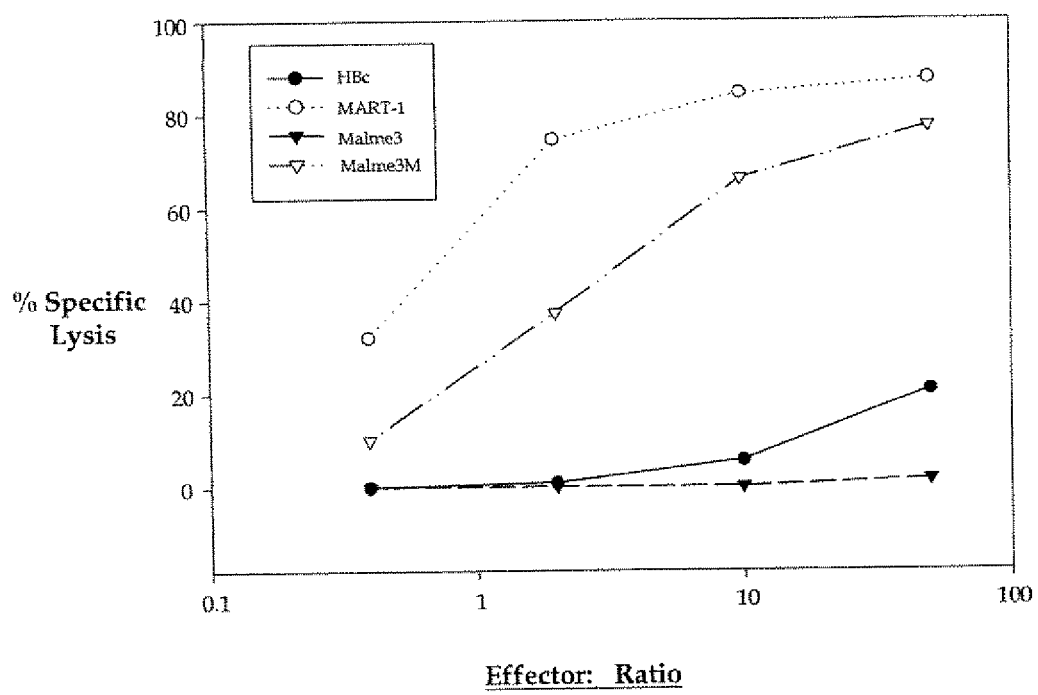

FIG. 12 This figure demonstrates the anti-peptide and anti-tumor response for MART-1 specific effector cells. T2 cells were loaded with MART-1 peptide or a negative control (HBc). Malme3M is a melanoma line, Malme3 is a non-tumor cell line.

Figure 13:
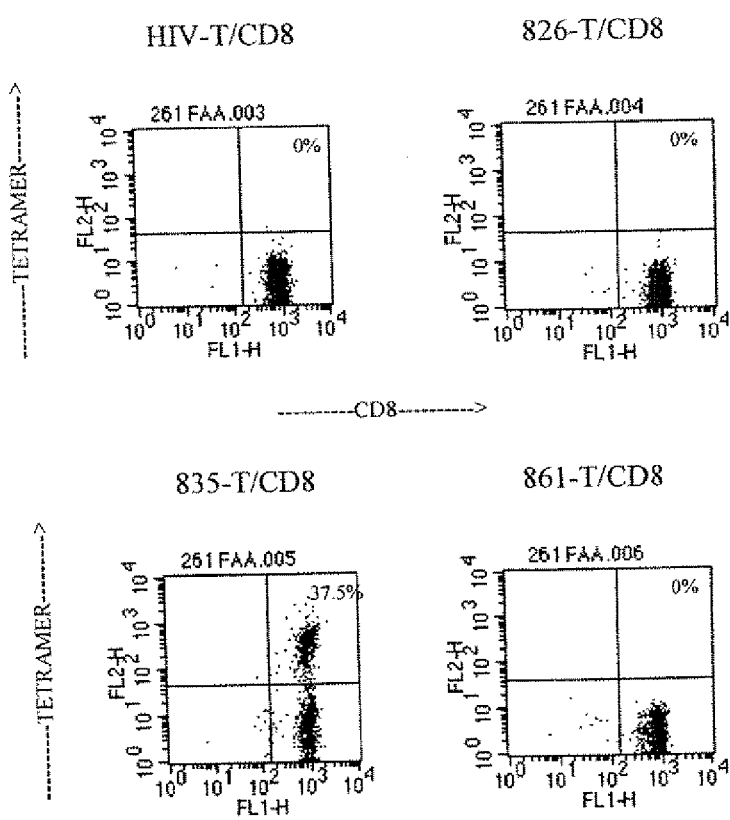
Figure 13:
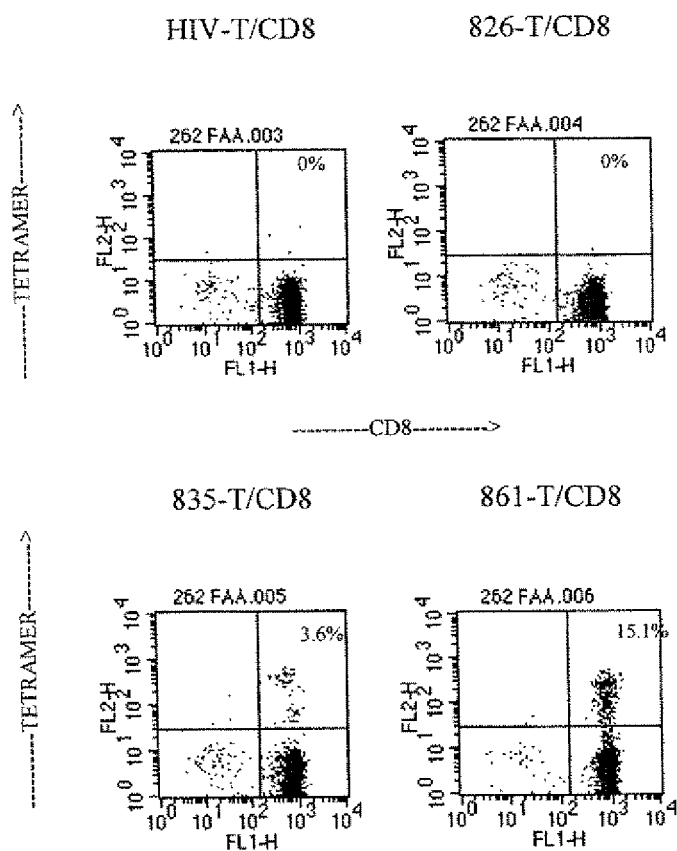

FIG. 13, Panels A and B: This figure shows the tetrameric staining of the HER-2 specific CD8 effector cells from two different donors.

Figure 14:
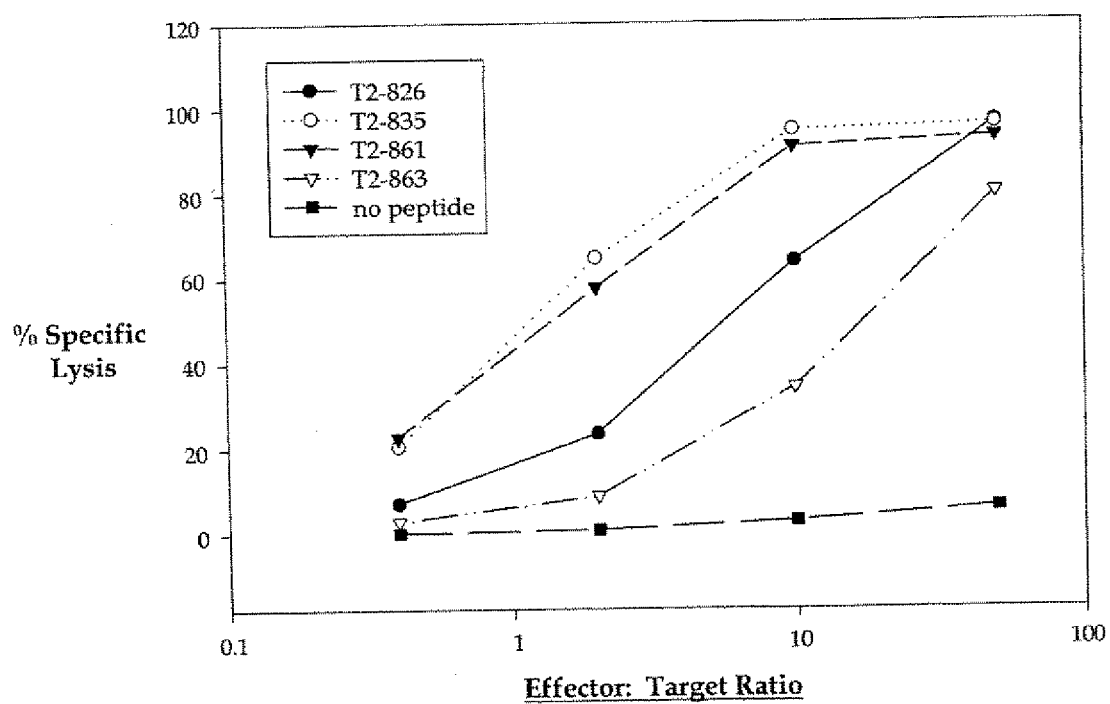

FIG. 14: This figure reveals the anti-peptide response for the HER-2 effector cells evaluated on peptide-loaded T2 cells.

FIG. 15, Panels, A, B, C, D: This figure demonstrates the enhanced killing of an ovarian tumor cell line (HTB-77) when transfected with HLA-A2.1.

Figure 16:
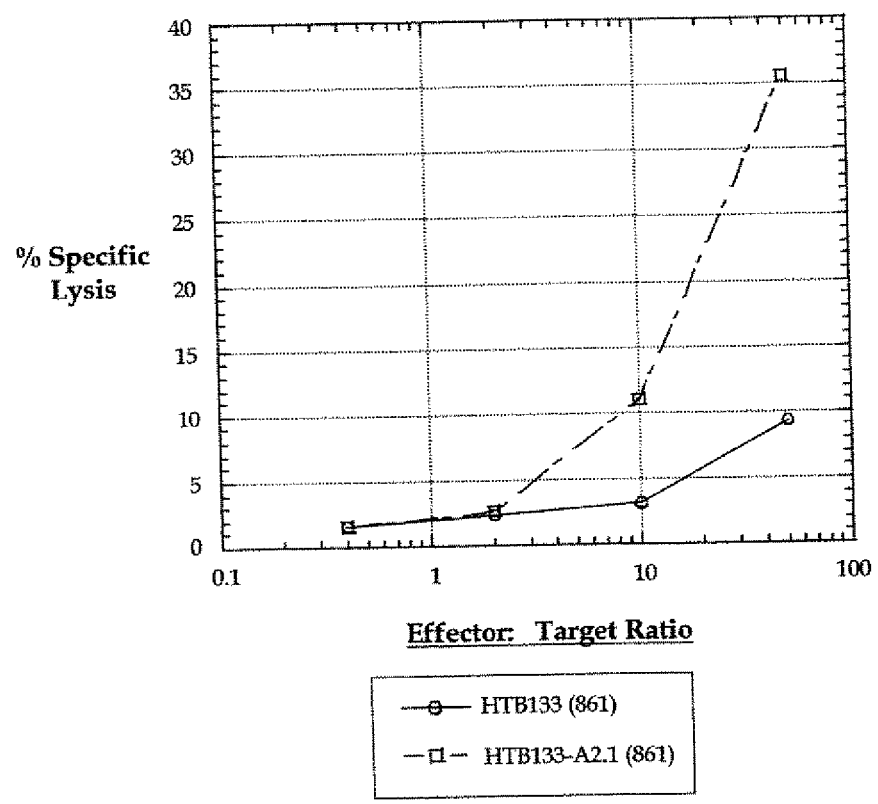

FIG. 16: This figure shows the enhanced killing of a breast cancer cell line (HTB-133) when transfected with HLA-A2.1

Figure 17:
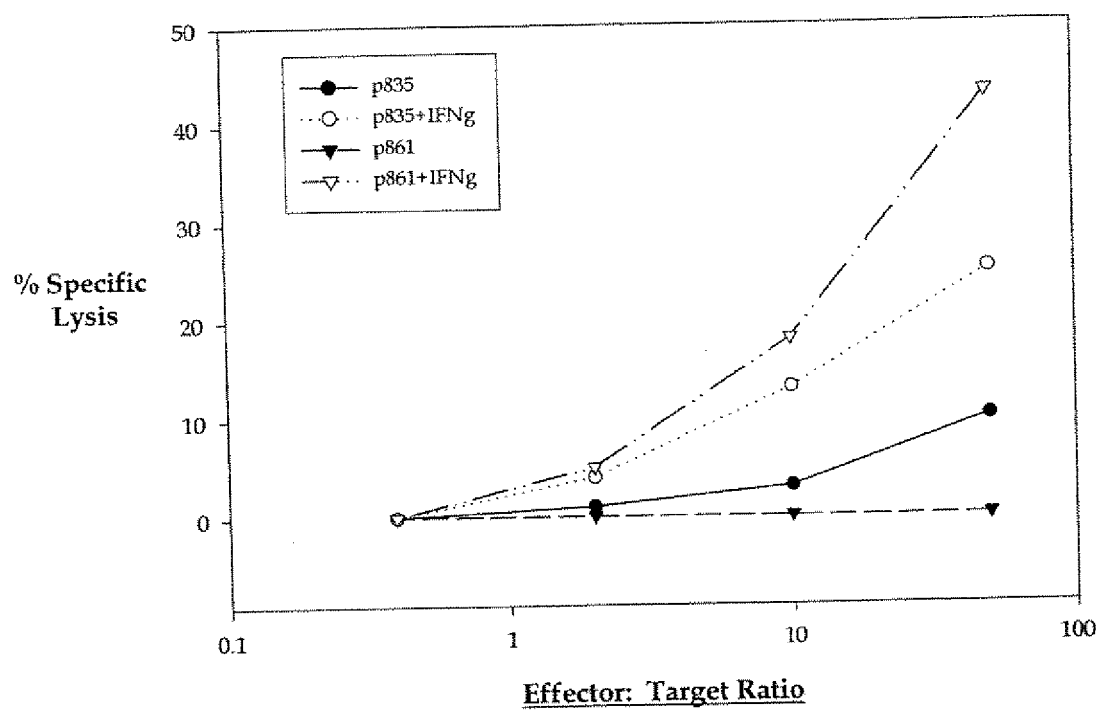

FIG. 17: This figure shows that IFNγ pre-treatment is required to demonstrate lysis of the tumor cell line HTB-77/A2.1.

FIG. 18, Panels A and B: This graph demonstrates that the surface expression of HLA-A2 and HER-2 is unaffected by IFNγ induction in the two cell lines (HTB-77 and HTB-77/A2.1).

Figure 19:
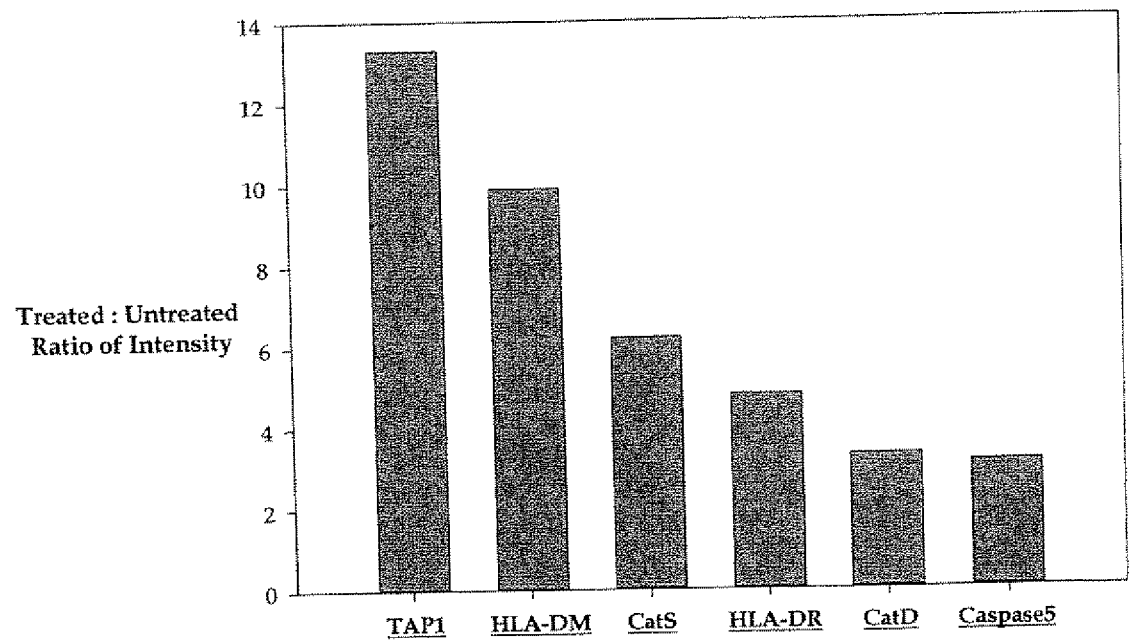

FIG. 19: This graph shows which protein mRNA levels are elevated in the HTB-77/A2.1 cells after an induction with IFNγ.

Figure 20:
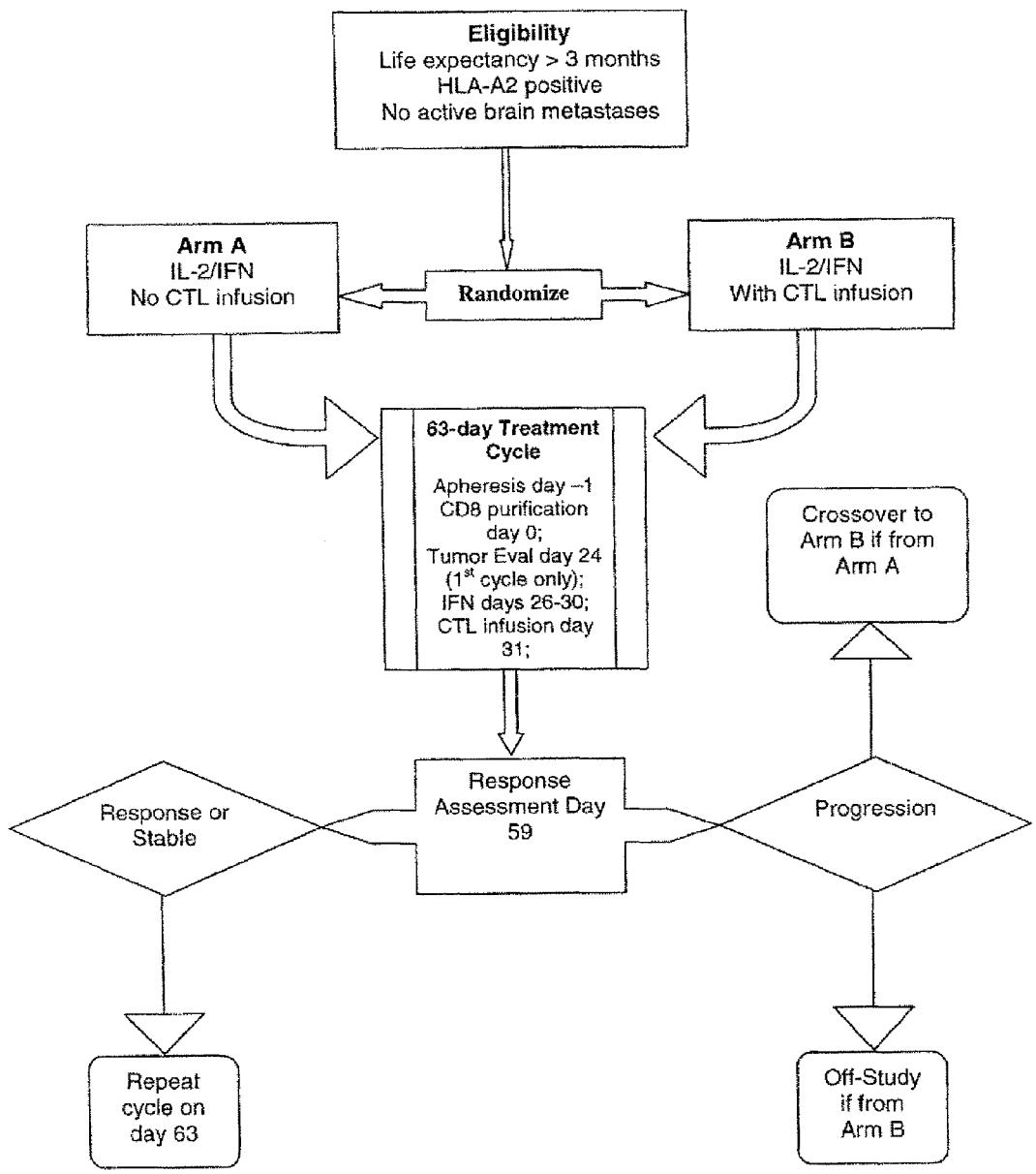

FIG. 20: This graph shows the experimental outline of clinical study CTL-03.

FIG. 21: A) shows in vitro growth curve of CTL cells isolated from a patient (15-RT) under clinical study CTL-02. The cells were isolated from the patient on day 0 of each of the three treatment cycles starting on: Sep. 28, 1999 (15-RT-1), Nov. 22, 1999 (15-RT-2), and Feb. 15, 1999 (15-RT-3), and were cultured in vitro.

B) shows in vitro growth curve of CTL cells isolated from a patient (01-KN) under clinical study CTL-03. The cells were isolated from the patient on day 0 of each of the three treatment cycles starting on: Oct. 30, 2000 (01-KN-1), Jan. 30, 2001 (01-KN-2), and Apr. 9, 2001 (01-KN-3), and were cultured in vitro.

Figure 22:
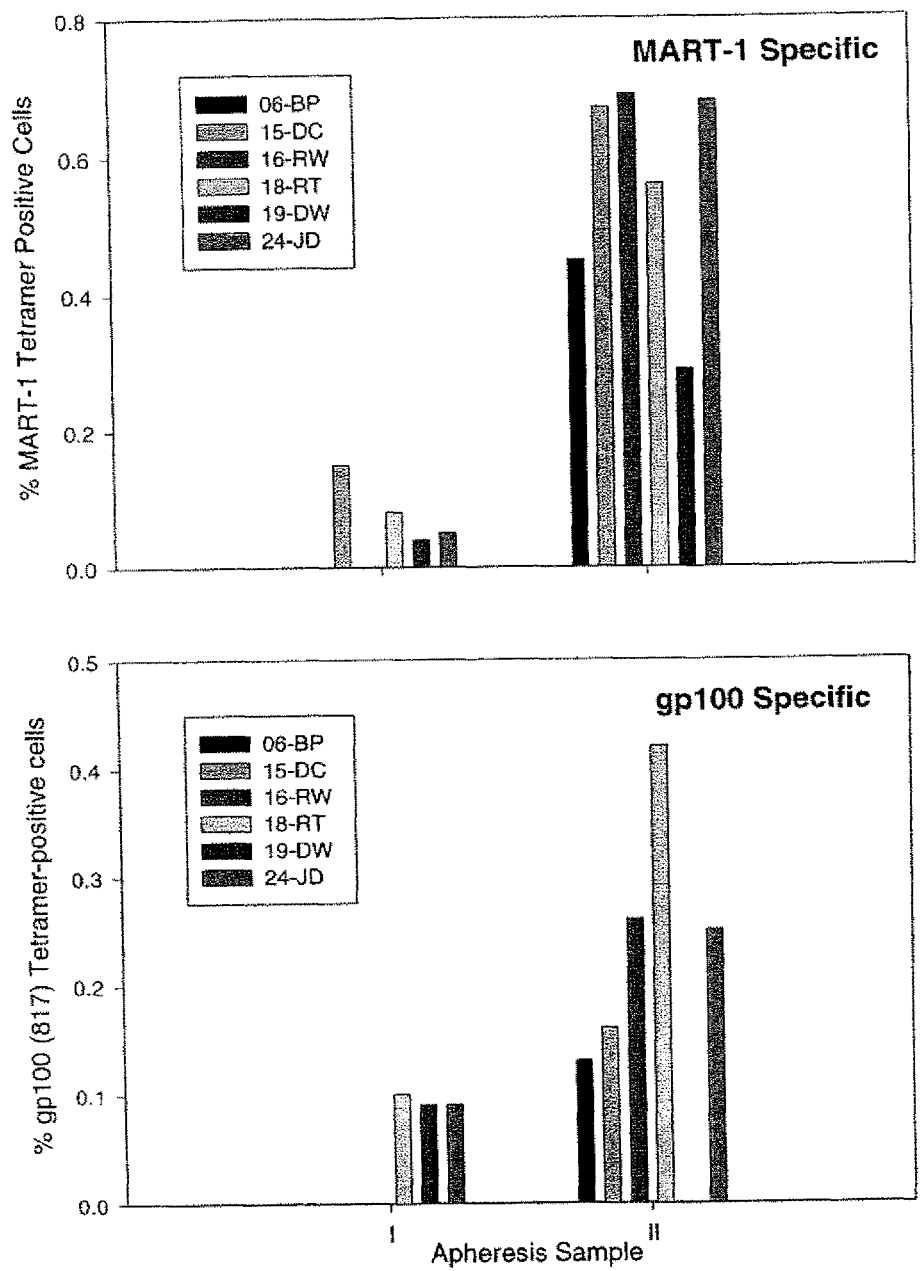

FIG. 22: This figure shows that the number of melanoma antigen-specific T cells increased in the patient after one cycle of treatment in study CTL-03. HLA-A2.1 tetrameric molecules prepared with either gp100 or MART-1 peptides were used to monitor the presence of antigen-specific T cells in purified CD8+ preparations obtained from the leukapheresis samples. The percent (%) of tetramer-positive cells was recorded at the time of the first (I) and second (II) leukapheresis sample, which could be as much as two (2) months apart.

Figure 23:
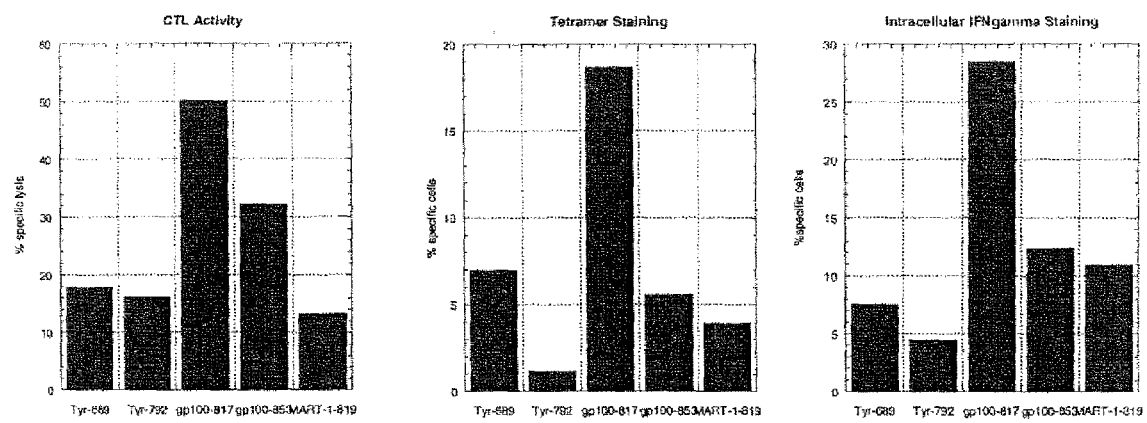

FIG. 23 This figure shows the correlation among three different in vitro assays used to measure cytolytic activity, antigen-specificity and cell proliferation of CTLs. Three different assays were performed on all of the CD8+ CTL preparations at the end of the ex vivo stimulation protocol (CTL-03). All three assays are generally in agreement for determining the makeup of the final bulk culture. In this particular preparation the majority of the T cells in the product were directed to gp100 peptide (817). CTL activity defines the cytolytic and effector function of the cells. Tetramer staining determines the frequency of the antigen-specific cells and intracellular 1N-gamma staining reflects the ability of the T cells to respond to a particular peptide.

Figure 24:
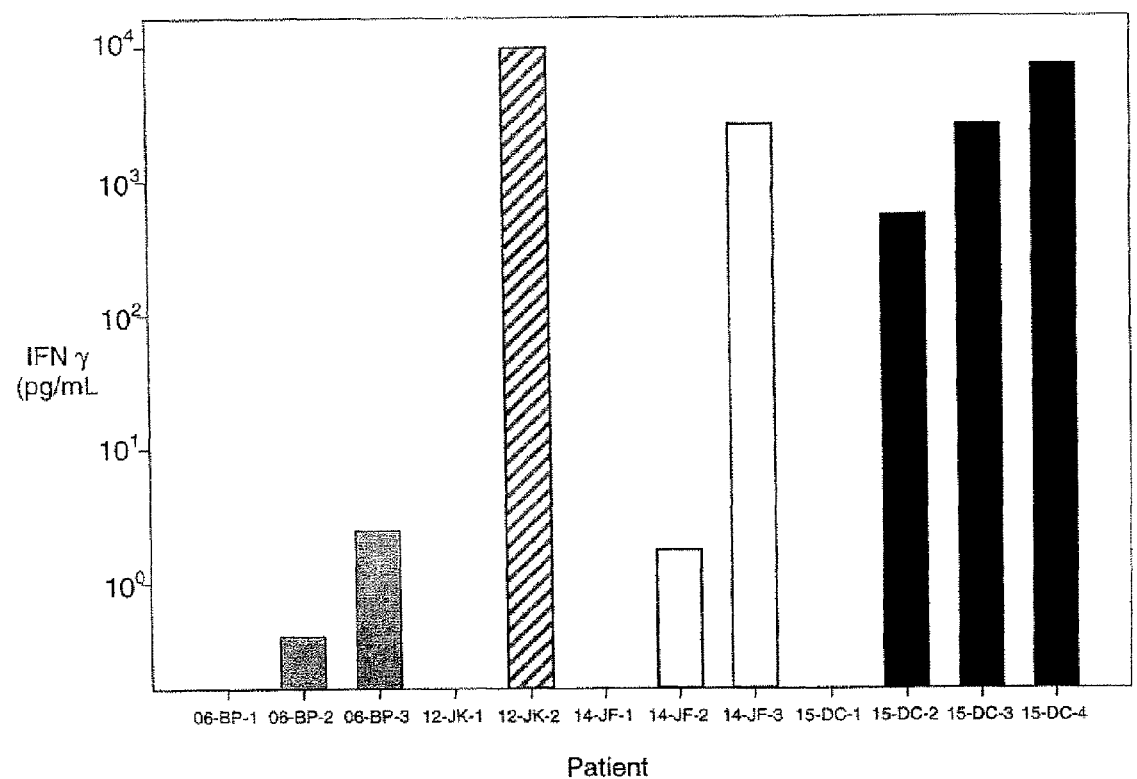

FIG. 24 This figure shows an increase in the amount of interferon gamma at the same time point of the cycle with each repeat cycle of treatment in study CTL-03, suggesting the presence of memory T cells at the same time point of the cycle. Interferon gamma was measured in the supernatant of the ex vivo cultures six (6) days following the primary stimulation with the *Drosophila* cells.

Figure 25:
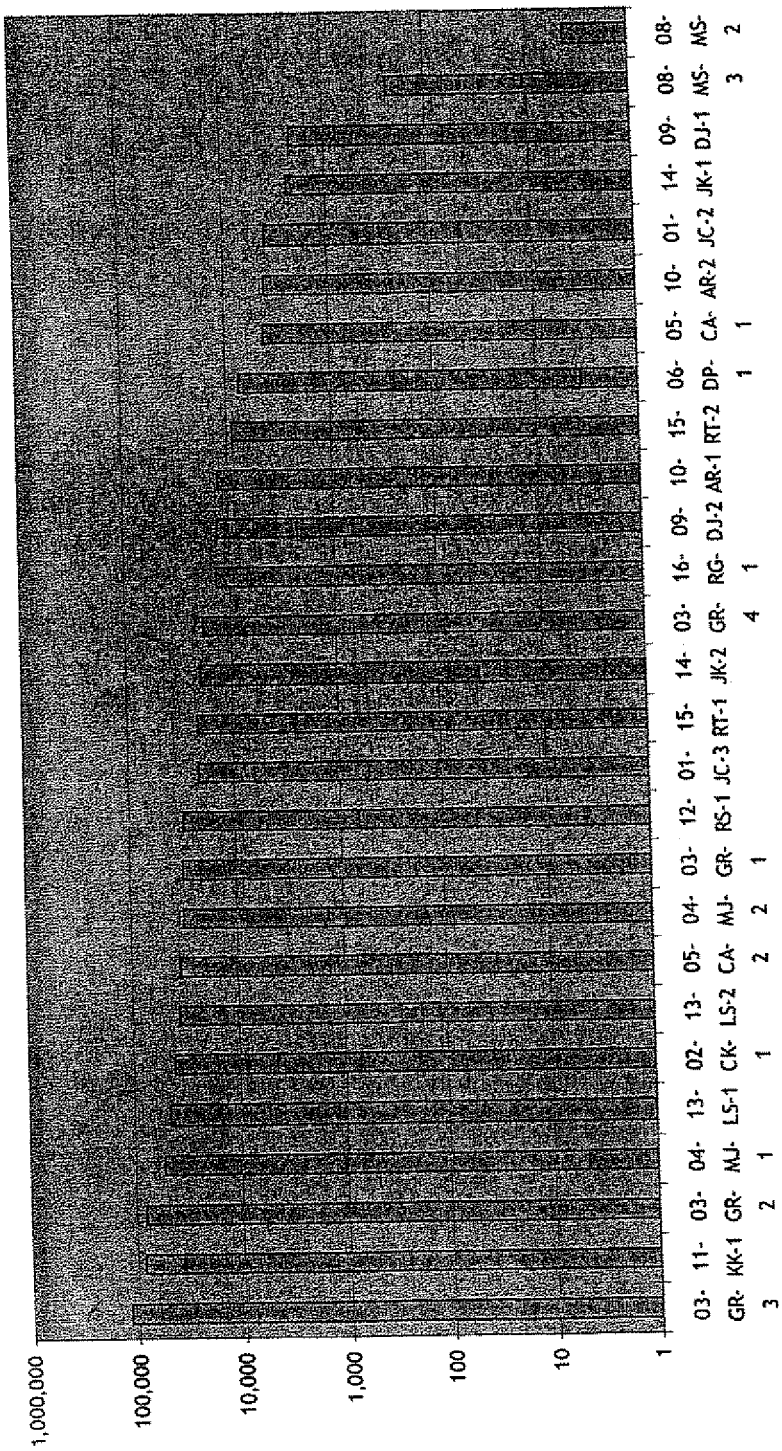

FIG. 25 This figure illustrates the number of cycles and doses of cells administered to each patient in the clinical study described in Example 2. The potency of each dose was calculated by multiplying the number of CD8+ cells by the lytic units recorded for the lysis of a combination of the peptides loaded on the target cells.

DETAILED DESCRIPTION OF THE INVENTION

The present invention provides a method for treating a subject with cancer comprising:
a. preparing a non-naturally occurring antigen-presenting cell line (nnAPC), wherein said nnAPC is capable of presenting up to about fifteen different peptide molecules that is associated with cancer, preferably about ten different peptide molecules, simultaneously where each peptide is about six to twelve amino acids in length, preferably about eight to ten amino acids in length and in a concentration range of about 10 nM to 100 μM;
b. harvesting CD8+ cells from said subject or a suitable donor;
c. stimulating said CD8+ cells with said nnAPC cell line;
d. adding said CD8+ cells to media that contains a cytokine, such as, IL-2, IL-7 or conditioned growth medium (CGM), preferably, IL-2, or IL-2 and IL-7 in combination;
e. mixing unsuspended peripheral blood monocytes, or alternatively, CD-8 depleted peripheral blood monocytes collected from said subject or a suitable donor with about 5 to 50 μg/ml of a peptide;
f. irradiating said peripheral blood monocyte suspension with a sufficient dose of γ-radiation necessary to prevent proliferation of these cells in the suspension, such as a dose in the range of about 3,000 to 7,000 rads, preferably about 5,000 rads, alternatively, the peripheral blood lymphocyte suspension may be treated with cytostatic agents including, but not limited to, mitomycin C;
g. isolating adherent peripheral blood monocytes;
h. loading said adherent peripheral blood monocytes with about 5 μg/ml to 50 μg/ml of each of said peptide;
i. combining said CD8+ cells with said adherent peripheral blood monocytes at a ratio of about ten CD8+ cells to one peripheral blood monocyte;
j. optionally stimulating said combined suspension of CD8+ cells and peripheral blood monocytes for about six to nine days;
k. optionally stimulating said suspension of CD8$^+$ cells and peripheral blood monocytes with IL-2 and IL-7 in media;
l. optionally assaying CD8+ suspension for suitable CTL activity, and optionally assaying for CTL purity, sterility and endotoxin content; and
m. inoculating said subject with said CD8+ suspension.

Another embodiment of the present invention provides a method for treating a subject with cancer comprising:
a. preparing a non-naturally occurring antigen-presenting cell line (nnAPC), wherein said nnAPC is capable of presenting up to about fifteen different peptide molecules that is associated with cancer, preferably about ten peptides, simultaneously where each peptide is eight to ten amino acids in length;
b. harvesting CD8$^+$ cells from said subject;
c. stimulating said CD8$^+$ cells with said nnAPC cell line for about six to nine days;
d. stimulating said CD8$^+$ cells with IL-2 and IL-7 in media;
e. mixing peripheral blood monocytes collected from said subject with about 10 µg/ml of each peptide;
f. irradiating said CD8-depleted peripheral blood monocyte suspension with about 5,000 rads of γ-radiation;
g. isolating adherent peripheral blood monocytes;
h. loading said adherent peripheral blood monocytes with about 10 ug/ml of said epitope;
i. combining said CD8+ cells with said adherent peripheral blood monocytes at a ratio of about ten CD8+ cells to one peripheral blood monocyte;
j. stimulating said combined suspension of CD8$^+$ cells and peripheral blood monocytes for about six to nine days;
k. stimulating said suspension of CD8$^+$ cells and peripheral blood monocytes with IL-2 and IL-7 in media;
l. assaying said CD8$^+$ suspension for suitable CTL activity, purity, sterility and endotoxin content; and
m. inoculating said subject with CD8$^+$ suspension.

Another embodiment of the present invention provides a method for treating a subject with melanoma comprising:
a. preparing a non-naturally occurring antigen-presenting cell line(nnAPC), wherein said nnAPC is capable of presenting up to about fifteen different peptide molecules that is associated with melanoma, preferably about ten peptides, simultaneously where each peptide is eight to ten amino acids in length;
b. harvesting CD8$^+$ cells from said subject,
c. stimulating said CD8$^+$ cells with said nnAPC cell line for about six to nine days;
d. stimulating said CD8$^+$ cells with IL-2 and IL-7 in media;
e. mixing peripheral blood monocytes collected from said subject with about 20 µg/ml of each peptide said nnAPC can present;
f. irradiating said CD8-depleted peripheral blood monocyte suspension with about 5,000 rads of γ-radiation;
g. isolating adherent peripheral blood monocytes;
h. loading said adherent peripheral blood monocytes with about 10 ug/ml of said epitope;
i. combining said CD8+ cells with said adherent peripheral blood monocytes at a ratio of about ten CD8+ cells to one peripheral blood monocyte;
j. stimulating said combined suspension of CD8$^+$ cells and peripheral blood monocytes for about six to nine days;
k. stimulating said suspension of CD8$^+$ cells and peripheral blood monocytes with IL-2 and IL-7 in media;
l. assaying CD8$^+$ suspension for suitable CTL activity, purity, sterility and endotoxin content; and
m. inoculating said subject with CD8$^+$ suspension.

Another embodiment of the present invention is a method of treating melanoma wherein the nnAPC presents the following peptides, Tyrosinase$_{369-377}$, Tyrosinase$_{207-216}$, gp100$_{209-217}$, gp100$_{154-162}$, MART-1$_{27-35}$, HER-2/neu$_{789-797}$, HER-2/neu$_{369-377}$, C-lectin$_{8-16}$, Pec60$_{20-29}$, and Pec60$_{25-33}$.

Another embodiment of the present invention is a method of treating a disease or disease condition that results in an insufficient or inadequate immune response that is normally associated with Class I HLA molecules, wherein the treatment eliminates infected or transformed cells.

Another embodiment of the present invention is a method of treating a disease or disease condition that results in an insufficient or inadequate immune response that is normally associated with Class I HLA molecules, wherein infected or transformed cells that have been shown to be susceptible to elimination by CTL are treated by the method comprising:
a. preparing a non-naturally occurring antigen-presenting cell line (nnAPC), wherein said nnAPC is capable of presenting up to about fifteen different peptide molecules associated with said disease or disease condition, preferably about ten different peptide molecules, simultaneously where each peptide is about six to twelve amino acids in length, preferably about eight to ten amino acids in length and in a concentration range of about 10 nM to 100 µm;
b. harvesting CD8$^+$ cells from said subject or a suitable donor;
c. stimulating said CD8$^+$ cells with said nnAPC cell line;
d. adding said CD8$^+$ cells to media that contains a cytokine, such as, IL-2, IL-7 or CGM, preferably, IL-2, or IL-2 and IL-7 in combination;
e. mixing unsuspended peripheral blood monocytes, or alternatively, CD-8 depleted peripheral blood monocytes collected from said subject or a suitable donor with about 5 to 50 µg/ml of a peptide;
f. irradiating said peripheral blood monocyte suspension with a sufficient dose of γ-radiation necessary to prevent proliferation while maintaining the stimulation capacity of the peripheral blood monocytes, such as a dose in the range of about 3,000 to 7,000 rads, preferably about 5,000 rads;
g. isolating adherent peripheral blood monocytes;
h. loading said adherent peripheral blood monocytes with about 5 µg/ml to 50 µg/ml of said each peptide;
i. combining said CD8$^+$ cells with said adherent peripheral blood monocytes at a ratio of about ten CD8$^+$ cells to one peripheral blood monocyte;
j. optionally stimulating said combined suspension of CD8$^+$ cells and peripheral blood monocytes for about six to nine days;
k. optionally stimulating said suspension of CD8$^+$ cells and peripheral blood monocytes with IL-2 and IL-7 in media;
l. optionally assaying the CD8$^+$ suspension for suitable CTL activity, and optionally assaying for CTL purity, sterility and endotoxin content; and
m. inoculating said subject with the CD8$^+$ suspension.

The present invention provides a non-naturally occurring antigen-presenting cell (nnPC) derived from *Drosophila melanogaster* cells transfected with DNA encoding human class I HLA, binding, and co-stimulatory molecules for expression, wherein the nnAPC is capable of presenting up to fifteen different peptide molecules, preferably ten peptide molecules.

Another embodiment of the present invention provides an nnAPC that presents peptides that are associated with various desired functions that enhance the treatment of the subject.

For example, in addition to peptides associated with the disease or disease condition being treated, the nnAPC can express proteins associated with accessory molecules such as, lymphocyte function antigens (LFA-1, LFA-2 and LFA-3), intercellular adhesion molecules 1 and 2 (ICAM-1, ICAM-2), T-cell co-stimulatory factors (CD40, CD70, B7) enhance cell-cell adhesion or transduce additional cell activation signals.

Another embodiment of the present invention provides an nnAPC that presents peptides that are associated with several types of cancers. For example, the peptides associated or derived from a breast cancer related polypeptide, such as, HER-2/neu, may be presented with peptides associated or derived from a melanoma related polypeptide, such as, MART-1, or MAGE.

Another embodiment of the present invention provides a method for manufacturing non-naturally occurring antigen-presenting cell (nnAPC) capable of presenting up to ten different peptide molecules simultaneously, said method comprising of the step:

a. preparing an insect cell line from *Drosophila melanogaster* eggs; alternatively preparing an insect cell line for expressing human MHC Class I molecules and costimulatory adhesion molecules;

b. growing said insect cells in a media that is suitable for growing insect cells, preferably Schneider™'s *Drosophila* Medium;

c. making a pRmHa-3 plasmid from a pRmHa-1 expression vector, where said pRmHa-3 plasmid includes a metallothionein promoter, metal response consensus sequences and an alcohol dehydrogenase gene bearing a polyadenylation signal isolated from *Drosophila melanogaster*;

d. inserting into said pRmHa-3 plasmid complementary DNA for human class I HLA A2.1, B7.1, B7.2, ICAM-1, β-2 microglobulin and LFA-3, wherein A2.1 can be substituted with any human class I DNA sequence;

e. transfecting said insect cells with a phshneo plasmid and said pRmHa-3 plasmid containing complementary DNA; and, f. creating nnAPC by contacting said insect cells with CuSO$_4$ to induce expression of the transfected genes in said insect cells.

The insect cells of the present invention are grown in a media suitable for growing insect cells, hereinafter referenced to as "insect growth media". Insect growth media are commercially available from a number of vendors, such as, Schneider's *Drosophila* Medium, Grace's Insect Media, and TC-100 Insect Media. Alternatively, insect growth media can be prepared by one of ordinary skill in the art. Typically the media will include components necessary to promote and sustain the growth of insects cells, such as, inorganic salts (for example, calcium chloride, magnesium sulfate, potassium chloride, potassium phosphate, sodium bicarbonate, sodium chloride, and sodium phosphate), amino acids various carbohydrate and chemical species (Imogene Schneider, *Exp. Zool.* (1964) 156(1): pg. 91). Alternatively, the media can also include vitamins, minerals, and other components that aid in the growth of insect cells.

The present invention further provides a method for treating a subject with cancer, comprising the steps of:

a) administering to said subject an effective amount of interferon-alfa that is capable of enhancing the expression of tumor antigen and HLA class I molecules on the surface of the tumor; and b) inoculating said subject with an effective amount of autologous cytotoxic T lymphocytes with specificity for cancer-associated target antigens.

In a preferred embodiment, the method of treatment further comprises a step of administering to said subject an effective amount of interleukin-2 that is capable of enhancing the in vivo maintenance of the autologous cytotoxic T lymphocytes with specificity for melanoma-associated target antigen.

Following is a list of abbreviations and definitions used in the present specification.

| Abbreviations | |
|---|---|
| APC | Antigen-presenting cells |
| CD8$^+$ | CD8$^+$ T cells |
| CTL | Cytotoxic T lymphocyte |
| E | Effector |
| Fas | Also known as CD95, epitope on T cells |
| ICAM | Intercellular adhesion molecule |
| IL | Interleukin |
| LAK | Lymphokine-activated killer cells |
| LFA | Lymphocyte function antigens |
| MHC | Major histocompatibility complex |
| nnAPC | non-naturally occurring antigen-presenting cell |
| NP | Nuclear protein |
| PBMC | Peripheral blood mononuclear cell |
| PBS | Phosphate-buffered saline |
| PCR | Polymerase chain reaction |
| RPMI | Roswell Park Memorial Institute |
| RWJPRI | The R.W. Johnson Pharmaceutical Research Institute |
| T | Target |
| TCR | T cell antigen receptor |
| TIL | Tumor-infiltrating lymphocytes |

Following is a list of abbreviations used in the present specification for various peptide epitopes. The individual amino acid residues are identified according to a single letter code that is readily known and used by those of ordinary skill in the art.

| Amino Acid | Abbreviations | |
|---|---|---|
| | 3-Letter | 1-Letter |
| alanine | ala | A |
| valine | val | V |
| leucine | leu | L |
| isoleucine | ile | I |
| proline | pro | P |
| phenylalanine | phe | F |
| trytophan | tyr | W |
| methionine | met | M |
| glycine | gly | G |
| serine | ser | S |
| threonine | thr | T |
| cysteine | cys | C |
| tyrosine | tyr | Y |
| asparagine | asn | N |
| glutamine | gln | Q |
| aspartic acid | asp | D |
| glutamic acid | glu | E |
| lysine | lys | K |
| arginine | arg | R |
| histidine | his | H |

Peptide Epitome Abbreviations

As used herein the term "tyrosinase 369-377" or "tyrosinase$_{369-377}$" refers to the amino acid sequence YMNGTMSQV (SEQ ID NO: 1). Also included within this definition is the peptide of the sequence YMDGTMSQV (SEQ ID NO: 2), which results from a post-translational event that modifies the amino acid residue "N" of sequence YMNGTMSQV (SEQ ID NO: 1) to "D" resulting in the amino acid sequence of YMDGTMSQV (SEQ ID NO: 2) (Skipper et al, *J. Exp. Med.* (1996) 183:527-534).

As used herein the term "tyrosinase 207-216" or "tyrosinase$_{207-216}$" refers to the amino acid sequence FLPWHRLFLL (SEQ ID NO: 3).

As used herein the term "gp100 209-217" or "gp100$_{209-217}$" refers to the amino acid sequence ITDQVPFSV (SEQ ID NO: 4).

As used herein the term "gp100 154-162" or "gp100$_{154-162}$" refers to the amino acid sequence KTWGQYWQV (SEQ ID NO: 5).

As used herein the term "MART-1 27-35" or "MART-1$_{27-35}$" refers to the amino acid sequence AAGIGILTV (SEQ ID NO: 6).

As used herein the term "HER-2/neu 789-797" or "HER-2/neu$_{789-797}$" refers to the amino acid sequence CLTSTVQLV (SEQ ID NO: 7).

As used herein the term "HER-2/neu 369-377" or "HER-2/neu$_{369-377}$" refers to the amino acid sequence KIFGSLAFL (SEQ ID NO: 8).

As used herein the term "C-lectin 8-16" or "C-lectin$_{8-16}$" refers to the amino acid sequence KMASRSMRL (SEQ ID NO: 9).

As used herein the term "Pec60 20-29" or "Pec60$_{20-29}$" refers to the amino acid sequence ALALAALLVV (SEQ ID NO: 10).

As used herein the term "Pec60 25-33" or "Pec60$_{25-33}$" refers to the amino acid sequence ALLVVDREV (SEQ ID NO: 11).

As used herein, the term "CD8 peptide 59-70" or "CD8 peptide$_{59-70}$" refers to the amino acid sequence of AAEGLDTQRFSG (SEQ ID NO: 12).

Terms and Definitions

As used herein, the term "adoptive immunotherapy" refers the administration of donor or autologous T lymphocytes for the treatment of a disease or disease condition, wherein the disease or disease condition results in an insufficient or inadequate immune response that is normally associated with Class I HLA molecules. Adoptive immunotherapy is an appropriate treatment for any disease or disease condition where the elimination of infected or transformed cells has been demonstrated to be achieved by CTLs. For example, disease or disease conditions include but are not limited to cancer and/or tumors, such as, melanoma, prostate, breast, colorectal stomach, throat and neck, pancreatic, cervical, ovarian, bone, leukemia and lung cancer; viral infections, such as, hepatitis B, hepatitis C, human immunodeficiency virus; bacterial infections, such as tuberculosis, leprosy and listeriosis, and parasitic infections such as malaria.

As used herein, the terms "B7.1, B7.2" refers to co-stimulatory molecules associated with antigen-presenting cells.

As used herein, the term "BCNU" refers to carmustine, also known as, 1,3-bis(2-chloroethyl)-1-nitrosourea.

As used herein, the term "BSE" refers to bovine spongiform encephalitis.

As used herein, the term "CD" refers to clusters of differentiation, T lymphocytes (originally), B lymphocytes, monocytes, macrophages, and granulocytes grouped by antigen epitopes and function.

As used herein, the term "DTIC" refers to dacarbazine, 5-(3,3-dimethyl-1-triazeno)-imidazole-4-carboxamide.

As used herein, the term "ex vivo" or "ex vivo therapy" refers to a therapy where biological materials, typically cells, are obtained from a patient or a suitable alternate source, such as, a suitable donor, and are modified, such that the modified cells can be used to treat a pathological condition which will be improved by the long-term or constant delivery of the therapeutic benefit produced by the modified cells. Treatment includes the re-introduction of the modified biological materials, obtained from either the patient or from the alternate source, into the patient. A benefit of ex vivo therapy is the ability to provide the patient the benefit of the treatment without exposing the patient to undesired collateral effects from the treatment. For example, high doses of cytokines are often administered to patients with cancer or viral infections to stimulate expansion of the patient's CTLs. However, cytokines often cause the onset of flu like symptoms in the patients. In an ex vivo procedure, cytokines are used to stimulate expansion of the CTLs outside of the patient's body, and the patient is spared the exposure and the consequent side effects of the cytokines. Alternatively under suitable situations, or conditions, where appropriate and where the subject can derive benefit, the subject can be treated concurrently with low level dosages of γ interferon, α interferon and/or IL-2. The expected effect of the interferons is to possibly sensitize the tumor cells to lysis by antigen specific CTL, and the effect of the IL-2 is to possibly enhance antigen specific CTL persistence.

As used herein, the term "HEPES" refers to N-2-hydroxyethylpiperazine-N'2-ethanesulfonic acid buffer.

As used herein, the term "HLA-A2.1" refers to a HLA Class I molecule found in approximately 45% of Caucasians.

Figure 1:
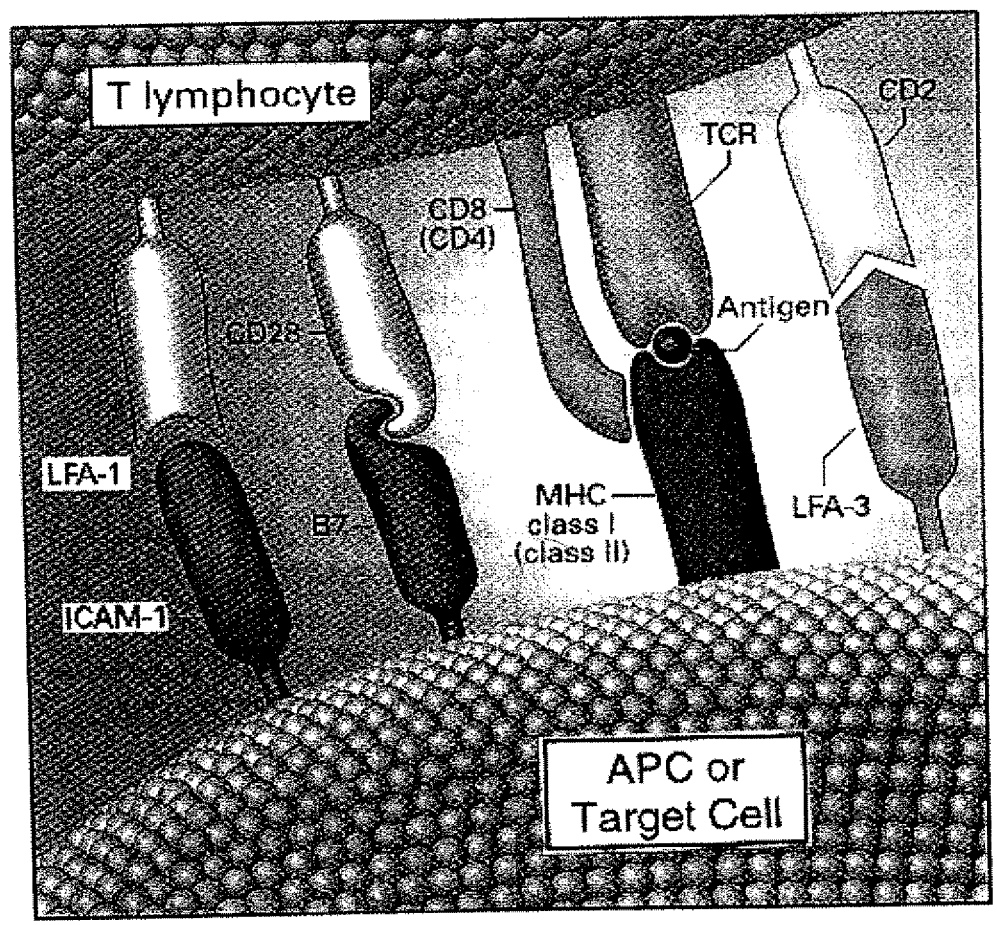
FIG. 1: This figure is a graphic depiction of the interaction between CD8+ cells, also known as cytotoxic T lymphocytes, with antigen-presenting cells or target cells, in this case tumor cells.

As used herein, the term "MART-1" or "(melanoma antigen recognized by T-Cells-1" refers to a melanoma-associated antigen. The amino acid and nucleic acid sequences, as well as various characteristics of this antigen are disclosed in U.S. Pat. No. 5,994,523, issued Nov. 30, 1999 entitled "*Melanoma Antigens and Their Use in Diagnostic and Therapeutic Methods*"; U.S. Pat. No. 5,874,560, issued Feb. 23, 1999 entitled "Melanoma Antigens and Their Use in Diagnostic and Therapeutic Methods"; and U.S. Pat. No. 5,844,075, issued Dec. 1, 1998 entitled "*Melanoma Antigens and heir Use in Diagnostic and Therapeutic Methods.*" In particular, U.S. Pat. No. 5,994,523 discloses full length nucleic acid and amino acid sequences of MART-1 in FIG. 1 as SEQ ID NO: 1, and SEQ ID NO: 2, respectively. The aforementioned FIG. 1 is herein incorporated by reference.

As used herein, the term "MAGE" refers to a melanoma-associated antigen. The amino acid and nucleic acid sequences, as well as various characteristics of this antigen are disclosed in U.S. Pat. No. 6,140,050, issued Oct. 31, 2000 entitled "*Methods for Determining Breast Cancer and Melanoma by Assaying for a Plurality of Antigens Associated Therewith*"; U.S. Pat. No. 5,759,783, issued Jun. 2, 1998 entitled "*Method of Screening for Cancer by Detecting Messenger RNA for a MAGE-XP Gene*"; and U.S. Pat. No. 5,662,907, issued Sep. 2, 1997 entitled "*Induction of Anti-Tumor Cytotoxic T Lymphocytes in Humans Using Synthetic Peptide Epitopes.*"

As used herein, the term "MPC-10" refers to a magnetic particle concentrator.

As used herein, the term "NK cells" refers to natural killer cells.

As used herein, the term "OKT3" refers to ORTHOCLONE OKT3, muromonab-CD3, anti-CD3 monoclonal antibody.

As used herein, the term "TAP-1,2" refers to Transporter Associated with Antigen Processing-1,2.

As used herein, the term "Th cells" refers to Helper T cells, CD4+.

As used herein, the term, "tyrosinase" refers to a protein associated with melanoma (Brichard et al., *J. Exp. Med.* (1993) 178:489-495; Robbins et al., *Cancer Res.* (1994) 54: 3124-3126). U.S. Pat. No. 5,843,648, issued Dec. 1, 1998 entitled "*P15 and Tyrosinase Melanoma Antigens and Their Use in Diagnostic and Therapeutic Methods*" discloses antigenic peptides and associated polynucleic acids related to tyrosinase in FIG. 7, Panels A to D, the aforementioned figure incorporated herein by reference. U.S. Pat. No. 5,487,974, issued Jan. 30, 1996 entitled "*Method for Detecting Complexes Containing Human Leukocyte Antigen A2 (HLA-A2) Molecules and a Tyrosinase Derived Peptide on Abnormal Cells*" discloses an additional peptide that is associated with tyrosinase and melanoma in Example 9, at Table 3, the aforementioned incorporated herein by reference.

As used herein, the term "gp100" refers to a melanoma antigen recognized by tumor infiltrating lymphocytes (TIL). The TIL which recognize gp100 is associated with in vivo tumor rejection (Bakker et al., *J. Exp. Med.* (1994) 179:1005-1009; Kawakarn et al., *J. Immunol.* (1995) 154:3961-3968). Antigenic peptides related to gp100 are disclosed in U.S. Pat. No. 5,994,523, issued Nov. 30, 1999 entitled "*Melanoma Antigens and Their Use in Diagnostic and Therapeutic Methods*"; U.S. Pat. No. 5,874,560, issued Feb. 23, 1999 entitled "*Melanoma Antigens and Their Use in Diagnostic and Therapeutic Methods*"; and U.S. Pat. No. 5,844,075, issued Dec. 1, 1998 entitled "*Melanoma Antigens and Their Use in Diagnostic and Therapeutic Methods*." In particular, U.S. Pat. No. 5,994,523 discloses nucleic acid and amino acid sequences related to GP100 in FIGS. 4 and 5, respectively. Also disclosed are antigenic peptides derived from the amino acid sequences, including those identified as SEQ ID NOs: 27, 33, 34, 35, 36, 37, 38, 39, 40, and 41. All of the aforementioned FIGS. 4 and 5, and the peptides identified by SEQ ID NOs are herein incorporated by referenced.

As used herein, the term "melanoma" refers to, but is not limited to, melanomas, metastatic melanomas, melanomas derived from either melanocytes or melanocytes related nevus cells, melanosarcornas, melanocarcinomas, melanoepitheliomas, melanoma in situ superficial spreading melanoma, nodular melanoma, lentigo maligna melanoma, acral lentiginous melanoma, invasive melanoma or familial atypical mole and melanoma (FAM-M) syndrome. Such melanomas in mammals may be caused by, chromosomal abnormalities, degenerative growth and developmental disorders, mitogenic agents, ultraviolet radiation (UV), viral infections, inappropriate tissue expression of a gene, alterations in expression of a gene, and presentation on a cell, or carcinogenic agents. The aforementioned melanomas can be diagnosed, assessed or treated by methods described in the present application.

As used herein, the term "C-lectin" refers to a peptide of the sequence that has been found to be associated with ovarian cancer.

As used herein, the term "major histocompatibility complex" or "MHC" is a generic designation meant to encompass the histo-compatibility antigen systems described in different species including the human leucocyte antigens (HLA).

As used herein, the terms "epitope," "peptide epitope," "antigenic peptide" and "immunogenic peptide" refers to a peptide derived from an antigen capable of causing a cellular immune response in a mammal. Such peptides may also be reactive with antibodies from an animal immunized with the peptides. Such peptides may be about five to twenty amino acid in length preferably about eight to fifteen amino acids in length, and most preferably about nine to ten amino acids in length.

As used herein, the term "Pec60" refers to a peptide of the sequence that has been found to be associated with ovarian and breast cancer.

As used herein, the term "analog" includes any polypeptide having an amino acid residue sequence substantially identical to the sequences of the present invention, specifically shown herein in which one or more residues have been conservatively substituted with a functionally similar residue and which displays the functional aspects of the present invention as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid or another.

As used herein, the term "conservative substitution" also includes the use of a chemically derivatized residue in place of a non-derivatized residue.

As used herein, the term "chemical derivative" refers to a subject polypeptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those proteins or peptides, which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Proteins or polypeptides of the present invention also include any polypeptide having one or more additions and/or deletions or residues relative to the sequence of a polypeptide whose sequence is encoded is the corresponding nucleic sequence of the present invention, so long as the requisite activity is maintained.

As used herein, the term "HER-2/neu" refers to an oncogene, which express or over-express, one or more membrane-associated, receptor-like oncogene proteins. Among the cancers which have been found to be associated with expression or over-expression of HER-2/neu are certain breast stomach, ovarian colon and salivary gland cancers. The HER-2/neu oncogene is a member of the tyrosine protein kinase family of oncogenes and shares a high degree of homology with the epidermal growth factor receptor (EGFR). HER-2/neu has been shown to play a role in cell growth and/or differentiation. HER-2/neu appears to induce malignancies through quantitative mechanisms that result from increased or deregulated expression of an essentially normal gene product. U.S. Pat. No. 6,075,122, issued Jun. 13, 2000 entitled "*Immune Reactivity to HER-2/neu Protein for Diagnosis and Treatment of Malignancies in Which the HER-2/neu Oncogene is Associated*" discloses peptides that elicit $CD8^+$ T cell responses at column 12, line 31 to column 13, line 7, identified according to SEQ ID numbers are herein incorporated by reference.

HER-2/neu (p185) is the protein product of the HER-2/neu oncogene. The HER-2/neu gene is amplified and the HER-2/neu protein is over-expressed in a variety of cancers including breast, ovarian, colon, lung and prostate cancer. HER-2/neu is related to malignant transformation. It is found in 50% to 60% of ductal in situ carcinoma and 20% to 40% of all breast cancers, as well as a substantial fraction of adenocarcinomas arising in the ovaries, prostate, colon and lung. HER-2/neu is intimately associated not only with the malignant phenotype, but also with the aggressiveness of the malignancy, being found in one-fourth of all invasive breast cancers. HER-2/neu over-expression is correlated with a poor prognosis in both breast and ovarian cancer. HER-2/neu is a transmembrane protein with a relative molecular mass of 185 kd that is approximately 1255 amino acids (aa) in length. It has an extracellular binding domain (ECD) of approximately 645 aa, with 40% homology to epidermal growth factor receptor (EGFR), a highly hydrophobic transmembrane anchor domain (TMD), and a carboxyterminal cytoplasmic domain (CD) of approximately 580 amino acids with 80% homology to EGFR.

As used herein, the term "interferon-alpha (INF-α)" refers to a family of highly homologous species-specific proteins that inhibit viral replication and cellular proliferation and modulate immune response. Typical suitable interferon-alphas for the method of the present invention include, but are not limited to, recombinant interferon alpha-2b such as Intron-A® interferon available from Schering Corporation, Kenilworth, N.J., recombinant interferon alpha-2a such as Roferon interferon available from Hoffmann-La Roche, Nutley, N. J., recombinant interferon alpha-2c such as Berofor alpha 2 interferon available from Boehringer Ingelheim Pharmaceutical, Inc., Ridgefield, Conn., interferon alpha-n1, a purified blend of natural alpha interferons such as Sumiferon available from Sumitomo, Japan, or as Wellferon interferon alpha-n1 (INS) available from the Glaxo-Wellcome Ltd., London, Great Britain, or a consensus alpha interferon such as those described in U.S. Pat. Nos. 4,897,471 and 4,695,623 (especially Examples 7, 8 or 9 thereof and the specific product available from Amgen, Inc., Newbury Park, Calif., or interferon alpha-n3a mixture of natural alpha interferons made by Interferon Sciences and available from the Purdue Frederick Co., Norwalk, Conn., under the Alferon Tradename. The use of interferon alpha-2a or alpha-2b is preferred. Since interferon alpha-2b, among all interferons, has the broadest approval throughout the world for treating chronic hepatitis C infection, it is most preferred. The manufacture of interferon alpha-2b is described in U.S. Pat. No. 4,530,901.

As used herein, the term "Interleukin 2 (IL-2)" refers to a cytokine which stimulates the immune system and which exerts its biological effects following binding to specific receptors on the surface of target cells. IL-2 has many biological effects, for example, it is known to induce the stimulation of activated B and T cells (including cytotoxic T cells), natural killer (NK) cells, and lymphokine activated killer (LAK) cells. IL-2 may be obtained as a prescription drug, for example, PROLEUKIN®, manufactured by Chiron Corporation (Emeryville, Calif.). IL-2 may be prepared from various sources and by different methods, as disclosed in numerous U.S. patents. These patents include, but not limited to, the preparation of IL-2 from T cells, such as from hybrid murine T cell lines or malignant human T cell lines, as disclosed in U.S. Pat. Nos. 4,407,945, 4,473,642, and 4,401,756, respectively, and the preparation of recombinant human IL-2 as disclosed in U.S. Pat. Nos. 4,992,367, 4, 407,945, and 4,473, 642.

Ongoing research involving oncogenes has identified at least forty oncogenes operative in malignant cells and responsible for, or associated with, transformation. Oncogenes have been classified into different groups based on the putative function or location of their gene products (such as the protein expressed by the oncogene). Oncogenes are believed to be essential for certain aspects of normal cellular physiology.

Cancer continues to be a major health problem, despite significant progress made in the area of treatment. The standard treatment regimes of chemotherapy, radiation therapy, surgical intervention and combinations of the three, often fail to produce a long lasting cure. In many cases, the cancer patient having undergone the treatment often relapses back to the disease condition after some period of time. Further exacerbating the problem is the severity of these treatment regimes to the patient. In the instance of melanoma, a cure for metastatic melanoma has not been achieved using conventional chemotherapy. Response rates of 35% to 50% have been reported with the Dartmouth regimen of combination chemotherapy (DTIC, cis-platin, BCNU and tamoxifen), but the duration of survival has remained at six to ten months. High rates of remission have been reported for aggressive "high dose intensity" chemotherapy and repletion of hematopoeisis with autologous bone marrow transplants. The median duration of survival in these treated patients was short, approximately four months.

Rosenberg and colleagues have attempted to use infusion of activated lymphocytes as a treatment for various cancers. Initially, lymphokine-activated killer cells (LAK) and later tumor-infiltrating lymphocytes (TIL) activated ex vivo with IL-2 were used, but evidence for efficacy is equivocal. In fact, controlled clinical trials have failed to show an advantage to the use of ex vivo-activated cells over direct administration of IL-2 to patients. Thus, the benefits of LAK and TIL therapy are marginal, and the side effects are typically so severe that many trials have been discontinued prematurely.

Studies in mouse tumor models have demonstrated that adoptive immunotherapy, in vivo immunization of T cells specific for a tumor antigens(s), is very efficacious with minimal toxicity. A major obstacle to applying this strategy to the treatment of human tumors is the identification of immunogenic antigens that render the tumor cells susceptible to cytotoxic T lymphocyte (CTL)-mediated destruction. The isolation of tumor-reactive T cells from melanoma patients has led to the identification of some of the tumor antigens (epitopes) against which CTLs are directed. These include tyrosinase (Brichard et al., *J. Exp. Med.* (1993) 178:489-495; Robbins et al., *Cancer Res.* (1994) 54:3124-3126), MART 1/Melan A (Kawakami et al., *J. Exp. Med.* (1994) 180:347-352), gp 100 (Bakker et al., *J. Exp. Med.* (1994) 179:105-1009; and Kawakami et al., *J. Immunol.* (1995) 154:3961-3968) and MACE (Gaugler et al., *J. Exp. Med.* (1994) 179:921-930). Of these, tyrosinase and MART-1 are nearly universally expressed on melanomas and thus are the logical choice for adoptive immunotherapy.

In recent years, significant improvements in survival on the order of several years have been noted in a small percentage of melanoma patients undergoing immunological therapy. This includes active specific immunotherapy with "cancer vaccines" as well as the use of non-specific boosters of the immune system such as cytokines, like IL-2, α-interferon and γ-interferon. However, the benefit of cytokines is lessened by side effects that often accompany their use, such as, nausea, fever, and flu-Ske syndrome.

Cytolytic T cells (CD8$^+$) are the main line of defense against viral infections. CD8$^+$ lymphocytes specifically recognize and kill host cells that are infected by a virus. Theoretically, it should be possible to harness the immune system to combat other types of diseases including cancer. However, few in vitro/ex vivo procedures have been available for specifically activating CTLs. The identification of key melanoma antigens noted above and a method for specific in vitro activation CTLs described below now allow testing of the concept of adoptive immunotherapy of metastatic melanoma.

All naive T cells require two signals for activation to elicit an immune response. For CD8$^+$ lymphocytes (CTLs), the first signal, which imparts specificity, consists of presentation to the CD8$^+$ cell of an immunogenic peptide fragment (epitope) of the antigen bound to the Class I MHC (HLA) complex present on the surface of antigen-presenting cells (APCs). This complex is recognized specifically by a T cell antigen receptor (TCR), which communicates the signal intracellularly.

Binding to the T cell receptor is necessary but not sufficient to induce T cell activation, and usually will not lead to cell proliferation or cytokine secretion. Complete activation requires a second co-stimulatory signal(s), these signals serve to further enhance the activation cascade. Among the co-stimulatory molecules on antigen-presenting cells, B7 and cell adhesion molecules (integrins) such as ICAM-1 assist in this process by binding to CD28 and LFA-1, respectively, on the T cell. When a CD8+ cell interacts with an antigen-presenting cell bearing an immunogenic peptide (epitope) bound by a Class I MHC molecule in the presence of appropriate co-stimulatory molecule interactions, the $CD8^+$ cell becomes a fully activated cytolytic T cell.

Lymphocyte-mediated cell killing involves a sequence of biological events beginning with the binding of the $CD8^+$ CTL to an antigen-bearing target (tumor) cell by means of the recognition process described above for T cell activation.

The interaction between CD8+ cells and antigen-presenting cells or target (tumor) cells as described above is depicted in FIG. 1. The interaction begins with the binding of antigen in association with an MHC Class I molecule on the APC or target cell to the T cell antigen receptor (TCR). Accessory molecules such as lymphocyte function antigens (LFA-1, LFA-2 and LFA-3), intercellular adhesion molecule 1 (ICAM-1, ICAM-2) and T cell co-stimulatory factors (CD40, CD70, B7) enhance cell-cell adhesion or transduce additional cell activation signals. However, the requirement for lymphocyte-mediated cell killing can occur in the presence of the MHC/peptide alone, a situation common to most tumor cells.

After cell-cell interaction, the CTL kills the target cell through the action of soluble cytolytic mediators (perforin and granzymes stored in cytoplasmic granules in the T cell) and a CTL surface molecule (Fas ligand). After the cytolytic attack, target cells die by necrosis (membrane perforation and organelle destruction) or apotosis (chromatin condensation, DNA fragmentation and membrane blebbing).

The mechanisms of lymphocyte-mediated cytolysis is graphically depicted in FIG. 2. In Panel A of FIG. 2, after binding to the target cell, cytoplasmic granules in the CTL are rapidly reoriented toward the target cell for release of granules containing perforin and granzymes into the intercellular space. These proteolytic enzymes form pores in the plasma membrane of the target cell eventually leading to cell necrosis. In Panel B, after binding to the target cell the level of Fas ligand expression on the CTL increases. The interaction of Fas ligand and the Fas receptor on the target cell leads to apoptosis. Proteases such as CPP32 and others related to IL-1b-converting enzyme (ICE) have been implicated in the induction of apoptosis.

It is possible to use naturally-occurring antigen-presenting cells, for example, dendritic cells, macrophages and autologous tumor cells for in vitro $CD8^+$ activation. However, the efficiency of activation following this approach is low. This is because the Class I molecules of native APCs contain many other types of peptide epitopes besides tumor epitopes. Most of the peptides are derived from normal innocuous cell proteins, resulting in a dilution of the number of active native APCs that would actually be effective against a tumor (Allison et al., *Curr. Op. Immunol.* (1995) 7:682-686).

A more direct and efficient approach to this problem is to specifically activate $CD8^+$ cells only with those epitopes relevant to combating a specific disease, (such as, cancer) or tumor specific antigens (such as, melanoma-specific antigens). To this end, an artificial antigen presenting cell is created by expressing MHC Class I molecules in *Drosophila melanogaster* (fruit fly) cells. Since *Drosophila* does not have an immune system, the TAP-1,2 peptide transporters involved in loading peptide epitopes onto class I molecules are absent. As a result, the class I molecules appear on the *Drosophila* cell surface as empty vessels. By incubating these transfected *Drosophila* cells with exogenous peptides that bind to the class I molecules, such as, cancer or tumor specific epitopes, including but not limited to, melanoma specific epitopes, it is possible to occupy every class I molecule with the same peptide. High density expression of class I molecules containing a single peptide in these *Drosophila* APCs permit generation of cytotoxic $CD8^+$ T cells in vitro which are completely specific for the antigen peptide. Methods and procedures for preparing *Drosophila* cells are taught in U.S. Pat. No. 5,529,921, issued Jun. 25, 1996 entitled "*In Vitro Activation of Cytotoxic T-Cells Using Insect Cells Expressing Human Class I MHC and β2-Microglobulin*", and U.S. Pat. No. 5,314,813, issued May 24, 1994 entitled "*Drosophila Cell Lines Expressing Genes Encoding MHC Class I Antigens And β2-Microglobulin and Capable of Assembling Empty Complexes and Methods of Making Said Cell Lines*". In particular, U.S. Pat. No. 5,529,921 discloses at column 26, line 56 to column 28, line 22 various methods of separating out and/or enriching cultures of precursor cells.

Additionally, this feature eliminates the need for in vivo stimulation of the immune system with high doses of various cytokines, thereby resulting in a treatment that foregoes the side effects caused by cytokines. Alternatively under suitable situations, or conditions, where appropriate and where the subject can derive benefit, the subject can be treated concurrently with low level dosages of α interferon, γ-interferon, and/or IL-2.

Eliminating the need for in vivo stimulation with cytokines provides an improvement to the quality of patient care. Treatment regimes that include the administration of cytokines to patients often result in the patient developing flu-like symptoms, such as nausea, vomiting, and fever. These side reactions are generally not life threatening, although a particularly severe reaction occurring in a patient who is already in a weaken condition could result in a life endangering situation. Another consideration is the adverse impact such side reactions have on patient acceptance and compliance of an otherwise beneficial treatment regime. Removing the need for in vivo stimulation with cytokines results in a treatment regime that improves the comfort of the patient, and provides the clinician with an effective method of treatment that his or her patient is more likely to comply with.

The utility of this method for adoptive immunotherapy of tumors has been demonstrated in mice using transfected *Drosophila* cells as APCs and $CD8^+$ cells from the 2C line of T cell receptor (TCR) transgenic nice. In this system, purified $CD8^+$ 2C cells are highly responsive to in vitro peptides presented by MHC Class I ($L^d$)-transfected *Drosophila* cells also bearing the co-stimulatory molecules B7-1 and ICAM-1. Transfected *Drosophila* cells as a probe for defining the minimal requirements for stimulating unprimed CD8+ T cells (Cai et al., *P. N. A. S.* USA (1996) 93:14736-14741). Alternatively, when un-separated mouse spleen cells are used as responders in place of purified 2C cells, the need for co-stimulatory molecules does not apply. In this instance, the CDS+ cells in the spleen population receive "bystander" co-stimulation from activated B cells. Utilizing this finding, it has been possible to show that MHC Class I ($L^d$)-transfected *Drosophila* cells are able to induce normal DBA/2 mouse spleen cells to respond to syngeneic P815 mastocytoma tumor-specific peptides in vitro in the absence of added lymphokines. Injection of these CTLs into DBA/2 mice bearing P815 mastocytoma led to rapid tumor regression (Sun et al., *Immunity* (1996) 4:555-564).

Figure 3:
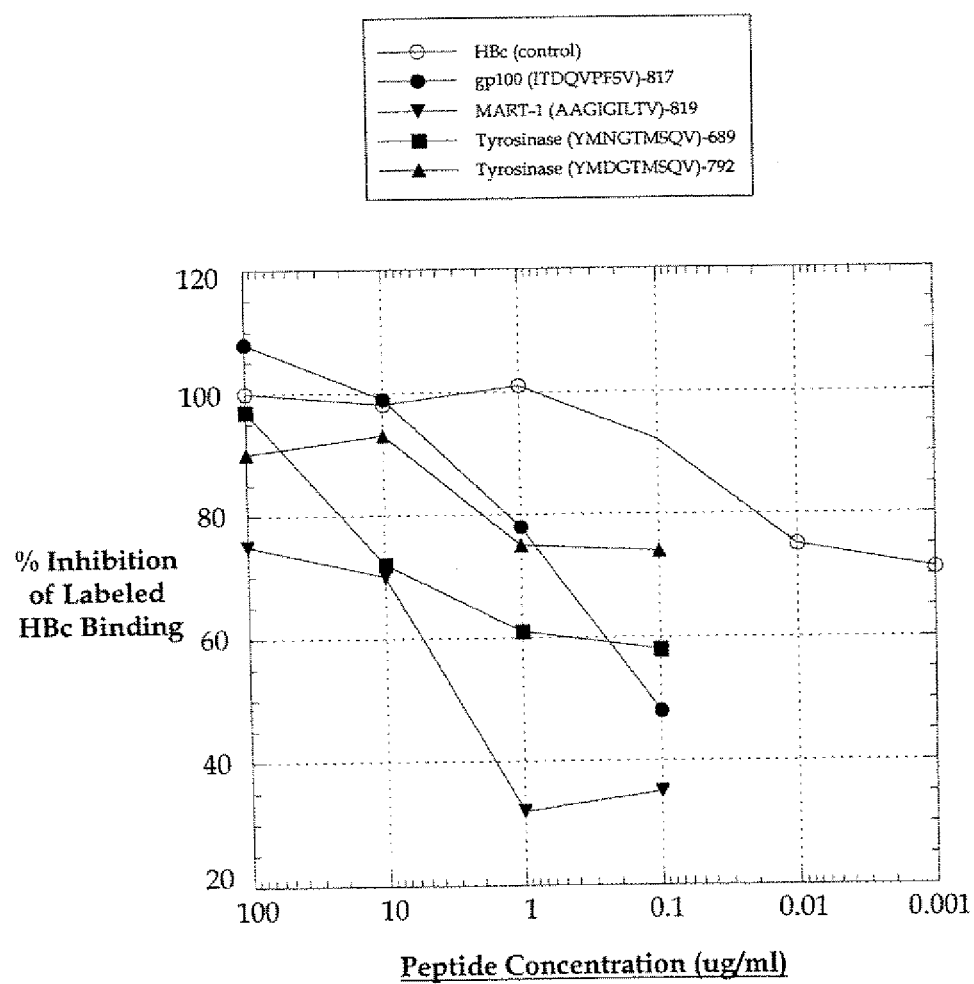
FIG. 3: This figure shows the result of an experiment where several different peptides, gp 100 (ITDQVPFSV; SEQ ID NO: 4)-817, MART-1 (AAGIGILTV; SEQ ID NO: 6)-819, Tyrosinase (YMNGTMSQV; SEQ ID NO: 1)-689 and Tyrosinase (YMDGTMSQV; SEQ ID NO: 2)-792, were tested in a competition assay to identify peptide binders that could be used to load multiple peptides onto Drosophila cells expressing human empty class I molecules.

Procedurally, normal DBA/2 mouse spleen cells were cultured in vitro with MHC Class I ($L^d$)-transfected *Drosophila* cells loaded with P1A.35-43 peptide, a tumor-specific epitope from the DBA/2-derived P815 mastocytoma cell line. Lymphocytes harvested from the cultures after five days displayed strong cytotoxic T lymphocyte (CTL) activity toward P815 tumor cells in vitro, but failed to lyse P1024, a mutant cell line of P815 that does not express P1A.35-43, as shown in FIG. 3, Panel A. When these CTLs were injected into DBA/2 mice previously inoculated with P815 cells three days earlier, the tumors grew unimpeded during the first week, but were subsequently eliminated within the next week, as shown in FIG. 3, Panel B. Specificity was demonstrated by the absence of any effect on P815 growth when CTLs were immunized in vitro against an irrelevant antigen, such as, viral nucleoprotein peptide, as shown in FIG. 3, Panel B. In summary, major histocompatibility complex Class I (Ld)-transfected *Drosophila* cells induced normal DBA/2 mouse spleen cells to respond to syngeneic P815 mastocytoma tumor-specific peptides in vitro in the absence of added lymphokines. Injection of these CTLs into DBA/2 mice bearing P815 mastocytoma led to rapid tumor regression (Wolfel et al, *J. Exp. Med.* (1993) 178:489-495).

Human Studies in Vitro

Human CTLs from healthy subjects were immunized in vitro against tyrosinase, MART-1 and gp100 when loaded separately on *Drosophila* APCs and evaluated for lysis on JY cells (FIG. 4). The same peptides can be added together on single *Drosophila* APCs to generate a multi-specific bulk CD8 preparation. Melanoma-specific CTLs from healthy subjects were induced using the full stimulation/re-stimulation protocol and tested for their ability to lyse Jurkat cells loaded with each of the of the peptides used in the stimulations (FIG. 5). cell line. FIG. 6 shows CTL activity after two different in vitro stimulation protocols. One in which the multiple peptides were loaded onto individual *Drosophila* cells and mixed before the primary stimulation (combo mix), or the multiple peptides were mixed and then loaded onto the *Drosophila* APCs (combo load). Panel A represents the results of the combo mix protocol on peptide-loaded target cells. Panel B represents the results of combo load protocol on peptide-loaded target cells. Panel C represents the killing on melanoma targets generated from both protocols.

The use of any natural, or artificial, antigen presenting cell (APC) system to generate cytotoxic T lymphocytes in vitro is limited by the antigen specificities these systems are capable of generating.

The following APC systems have been utilized to generate antigen-specific CTL's to single epitopes: 1) human dendritic cells (DC) pulsed with defined peptides; 2) peripheral blood mononuclear cells (PBMCs) which have been driven to lymphoblasts and pulsed with peptides; 3) lymphoblastoid cell lines (LCL) where the natural peptides are acid-stripped and loaded with the peptides of interest; 4) *Drosophila* cells engineered to express empty class I molecules; and Mouse 3T3 cells transfected with human class I and co-stimulatory molecules (J. B. Latouche and M. Sadelain, *Nature Biotech* (2000) 18:405-409).

Dendritic cells (DCs) are considered the primary antigen presenting cell system in humans because of their wide application in presenting primary antigen cells. Self or foreign proteins are processed within a DC. The resultant peptide epitopes are presented by HLA molecules, and are transported to the surface of the DC. However, it was found that DCs would not consistently generate in vitro, CTLs directed against four different peptides. This would have provided CTLs having activity corresponding to each of the four peptides. In addition, it was also found that the phenotype of the DC at the time of peptide pulsing, mature or immature, did not effect the outcome.

Alternatively, *Drosophila* cell stimulation usually resulted in CTLs directed against up to ten different types of peptides. This provides CTLs that are active to each of the ten peptides. The ability of *Drosophila* cells and DC to elicit CTL responses were evaluated, initially to a single peptide epitope, following the standard stimulation protocols for each. In order to compare DCs and transfected *Drosophila* cells, immature DCs were generated by culturing for one week autologous monocytes in the presence of IL-4 and GM-CSF. Mature DCs were obtained from immature DCs by addition of TNF α to the culture medium twenty-four hours prior to harvesting. DCs (immature and mature) were harvested, pulsed with peptides and mixed with purified CD8 cells following the procedure used for the stimulation of CDS cells and peptide-pulsed *Drosophila* cells. *Drosophila* cells were found to be generally better stimulators than DC when evaluated for tyrosinase peptide epitope 689, as shown in FIG. 7. Further, DCs displaying either the immature or mature phenotype (FIG. 8) were not as efficient as *Drosophila* cells in eliciting specific CTL responses when defined peptides were used to pulse the APCs. This is particularly surprising, because of the dominant role played by DCs in the immune system. A comparison study with one donor was performed, as shown in FIG. 9. Specific killing was generated against four different peptides when using fly cells as stimulators whereas immature DCs resulted in marginal specific killing and mature DCs resulted in specific killing against only one of the four peptides used for stimulation.

Preparation of Cytotoxic Lymphocytes $CD8^+$ cells isolated from leukapheresis samples by positive selection with anti-CD8 antibody are stimulated against four different melanoma associated peptides presented by *Drosophila* cells expressing Human Class I molecules (HLA-A2.1), 37.1, ICAM-1, LFA-3 and B7.2. $CD8^+$ cells are re-stimulated for two rounds with autologous monocytes loaded with the peptide epitope in the presence of IL-2 and IL-7. CTLs are non-specifically expanded with OKT3 and IL-2. CTL activity is measured against Malme 3M cells and purity of $CD88^+$ T cells is assessed by flow cytometry.

The manufacturing processes and protocols are done according to Good Laboratory Practices and Good Manufacturing Practices "Good Laboratory Practices" and "Good Manufacturing Practices" are standards of laboratory and manufacturing practices which are set by United States Food and Drug Administration, and are readily known to those of skill in the art. The CTLs are monitored for identity, viability, CTL activity, sterility, and endotoxin content.

A listing of peptide epitopes suitable for use in the methods of the present invention to treat breast and ovarian cancers are shown in the following Table 1. It is readily apparent to those of ordinary skill in the art that a wide variety of peptide epitopes in addition to those listed in the following Table 1 will also be suitable for use in the methods of the present invention to treat breast and ovarian cancers, provided that such peptides are T cell epitopes.

TABLE 1

Identified HLA-A2.1 Restricted Epitopes for Tumor Associated Antigens as Targets for Breast and Ovarian Cancers

| Target (residues) | Name | PRI # | AKA | Sequence (SEQ ID NO:) | HLA Peptide-Binding Prediction |
|---|---|---|---|---|---|
| Her-2/neu | | | | | |
| 789-797 | | 826 | E90 | CLTSTVQLV (SEQ ID NO:7) | 160 |
| 48-56 | | 827 | D113 | HLYQGCQVV (SEQ ID NO:13) | |
| 369-377 | | 835 | E75 | KIFGSLAFL (SEQ ID NO:8) | 481 |
| 654-662 | | 837 | GP2 | IISAVVGIL (SEQ ID NO:14) | |
| 650-658 | | 838 | GP1 | PLTSIISAV (SEQ ID NO:15) | |
| 773-782 | | 861 | | VMAGVGSPYV (SEQ ID NO:16) | |
| 851-859 | | 862 | E89 | VLVKSPNHV (SEQ ID NO:17) | 118 |
| 971-979 | | 863 | C85 | ELVSEFSRM (SEQ ID NO:18) | |
| AES | Amino enhancer of the split Notch | | | | |
| G128-135 | | 893 | G76 | GPLTPLPV (SEQ ID NO:19) | |
| MUC-1 | Mucin | | | | |
| 950-958 | | 908 | 1.1 | STAPVHNV (SEQ ID NO:20) | |
| CEA | Carcinoembryonic Ag | | | | |
| 571-579 | | 879 | CAP-1 | YLSGANLNL (SEQ ID NO:21) | |
| FBP | Folate binding protein | | | | |
| 191-199 | | 914 | E39 | EIWTHSYKV (SEQ ID NO:22) | |
| C-Lectin | MESM, RELP | | | | |
| 8-16 | | | C8 | KMASRSMRL (SEQ ID NO:9) | CTL Activity |
| 77-86 | | | C77 | SILSLKEAST (SEQ ID NO:23) | CTL Activity |
| NY-ESO-1 | | | | | |
| 157-165C | | 894 | | SLLMWITQC (SEQ ID NO:24) | native |
| 157-165V | | 906 | | SLLMWITQV (SEQ ID NO:25) | modified |
| 155-163 | | 913 | | QLSLLMWIT (SEQ ID NO:26) | |
| Pec60 | | | | | |
| 20 | | | P20 | ALALAALLVV (SEQ ID NO:10) | CTL Activity |
| 25 | | | P25 | ALLVVDREV (SEQ ID NO:11) | CTL Activity |
| CA-125 | | | | | |
| 157-165 | | 900 | | YLETFREQV (SEQ ID NO:27) | 38 |
| 255-263 | | 902 | | VLLKLRRPV (SEQ ID NO:28) | 88 |
| 337-345 | | 901 | | GLQSPKSPL | 21 |

TABLE 1-continued

Identified HLA-A2.1 Restricted Epitopes for Tumor Associated Antigens as Targets for Breast and Ovarian Cancers

| Target (residues) | Name | PRI # AKA | Sequence (SEQ ID NO:) | HLA Peptide-Binding Prediction |
|---|---|---|---|---|
| 546-554 | | 903 | (SEQ ID NO:29) ELYIPSVDL | 5 |
| 898-906 | | 899 | (SEQ ID NO:30) KAPLFAGPPV | 13 |
| 414-422 | | 910 | (SEQ ID NO:31) FMWGNLTLA | 315 |
| | | | (SEQ ID NO:32) | |
| MAGE-3 | | | | |
| 271-279 | | 909 | FLWGPRALV | |
| | | | (SEQ ID NO:33) | |
| Telomerase | hTRT | | | |
| 540-548 | | 907 | ILAKFLHWL | |
| | | | (SEQ ID NO:34) | |
| 865-873 | | 911 | RLVDDFLLV | |
| | | | (SEQ ID NO:35) | |
| G250 | | | | |
| 245-262 | | 912 | HLSTAFARV | |
| | | | (SEQ ID NO:36) | |

Treatment Regimen for Malignant Melanoma Using Ex Vivo-generated Autologous T Lymphocytes with Specificity for Melanoma-Associated Target Antigen Clinical studies have been performed on advanced, metastatic melanoma patients using ex vivo-generated autologous cytotoxic T lymphocytes (CTLs) with specificity for melanoma-associated target antigen. At least a single infusion of the ex vivo-generated CTLs was administered to the patient per cycle of treatment. It was noted that concomitant administration of either IFN-α or IL-2 to the patients at specific times and doses benefited the priming of tumor cells for lysis by the antigen-specific CTLs and the in vivo persistence of the CTLs.

Combined Therapy of Interferon and CTLs

Interferon-alfa (IFNα) has a broad spectrum of immunomodulatory and antiproliferative effects in a variety of malignancies. Several clinical trials in the past decade have provided clear evidence that IFNα has antitumor activity in melanoma (Legha, Cancer (1986) 57:1675-1677). When used as a single-agent therapy, rIFN-α-2a and rIFN-α-2b have produced a mean response rate of 15% (range, 6%-27%) with response duration ranging from 1 to 60+ months. A summary of several single-agent IFN-α trials in metastatic melanoma is listed in Tables 2 and 3.

TABLE 2

Single-Agent IFN-α Trials in Metastatic Melanoma (IFN-α-2a)

| Study | Dose (MU) | Route/schedule | entered* | CR | PR | % | Duration (mo) |
|---|---|---|---|---|---|---|---|
| Creagan et al, 1984[2] | 12/m2 | IM, TIW for 12 Wks | 30/30 | 1 | 5 | 20 | 2 to 13+ |
| Creagan et al, 1984[3] | 50/m2 | IM, TIW for 12 Wks | 31/31 | 3 | 4 | 23 | 3 to 11 |
| Coates et al, 1986[4] | 20/m2 | IV, daily for 5 of 14 d | 16/15 | 0 | 0 | 0 | |
| Hersey et al, 1985[5] | 15 to 50/m2 | IM, TIW | 20/18 | 2 | 0 | 11 | 6 to 12 |
| Legha et al, 1987[6] | 18 to 36/m2 | IM, daily for 10 Wks | 35/31 | 0 | 3 | 10 | 6 to 7 |
| Steiner et al, 1987[7] | 9 to 36/m2 | IM, daily | 12/12 | 1 | 0 | 8 | 4+ |
| Elsasser-Beile et al, 1987[8] | 18/m2 | IM, daily for 10 Wks | 21/21 | 3 | 0 | 14 | 12+ to 16+ |
| IFN-α-2a | Subtotal | | 196/189 | 10 | 14 | 12 | |

[2]Creagan et al., *J Clin Oncol* (1984) 2: 1002-1005;
[3]Creagan et al., *Cancer* (1984) 54: 2844-2849;
[4]Coates et al., *J Interferon Res* (1986) 6: 1-4;
[5]Hersey et al., *Br J Cancer* (1985) 51: 815-826;
[6]Legha et al., *J Clin Oncol* (1987) 5: 1240-1246;
[7]Steiner et al., *J Cancer Res Clin Oncol* (1987) 113: 459-465;
[8]Elsasser-Beile et al., *Fortschr Med* (1987) 105: 401-403.

TABLE 3

Single-Agent IFN-α Trials in Metastatic Melanoma (IFN-α-2b)

| Study | Dose (MU) | Route/schedule | entered* | CR | PR | % | Duration (mo) |
|---|---|---|---|---|---|---|---|
| Kirkwood et al, 1985[9] | 10 to 100/m2 | IM or IV, daily × 28 | 23/23 | 2 | 2 | 22 | 3 to 60+ |
| Dorval et al, 1986[10] | 10/m2 | SC, TIW | 24/22 | 2 | 4 | 27 | 2 to 5 |
| Sertoli et al, 1989[11] | 10/m2 | IM, TIW | 21/21 | 0 | 3 | 14 | 7 to 13 |
| Robinson et al, 1986[12] | 10/m2 | SC, TIW for × 12 wk | 51/40 | 4 | 6 | 25 | 1 to 54+ |
| IFN-α-2b | Subtotal | | 119/106 | 9 | 15 | 20 | |

[9] Kirkwood et al., *Ann Intern Med* (1985) 103: 32-36;
[10] Dorval et al., *Cancer* (1986) 58: 215-218;
[11] Sertoli et al., *Oncology* (1989) 46: 96-98;
[12] Robincon et al., *Immunobiology* (1986) 172: 275-282.

One mechanism of action of IFN-α seems to be the up-regulation of tumor antigen expression on the melanoma cells: it has the ability to enhance the expression of immunologically important molecules on the surface of the tumor. Such immunologically important molecules include, but are not limited to, the histocompatibility (mouse H-2 or human HLA) antigens, accessory molecules such as the intracellular adhesion molecule-1 (ICAM-1/CD54), as well as, tumor-associated antigens (Robincon et al., *Immunobiology* (1986) 172:275-282; Borden et al., in Mitchell, Miss., (ed): *Biological Approaches to Cancer Treatment; Biomodulation*. New York, N.Y., McGraw-Hill, (1992) pp 440-476). The immunomodulatory effects of IFN-α can potentially improve the ability of the immune system, including both antibodies and lymphocytes, to recognize and attack the tumor in vivo.

Active specific immunotherapy has demonstrated significant clinical activity in the treatment of disseminated melanoma. The results of immune function studies have shown that melanoma vaccine treatment increases the frequency of anti-melanoma CTLs (Carrel et al., *Eur J Immunol* (1985) 15:118-123). Combined immunotherapy regimens (IFN-α and melanoma vaccine) are currently being used in the treatment of disseminated melanoma (Agarwala et al., *BioDrugs* (1999) 12:193-208). It is believed that these two modalities of immunotherapy may act synergistically.

The Eastern Cooperative Oncology Group (ECOG) completed a prospective randomized controlled study of interferon alfa-2b (IFN-α-2b) versus observation as surgical adjuvant therapy in 287 patients with melanoma (Kirkwood et al., *J Clin Oncol* (1996) 14:7-17). The dose used in the study was the maximum tolerated dose: 20MU/m$^2$/d intravenously (IV) five days per week for four weeks followed by 10MU/m$^2$ three times per week subcutaneously (SC) for 48 weeks. The results showed that there was a significant prolongation of relapse-free survival and overall survival in the group receiving IFN-α-2b. However, toxicity was considerable; 67% of the patients had severe (Grade 3) toxicity and 9% had life-threatening toxicity. Dose modification was required in the majority of the patients. The treatment was also costly. On the basis of the ECOG study, the FDA approved interferon as a surgical adjuvant treatment for melanoma in 1996.

In a large, prospective study, randomized trial in high-risk melanoma patients, 642 participants were randomized to three arms; those received high-dose interferon alfa-2a: 20MU/m$^2$ intramuscularly three times per week for 12 weeks, low-dose interferon, or observation. The time to progression (TTP) was prolonged only in the high-dose group, although the overall survival was the same for all three groups (Kirkwood et al., *J Clin Oncol* (2000) 18:2444-2458). The World Health Organization (WHO) conducted a trial of low-dose interferon alfa-2a: 3 MU/m$^2$ SC three time per week for 3 years versus observation as adjuvant therapy in 427 patients with high-risk melanoma (Cascinelli, *Proc Am Soc Clin Oncol*, (1995) pp 410 (abstr)). There was no difference in the disease-free survival or survival in the patients receiving interferon.

The present invention provides a method for treating a subject with melanoma, comprising the steps of:
a) administering to said subject an effective amount of interferon-alfa that is capable of enhancing the expression of tumor antigen on the surface of the tumor; and
b) inoculating said subject with an effective amount of autologous cytotoxic T lymphocytes with specificity for melanoma-associated target antigen.

Either INF-α-2a or INF-α-2b can be used in the present method of treatment. INF-α can be administered to the patient via SC, IM, or IV. The effective amount of interferon-affa for the present method is the amount of INF-α that is sufficient to up-regulate both HLA (class I) expression and melanoma-associated antigen expression, two key requirements for recognition and lysis by antigen-specific T cells. This effective amount can be determined by those skilled in the art. Example 5 (infra) describes some considerations in determining the effective amount of INF-α to be used in the present method of treatment. Preferably, for lowering the side effects caused by INF-α, the effective amount of INF-α-2a is about 5-20 MU/m2/day, and the effective amount of INF-α-2b is about 5-15 MU/m2/day. Also preferably, the effective amount of INF-α is administered to the patient only for a relatively short time period, for example, 3 to 7 days, immediately prior to inoculating the subject with an effective amount of autologous cytotoxic T lymphocytes with specificity for melanoma-associated target antigen. In a preferred embodiment, the effective amount of interferon-alfa is about 10 MU/m$^2$/day that is subcutaneously administered to the subject consecutively from day 5 to day 1 prior to inoculating said subject with the effective amount of autologous cytotoxic T lymphocytes with specificity for melanoma-associated target antigen.

The effective amount of autologous cytotoxic T lymphocytes with specificity for melanoma-associated target antigen is the amount of the ex vivo generated CTLs with specificity for melanoma-associated target antigen that is sufficient to stop the growth or cause a decrease in size of a melanoma lesion when the CTLs are inoculated to the subject. Preferably, the effective amount of autologous cytotoxic T lymphocytes with specificity for melanoma-associated target antigen is about 1–10×10$^9$ cells/infusion.

The autologous cytotoxic T lymphocytes with specificity for melanoma-associated target antigen are obtained by a method comprising steps of:

a) preparing a non-naturally occurring antigen-presenting cell line(nnAPC), wherein said nnAPC is capable of presenting up to about fifteen different epitopes associated with said melanoma simultaneously where each epitope is a peptide of eight to ten amino acids in length;
b) loading the nnAPC with up to about fifteen different epitopes associated with said melanoma;
c) harvesting CD8+ cells from said subject;
d) stimulating said CD8+ cells with the epitope-loaded nnAPC cell line to obtain CD8+ cells specific for the melanoma;
e) growing the CD8+ cells specific for the melanoma in media containing IL-2 and IL-7;
f) nixing CD8-depleted peripheral blood monocytes collected from said subject with each epitope that said nnAPC has been loaded with;
g) irradiating said CD8-depleted peripheral blood monocytes with γ-radiation;
h) isolating adherent CD8-depleted peripheral blood monocytes;
i) loading said adherent peripheral blood monocytes with each epitope that said nnAPC has been loaded with;
j) restimulating said CD8+ cells specific for the melanoma with the γ-irradiated epitope-loaded adherent peripheral blood monocytes;
k) growing the restimulated CD8+ cells specific for the melanoma in media containing IL-2 and IL-7;
l) expanding the restimulated CD8+ cells specific for the melanoma by OKT3 antibody stimulation;
m) assaying the expanded CD8+ cells for suitable cytotoxic T lymphocytes activity, purity, sterility and endotoxin content;
wherein step (j) can be repeated for at least one more time.

Preferably, the non-naturally occurring antigen-presenting cell line is loaded with epitopes that are peptides derived from tyrosinase, gp100, and MART-1, such as those illustrated in SEQ ID NO: 1, SEQ ID NO: 2, SEQ ID NO: 4, SEQ ID NO: 5, and SEQ ID NO: 6.

Combined therapy of Interferon, CTLs and Interleukin-2

Human recombinant interleukin-2 is a lymphokine produced by recombinant DNA technology that has been shown to exhibit a variety of biological activities. In vitro, it has been shown to enhance tymphokine mitogenesis, enhance lymphocyte cytotoxicity, induce the killer activity of both lymphokine-activated and natural killer cells, and it also induces interferon-gamma production.

It has been investigated in clinical trials for the treatment of metastatic renal-cell cancer, Kaposi's sarcoma, colorectal cancer, non-Hodgkin's lymphoma, as well as metastatic melanoma. It has been used alone or in combination with chemotherapy, lymphokine activated killer (LAK) cells or tumor infiltrating lymphocytes (TILs) or biologics such as interferon. It has been administered at both high and low doses and by various infusion schedules (bolus and continuous). Response rates ranged from 15-20%.

An overview by Phillip in 1997 looked at 540 patients in 15 trials performed in the 1990's with single agent IL-2 (Phillip et al., *Semin Oncol* (1997) 14: Suppl 4: 32-38). Dosing varied from 12 MIU/m² boluses three times per week to continuous infusion from 3-7 MIU/m²/day. Overall response rate in the overview was 15% with a range of 3-50% and 2% complete remission. In a 1994 study of 134 patients reported by Rosenberg et al (*JAMA* (1994) 271: 907-913), high dose bolus IL-2 produced a remission rate of 7% with 9 complete remissions (CRs). Of the 9 in CR, 8 were disease-free for 9-91+ months. The Cytokine Working Group performed a retrospective analysis of 266 patients treated with high dose IL-2 bolus therapy that produced CR in 16 patients (6%), 69% of those were alive and progression-free at 5 years (Atkins et al., *Proc Am Soc Clin Oncol* (1997) 16: 494a).

A meta-analysis of 911 patients who were treated with combination IFN-α and IL-2 produced a response rate of 17% (Allen et al., *Proc Am Soc Clin Oncol* (1997) 16: 494a (1781)). Median survival was 11 months, which is not significantly greater than single agent therapy.

Administration of IL-2 can be used immediately after the CTL infusion to enhance lymphocyte mitogenesis, lymphocyte cytotoxicity and gamma interferon production in an effort to maintain the antigen-specific T cells in vivo.

In a preferred embodiment, the present invention provides a method for treating a subject with melanoma, comprising the steps of:
a) administering to said subject an effective amount of interferon-alfa that is capable of enhancing the expression of tumor antigen on the surface of the tumor;
b) inoculating said subject with an effective amount of autologous cytotoxic T lymphocytes with specificity for melanoma-associated target antigen; and
c) administering to said subject an effective amount of interleukin-2 that is capable of enhancing the in vivo maintenance of the autologous cytotoxic T lymphocytes with specificity for melanoma-associated target antigen.

Interleukin-2 can be administered to the patient via SC, IM, or IV. The effective amount of interleukin-2 is the amount of IL-2 that is sufficient to maintain the ex vivo generated antigen-specific CTLs in vivo. This effective amount can be determined by those skilled in the art. Example 5 (infra) describes some considerations in determining the effective amount of IL-2 to be used in the present method of treatment. Preferably, for lowering the side effects caused by IL-2, the effective amount of IL-2 is about 2-10 MIU/day. Also, preferable, the effective amount of IL-2 is administered to the patient immediately after inoculating the subject with an effective amount of autologous cytotoxic T lymphocytes with specificity for melanoma-associated target antigen. In a more preferred embodiment, the effective amount of interleukin-2 is about 3 MIU/day that is subcutaneously administered to the subject consecutively from day 0 to day 27 after inoculating said subject with the effective amount of autologous cytotoxic T lymphocytes with specificity for melanoma-associated target antigen.

In a most preferred embodiment, the present invention provides a method for treating a subject with melanoma, comprising the steps of:
a) subcutaneously administering to the subject 10 MU/m²/day of interferon-alpha-2b consecutively from day 5 to day 1 prior to inoculating said subject with autologous cytotoxic T lymphocytes with specificity for melanoma-associated target antigen;
b) inoculating to the subject about $1–10 \times 10^9$ cells/infusion of the autologous cytotoxic T lymphocytes with specificity for melanoma-associated target antigen; and
c) subcutaneously administering to the subject about 3 MIU/day of interleukin-2 consecutively from day 0 to day 28 after inoculating said subject with the autologous cytotoxic T lymphocytes with specificity for melanoma-associated target antigen.

At the end of each cycle of the treatment, a complete response or partial response in said patient will be evaluated. The treatment cycle can be repeated at an interval of about 2 months.

This invention will be better understood by reference to the Experimental Details that follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

EXAMPLE 1

Manufacture of *Drosophila* Antigen-Presenting Cells

The Schneider S2 cell line was prepared from *Drosophila melanogaster* (Oregon-R) eggs according to published procedures and has been deposited with the American Type Culture Collection (CRL 10974). S2 cells are grown in commercial Schneider's *Drosophila* medium supplemented with 10% fetal bovine serum.

The pRma-3 plasmid vector for expressing MHC Class I and co-stimulatory proteins in S2 cells was derived from the pRmHa-1 expression vector constructed as described in the literature. It contains a metallothionein promoter, metal response consensus sequences and an alcohol dehydrogenase gene bearing a polyadenylation signal isolated from *Drosophila melanogaster*.

Complementary DNAs for Transfection were Prepared as Follows:

HLA-A2.1 and β-2 microglobulin: Reverse transcription-PCR from K562 cells using primers derived from the published sequence B7.1: Reverse transcription-PCR from K562 cells using primers derived from the published sequence ICAM-1: Reverse transcription-PCR from K562 cells using primers derived from the published sequence B7.2: Reverse transcription-PCR from HL-60 cells (ATCC CCL-240) using primers derived from the published sequence LFA-3: Reverse transcription-PCR from HL-60 cells (ATCC CCL-240) using primers derived from the published sequence Complementary DNAs were individually inserted into the pRmHa-3 vector. S2 cells were transfected with a mixture of HLA-A2.1, B7.1 and ICAM1 plasmid DNAs and the phshneo plasmid using the calcium phosphate precipitation method. Stably transfected cells were selected by culturing in Schneider's medium containing geneticin. Twenty-four hours before use, expression of the transfected genes was induced by addition of $CuSO_4$. The level of expression was assessed by flow cytometry using anti-HLA-A2.1, anti-B7.1 and anti-ICAM-1 antibodies. HLA expression by greater than 30% of the cells is necessary for efficient in vitro activation of $CD8^+$ lymphocytes.

Isolation of Human $CD8^+$ Cells $CD8^+$ cells are isolated from leukapheresis samples by positive selection using the Dynabeads™ isolation procedure (Dynal). An anti-human CD8 mouse monoclonal antibody (50 μg/ml in human gamma globulin [Gammagard®]) is added to washed cells in Dulbecco's PBS supplemented with 1% human serum albumin (Baxter-Hyland) and 0.2% Na citrate. After incubation at 4° C. for forty-five minutes with gentle mixing, the cells are washed and re-suspended in the same buffer containing Dynal magnetic beads (Dynabeads™) coated with sheep anti-mouse IgG at a bead to cell ratio of 1:1. The cells and beads are placed into a sterile tube and gently mixed at 4° C. for forty-five minutes. At the end of this time, the antibody-bound cells are removed magnetically using the MPC-1® separator according to the manufacturer's instructions (Dynal). Dissociation of the CD8 cell-bead complex is achieved by incubation at 37° C. for forty-five minutes in the presence of CD8 peptides$_{59-70}$ (AAEGLDTQRFSG; SEQ ID NO: 12). Free beads are removed magnetically and the CD8 cells are counted and analyzed by flow cytometry to evaluate purity. Recovery of $CD8^+$ cells is typically greater than 80%. Table 4 summarizes the cell composition of fourteen separate $CD8^+$ preparations from normal human PBMC preparations by positive selection with anti-CD8 antibody.

TABLE 4

Purification of $CD8^+$ Cells by Positive Selection Analyzed by Flow Cytometry

| CELL TYPE | PBMC | | POST SELECTION | |
|---|---|---|---|---|
| | Mean % | (Range) | Mean % | (Range) |
| CD8 T cells | 15% | (7-24) | 82% | (56-95) |
| CD4 T cells | 36% | (14-52) | 2% | (0.1-10) |
| CD 14 Monocytes | 15% | (7-26) | 0.8% | (0.2-2) |
| CD15 Neutrophils | 12% | (8-21) | 0.6% | (0.1-3) |
| CD19 B cells | 2% | (0.4-7) | 3% | (0.5-9) |
| CD56 NK cells | 6% | (2-17) | 6% | (0.1-20) |

In Vitro Immunization of Purified Human $CD8^+$ Cells
Primary Stimulation

Transfected *Drosophila* S2 cells are incubated in Schneider's medium ($10^6$ cells/ml) supplemented with 10% fetal calf serum and $CuSO_4$ at 27° C. for twenty-four hours. Cells are harvested, washed and re-suspended in Insect X-press medium (BioWhittaker) containing 100 μg/ml human tyrosinase$_{369-377}$. Following incubation at 27° C. for three hours, the S2 cells are mixed with $CD8^+$ cells at a ratio of 1:10 in RPMI medium (Gibco) supplemented with 10% autologous serum. The cell mixture is incubated for four days at 37° C. during which the *Drosophila* cells die off. On Day five, IL-2 (20 U/ml) and IL-7 (30 U/ml) are added to selectively expand the tyrosinase-specific CTL population.

Re-Stimulation

Frozen, autologous, CD8-depleted PBMCs, obtained at the time of leukapheresis, are thawed, washed and re-suspended at $10^6$ cells/ml in RPMI medium containing 10% autologous serum (as a source of β2 microglobulin) and 20 μg/ml tyrosinase$_{369-377}$. Following γ-irradiation (5,000 rads), the cells are incubated at 37° C. for two hours. Non-adherent cells are removed by washing with Dulbecco's PBS. Adherent monocytes are loaded with the tyrosinase epitope by incubation for 90 minutes in Hepes-buffered RPMI medium containing 10% autologous serum and 10 μg/ml tyrosinase$_{369-377}$. The supernatant is removed and the *Drosophila*-activated $CD8^+$ cell suspension ($3\times10^6$ cells/ml in RPMI medium with 10% autologous serum) is added at a ratio of 10 CD8+ cells to 1 adherent monocyte. After three to four days of culture at 37° C., IL-2 (20 U/ml) and IL-7 (30 U/ml) are added with a medium change to selectively expand the tyrosinase-specific CTL population.

Non-specific Expansion

Effector cells are non-specifically expanded by culturing them in RPMI medium supplemented with autologous serum, anti-CD3 monoclonal antibody (OKT®3), IL-2 and γ irradiated autologous PBMCs.

Assays for Activity and Purity
CTL Assay

Malme 3M cells are used as target cells in a $^{51}Cr$ release assay. $5\times10^6$ Malme 3M cells in RPMI medium containing 4% fetal calf serum, 1% HEPES buffer and 0.25% gentamycin are labeled at 37° C. for one hour with 0.1 mCi $^{51}Cr$. Cells are washed four times and diluted to $10^5$ cells/ml in RPMI with 10% fetal bovine serum (HyClone). In a 96-well microtiter plate, 100 µl effector CTLs and 100 µl peptide-loaded, $^{51}$Cr-labeled Malme 3M target cells are combined at ratios of 100:1, 20:1 and 4:1 (effector:target). K562 cells are added at a ratio of 20:1 (K562:Malme 3M) to reduce natural killer cell background lysis. Non-specific lysis is assessed using the non-tumor HLA-A2.1 fibroblast cell line, Malme 3. Controls to measure spontaneous release and maximum release of $^{51}$Cr are included in duplicate. After incubation at 37° C. for six hours, the plates are centrifuged and the supernatants counted to measure $^{51}$Cr release.

Percent specific lysis is calculated using the following equation:

$$\frac{cpm \text{ sample} - cpm \text{ spontaneous release}}{cpm \text{ maximum release} - cpm \text{ spontaneous release}} \times 100$$

Flow Cytometry.

CD8$^+$ cells, before and after in vitro activation, were analyzed for a number of cell surface markers using fluorescent monoclonal antibodies and FACS analysis. Results from a typical activation protocol using cells from a healthy donor is shown in Table 5.

TABLE 5

Flow Cytometry Analysis of In Vitro Activated CD8$^+$ Cells

| MARKER/<br>CELL TYPE | PRE-ACTIVATION<br>Mean % | POST-ACTIVATION<br>Mean % |
|---|---|---|
| CD8 T cell | 98 | 99 |
| TCRαβ T cell receptor | 98 | 42 |
| CD 44 lymph node homing receptor | 91 | 99 |
| CD45RO memory T cell | 58 | 88 |
| CD45RA | 41 | 31 |
| CD62L HEV homing receptor | 24 | 38 |
| CD56 NK cell | 1 | 11 |
| CD25 activated T cell | 0.1 | 29 |

In addition to activity and purity, CTL preparations will be assayed for sterility and endotoxin content.

REAGENTS

| REAGENT | SUPPLIER | GRADE | NOTES |
|---|---|---|---|
| rh IL-2 | Chiron | USP | sterile solution |
| rh IL-7 | Genzyme | Research | lyophilized, sterile solution |
| Human tyrosinase$_{369-377}$ | | Research | |
| Dynabeads ® M-450 | Dynal | GMP | sheep anti-mouse IgG magnetic beads |
| Human serum albumin | Baxter | USP | sterile, non-pyrogenic hepatitis virus-free, 25% solution |
| fetal bovine serum | Gemini | Research | sterile, BSE-, endotoxin-, mycoplasma-free |
| Gammagard ® | Baxter | USP | sterile, human immune globulin solution for injection |
| anti-CD8 antibody | | Research | mouse anti-human CD8 monoclonal antibody |
| CD8 peptide$_{59-70}$ | | Research | release of CD8$^+$ cells from magnetic beads |
| W6/32 | ATCC | Research | mouse anti-human HLA-A, B, C monoclonal antibody |

CELL LINES

| CELL LINE | SUPPLIER | NOTES |
|---|---|---|
| Drosophila S2 | ATCC | CRL 10974 |
| M3 | UCSD | Non-HLA-A2.1 human melanoma |
| Malme 3 | ATCC | Normal skin fibroblast from a melanoma patient |
| Malme 3M | ATCC | Metastatic melanoma from lung (same patient as Malme 3) |
| M14 | UCSD | HLA-A2.1 human melanoma |
| K562 | ATCC | human erythroleukemic cell line; target for NK cells |
| JY cells | ATCC | EBV-transformed, human B cell line expressing HLA-A2.1 and B7 |
| P815 and P1024 | ATCC | DBA/2 mouse mastocytoma cell lines |
| Jurkat A2.1 | ATCC | acute T cell leukemia transfected with human HLA-A2.1 |

ATCC: American Type Culture Collection

EXAMPLE 2

Trial of Cytotoxic T Cell Infusions Against Melanoma

Purpose Trial

This example teaches the effectiveness of cytotoxic T Cell infusions in the treatment of melanoma as assessed according to the following factors:
1. safety and toleration of re-infused autologous CTLs after in vitro immunization;
2. kinetics of infused CTLs in the systemic circulation factoring in limiting dilution analysis;
3. whole body disposition of CTLs by radioscintography;
4. cell composition of biopsied nodules by immunohistology (CTLs, TH, NK, B cells); and
5. regression of measurable lesions and duration of response over two months.

Patient Populations

Eligibility for treatment required patients to have histologically-documented, unresectable malignant melanoma that was measurable or otherwise capable of evaluation, and the HLA-A2 haplotype. Pretreatment evaluation included radiologic evaluation of the brain by MRI or CT scan, CT scanning of the chest and abdomen, and physical examination, especially of the skin and lymph nodes. The total number of patients treated was fifteen (nine male and six female). The ages ranged from 33 to 75 years with an average of 58 years. The average duration of metastatic disease was 1.5 years. A pretreatment skin test to determine whether a state of energy existed was performed on 14/15 patients with 5/14 testing negative for all seven of the common antigens evaluated. Patients were screened for the HLA-A2 haplotype by FACS analysis with an HLA-A2 specific monoclonal antibody (B137.2). Subtyping was performed by PCR analysis. All, but one of the patients, were HLA-A*0201, the exception (patient 08) was HLA-A*0205.

Treatment with Ex Vivo Generated Autologous CTLs

Fifteen patients were treated under this clinical protocol. All patients received, at least, a single infusion of autologous CTLs. The number of cycles and the dose of cells administered to each patient are summarized in FIG. 25. The number of cells generated in vitro was dependent on patient-related factors such as the numbers of PBMCs isolated from the aphaeresis procedure and the number of CD8+ T cells present in each PBMC preparation. Since all of the cells generated in vitro were re-infused into the donor, doses administered to each patient were necessarily varied. In an attempt to normalize the doses between patients, a calculated "potency" score was recorded for each dose. The value was obtained by multiplying the total number of cells by the lytic activity obtained with peptide-loaded target cells. Doses of T cells infused ranged from a minimum of $4 \times 10^7$ (patient 08) to a maximum of $3.2 \times 10^9$ (patient 13). Patients were entered into a second, third or fourth cycle of treatment based on their clinical status at the end of each cycle. The number of PBMCs obtained from the aphaeresis samples tended to be lower in patients undergoing additional cycles, especially if the start of the subsequent cycle was close to the end of the previous one. This is attributed to persistent lymphopenia due to the IFNα-2b administered during the previous cycle. The total number of naïve $CD8^+$ T cells isolated was dependent on its percentage in each of the PBMC preparations. The percent of $CD8^+$ T cells varied between 8% to 31% among the patients. The obtained expansion factor also contributed to the final cell numbers and ranged from 0.1-6.0 fold. The procedure for generating CTLs ex vivo is taught in the Specification and Example 1, above.

Up-Regulation of Class I and Melanoma-Associated Antigens in Response to IFNα-2b In an attempt to enhance the ability of the antigen-specific CTLs to lyse melanoma cells in vivo, low dose IFNα-2b was administered for five consecutive days prior to the CTL infusion, and thrice weekly for an additional four weeks. One way to measure an in vivo response to the cytokine is to evaluate biopsies obtained at serial time points by immunohistochemical analysis for positive staining with specific antibodies. Serial biopsies were obtained in one patient with multiple skin lesions (patient 04) for evaluation of both class I and antigen expression. The biopsies indicated Class I and MART-1 expression were weakly positive prior to any treatment (biopsy A). Following five days of subcutaneous injections of $10MU/m^2$, a dramatic increase in these two markers was noted biopsy B). For tyrosinase and gp100, immunohistochemical staining was negative to weakly positive, respectively in the pretreatment samples biopsy A). After the initial five-day IFNα dose, and thirteen additional treatments, expression of these later antigens was increased in the stained tissue samples (biopsy C).

Antigenic Specificity of Ex Vivo-Generated CTLs

CTLs generated from all patients were evaluated on the day of release against peptide-loaded T2 targets, an HLA-A2 melanoma cell line (Malme3M) and an autologous melanoma line, if biopsy material was available to establish a line. Each prepared dose of cells was evaluated for its cytolytic activity. Peptide-loaded T2 cells, presenting either each peptide alone, or all four peptides simultaneously, were used to determine the specificity of the CTL response generated for each patient. The ability to lyse endogenously-expressed, melanoma-associated, antigen-bearing cells was assessed with an HLA-A2 matched line or an autologous tumor line. In addition to cytolytic activity, antigen-specificity was evaluated with an established method for detecting intracellular gamma interferon production, made in response to a specific peptide stimulus. The CTLs generated at the end of the ex vivo protocol were evaluated by this method. The percent of cells specific for each of the peptides was recorded individually. The total number of specific cells in each bulk CD8 culture from patient 13 was calculated by adding each of the peptide specificities detected in that population of T cells. An increase in the total number of specific cells could be detected with each successive treatment cycle.

Detection of CDS and CD4 Cells Infiltrating Tumor Biopsies Post-CTL Therapy

Biopsy samples from all patients prior to, during and after treatment would have been ideal. However, the experimental conditions allowed for biopsy samples from only a limited number of patients. Tumor tissue was obtained from five of the fifteen patients enrolled in the study. In two patients (patients 08 and 13) biopsy samples were available at five and six weeks post T cell therapy, respectively. Examination of the tissue samples revealed the presence of both infiltrating CD8 and CD4 cells. One of the tumor samples was taken from a skin lesion in the occipital region of the scalp, which increased in size by the time of the follow up examination, four weeks after a second infusion of T cells. The biopsy revealed necrosis of the tissue that was heavily infiltrated with lymphocytes. The other biopsy was from the head of a femur bone, removed during hip replacement surgery. The skin lesion from patient 08 was strongly positive (4+) for both a general class I, and a specific HLA-A2 marker. Tyrosinase and gp100 were weakly positive (1+ and 2+, respectively), while MART-1 was negative in this same sample. Regions of the biopsy from patient 13 were also necrotic, with more heterogeneous staining; distinct populations of tumor cells lacking expression of the HLA-A2.1 molecule, and one or more of the MAAs. However, intact tissue regions revealed strong class I (4+), and all of the melanoma-associated antigens. The lymphocytic infiltrations in this later sample appeared to surround the tumor nodules rather than to deeply infiltrate them. However, the highest percentage of cells directly associated with the tumor were CD8 cells. The lack of pretreatment biopsy samples from both of these patients prevented a confirmation of similar types of infiltrating cells in tissue samples prior to treatment.

CT Scans Post-T Cell Therapy Confirm an Objective Response

CT scans were part of the pretreatment screening criteria and the post treatment follow-up examination. Patient 10 received a single infusion of $8 \times 10^8$ CTLs (Jul. 27, 1999) five weeks after the pretreatment scan (Jun. 23, 1999). When a CT scan of the chest was repeated one month after the infusion (Aug. 27, 1999), a dramatic decrease in the size of a lung lesion was noted. Similarly, patient 14 underwent a chest CT scan as part of the enrollment process (Sep. 10, 1999), three and one-half weeks before a first infusion with $6.6 \times 10^8$ cells (Oct. 5, 1999). A follow-up CT scan (Jan. 7, 1999), one month after a second infusion with $11.5 \times 10^8$ cells, revealed dramatic shrinkage in three separate lesions. Patient 13 also had an objective response as measured in pre and post CT scans. Paratracheal adenopathy went from $7.8 \text{ cm}^2$ (pre-study) to $4.4 \text{ cm}^2$ after cycle I, and disappeared following cycle II.

Presence of an Anergic State Did Not Preclude Ability to Generate CTLs or Prevent a Clinical Response Most of the patients treated under this protocol had received previous medical intervention. A pretreatment skin test was performed to determine if an anergic response to a panel of seven common antigens correlated with either an inability to generate CTLs ex vivo, or prevent a documented clinical response. The ability to generate CTLs ex vivo did not correlate with the patients pretreatment skin test results. It should be noted that patients 03 and 04 (both mixed responders) had repeat skin tests prior to the start of the second cycle and remained anergic.

EXAMPLE 3

Generation of HER-2/neu Specific CTLs Capable of Lysing Breast & Ovarian Tumor Cells We were interested in applying our CTL-generation technology to other tumor types to determine if all forms of cancer can be targeted with this approach. HER-2/neu is a proto-oncogene with homology to EGER that is amplified and over-expressed in many human cancers, largely adenocarcinomas of the breast, ovary and colon. It is often associated with aggressive disease and can be an indicator of a poor prognosis. It has been studied in several clinical trials as a possible target for these types of cancers.

In the early 1990's HER-2/neu HLA-A2.1 restricted peptide epitopes were identified either by computer-assisted peptide binding algorithms or by mapping CTLs isolated from ascites of ovarian cancer patients (Table 6).

A2 binders that are weak, as our experience in with melanoma-associated peptides suggests that weak class I binders generally generate potent CTLs which recognize tumor cells, if indeed they represent native T cell epitopes. The majority of the tumor-associated proteins that we target are self-antigens and as such would be expected to have the high affinity for the

TABLE 6

HLA-A2.1-Restricted HER-2/neu Peptides

| HER-2/neu Peptides | PRI # | Other ID# | Location | Sequence (SEQ ID NO) | Reference |
|---|---|---|---|---|---|
| 48-56 | 827 | D113 | EC | HLYQGCQVV (SEQ ID NO:13) | Disis et al., 1994 |
| 369-377 | 835 | E75 | EC | KIFGSLAFL (SEQ ID NO:8) | Fisk et al., 1995 |
| 650-658 | 838 | GP1 | TM | PLTSIISAV (SEQ ID NO:15) | Fisk et al., 1995 |
| 654-662 | 837 | GP2 | TM | IISAVVGIL (SEQ ID NO:14) | Peoples et al., 1995 |
| 773-782 | 861 | N/A | IC | VMAGVGSPYV (SEQ ID NO:16) | Lustgarten et al., 1997 |
| 789-797 | 826 | E90 | IC | CLTSTVQLV (SEQ ID NO:7) | Disis et al., 1994 |
| 851-859 | 862 | E89 | IC | VLVKSPNHV (SEQ ID NO:17) | Disis et al., 1994 |
| 971-979 | 863 | C85 | IC | ELVSEFSRM (SEQ ID NO:18) | Fisk et al., 1995 |

All of the peptides were synthesized, given an identification number (PRI#) and evaluated for the ability to generate CTLs ex vivo utilizing the same method we employed for melanoma-associated, T cell peptide epitopes. CD8 cells were isolated from normal donors to determine the ability to routinely generate CTLs ex vivo with *Drosophila* cells loaded with known CTL peptide epitopes. Peptides 826, 835, 861 and 863 had the highest frequency of CTL generation (Table 7).

TABLE 7

Frequency of HER-2/neu CTL Generation in Normal Donors

| Donor | 826 | 827 | 835 | 837 | 838 | 861 | 862 | 863 |
|---|---|---|---|---|---|---|---|---|
| 193 | + | | + | | | | | |
| 194 | + | − | + | − | − | + | − | + |
| 195 | + | | + | | | + | | + |
| 196 | + | − | + | − | − | + | | |
| 197 | + | − | + | − | + | + | − | + |
| 198 | − | − | + | − | + | + | − | + |
| 207 | + | | + | | | + | | + |
| 212 | + | | + | | | + | | + |
| 218 | + | | + | | | + | | + |
| 232 | − | | + | | | + | | − |
| 233 | + | | + | | | + | | + |
| 241 | | + | | | | + | | |
| 243 | | + | | | | + | | |

While transfected *Drosophila* cells have the unique ability to present up to ten different peptide epitopes (FIG. 10), we selected the four HER-2 peptides 826, 835, 861 and 863 due to the frequency of generating CTLs to these peptides ex vivo. These four different HER-2 peptides represent weak to moderate binders to the HLA-A2.1 molecule presented on the surface of the transfected *Drosophila* cells. We tend to include class I molecule that is seen with viral peptides. The low to moderate binders generally generate CTLs that lyse the tumor cells very efficiently. This was demonstrated with the MART-1 peptide which is a low affinity binder on the *Drosophila* cells (FIG. 3), yet represents an epitope that routinely generate potent CTLs capable of lysing both peptide-loaded target cells (T2), or more importantly, melanoma cells (Malme3M) (FIG. 12).

HER-2/neu is a member of the EGF-R family and functions as a growth factor receptor. HER-2 protein is expressed during fetal development in humans. In adults, the protein is weakly detectable in epithelial cells of many normal tissues. In normal cells the HER-2 gene is present as a single copy. Amplification of the gene and/or over-expression of the associated protein has been identified in many human cancers including breast, ovarian, uterine, stomach and adenocarcinoma of the lung. Sequence differences between HER-2 and EGF-R receptor are noted in Table 8. Three of the four HER-2 peptides we have evaluated have three or more amino acids changes between the two proteins. A single amino acid change is sufficient to discriminate between the two proteins.

TABLE 8

HER-2/neu Versus EGF-R

| PROTEIN | PEPTIDE # | SEQUENCE (SEQ ID NO) | # CHANGES |
|---|---|---|---|
| HER-2/neu | 835 | KIFGSLAFL (SEQ ID NO:8) | 5 |
| EGFR | | SISGDLHII (SEQ ID NO:37) | |

TABLE 8-continued

HER-2/neu Versus EGF-R

| PROTEIN | PEPTIDE # | SEQUENCE (SEQ ID NO) | # CHANGES |
|---|---|---|---|
| HER-2/neu EGFR | 861 | VMAGVGSPYV (SEQ ID NO:16) VAASVDNPHV (SEQ ID NO:38) | 5 |
| HER-2/neu EGFR | 863 | ELVSEFSRM (SEQ ID NO:18) ELIIEFSKM (SEQ ID NO:39) | 3 |
| HER-2/neu EGFR | 826 | CLTSTVQLV (SEQ ID NO:7) CLTSTVQLI (SEQ ID NO:40) | 1 |
| HER-2/neu EGFR | 689-697 | RLLQETELV (SEQ ID NO:41) RLLQERELV (SEQ ID NO:42) | 1 |

Once the CTLs have been generated after the four-week ex vivo stimulation protocol, we evaluated whether peptide specific cells were present using HLA-A2.1 tetrameric molecules prepared with the immunizing peptides. As demonstrated in FIG. 13, the ability to generate peptide-specific CTLs was donor-dependent. In Panel A (donor 261), the donor made a strong CTL response to peptide 835 (37.55%). In Panel B (donor 262), peptide-specific CTLs can be detected with both the 835 and 861 tetrameric molecules (3.6% and 15.1%, respectively). This supports the use of multiple peptides to guarantee peptide-specific CTLs at the end of the stimulation protocol. This ex vivo protocol allows one to generate multiple-specific CTLs relatively easily.

Anti-Peptide and Anti-Tumor Responses

After the completion of the full ex vivo protocol, the CTLs generated were evaluated for antigen-specificity. To generate the CTLs, on Day 0 Drosophila cells were loaded with a combination of the four HER-2 peptides. At the end of the four-week ex vivo stimulation protocol, the bulk CD8 culture was evaluated for antigen-specificity. T2 cells loaded with each of the immunizing peptides were used as target cells. In FIG. 14, a typical response is depicted. The bulk culture contains specificity for each of the four HER-2 peptides. The anti-tumor response was assessed on an ovarian tumor cell line (ATCC; HTB-77). When a target cell line is not HLA-A2.1-restricted, we transfected the cell line to have a +/−assay system. When HLA-A2.1 was transfected into the HTB-77 line, an enhanced killing by CD8 effector cells was noted (FIG. 15, Panels A to D). HER-2 specific effectors, representing the individual peptides were evaluated to confirm the presentation of each of the peptide epitopes on this tumor cell line.

A breast adenocarcinoma cell line (ATCC; HTB-131) transfected with HLA-A2.1 was also evaluated for the ability to demonstrate tumor lysis with the HER-2 specific peptide effectors. CTLs specific for peptide 861 could lysis this tumor cell line when transfected with HLA-A2.1 (FIG. 16).

IFNγ Treatment Required for Tumor Cell Lysis

The HTB-77/A2.1 cell line requires a pretreatment with IFNγ to demonstrate peptide-specific lysis. The cells were treated with 500 U/ml of IFNγ (specific activity of 25 ng/ml) for twenty-four hours prior to the initiation of the $^{51}$Cr-release assay. In FIG. 17, the addition of the IFNγ resulted in enhanced lysis of the HLA-A2.1 transfected cell line. To determine the effect of this dose of IFNg on the surface expression of both HLA-A2.1 and HER-2, a FACS analysis was performed to determine the levels of these molecules after both twenty-four and forty-eight hours of induction. FIG. 18, Panels A and B depict the FACS analysis results. In Panel A, there was no enhancement of the HER-2 molecule on the surface of the HTB-77 cells at twenty-four and forty-eight hours after induction with IFNg. In the HLA-A2.1 transfected cells, neither HER-2 nor HLA-A2.1 demonstrated an increase in surface level of expression after a similar treatment protocol. What was noted was an increase in the level of TAP-1 expression, as well as HLA-DM and -DR, Cathepsin S and D and Caspase 5, when the mRNA levels were evaluated by microarrary DNA chip analysis (FIG. 19). This would explain why there is an enhance killing of the HTB-77/A2.1 cells in the presence of IFNγ. An up-regulation of this particular molecule would result in more efficient processing of the HER-2 molecule, allowing better presentation of the peptides of interest Peptides Synthetic peptides were made by standard Fmoc chemistry using a peptide synthesizer (Gilson Company, Inc.) All peptides were purified to >95% purity by reverse-phase HPLC on a C-8 column. Purity and identity were established using a mass spectrometer with electrospray ionization. Melanoma-associated peptides included: peptide 819 was MART-1 specific (AAGIGILTV SEQ ID NO:6), 817 and 853 were both gp100 peptides (ITDQVPFSV SEQ ID NO:4 and KTWGQY-WQV SEQ ID NO:5, respectively), tyrosinase-specific peptides were 689 and 792, with 792 representing the post translational modified version (YMDGTMSQV SEQ ID NO:2) of the native sequence (YMNGTMSQV SEQ ID NO:1) represented by peptide 689. Peptides 826 (CLTSTVQLV SEQ ID NO:7) and 835 (KIFCSLAFL SEQ ID NO:8) represented HER-2/neu sequences from the intracellular and extracellular domains, respectively of the p185 protein. Pec60$_{20}$ (ALA-LAALLVV SEQ ID NO:10) Pec60$_{25}$ (ALLVVDREV SEQ ID NO:11) were overlapping sequences representing a mucinous protein detected in ovarian tumor lines. C-lectin also was a protein detected in ovarian tumor cell lines and a peptide from its sequence (C-lectin$_8$) is represented by KMASRSMRL SEQ ID NO:9.

In Vitro Cytotoxicity Assay

Standard $^{51}$Cr-release assays were performed to determine CTL effector cell recognition of melanoma-associated peptide epitopes loaded onto T2 cells. Harvest 3×106 T2 cells were grown in RPMI+10% FBS (media). 0.1mCi of $^{51}$Cr was added and incubated at 37° C. in a water bath. Labeled cells were added to 10 ml of 4% wash (RPMI+4% FBS) and pellet, washed two additional times, and re-suspended in media to a final concentration of 0.2×106/mL to record radioactivity of spontaneous versus detergent lysed cells. The cells were pulsed with the appropriate peptide(s) at 20 µg/mL for thirty minutes. 50 µL was added to each 96-well plate each containing CD8 effector cells at 10, 2, 0.4, and 0.08×10$^6$/mL, which was incubated at 37° C. for six hours, spun and harvested for supernatant.

Flow Cytometry and Tetramer Staining

The cells were labeled with FITC- or PE conjugated monoclonal antibodies by incubation at 4° C. for 30 minutes in FACS buffer (1% BSA, 0.02% NaN$_3$ in PBS), followed by a wash in the same buffer. Cells were fixed in 0.5% formaldehyde prior to data acquisition and analysis on a FACScan flow cytometer (Becton Dickinson) with its CellQuest software. Nonspecific staining was measured with the same secondary antibody used to label purified primary antibodies, or an isotype-matched control when the primary antibodies were directly labeled. Tetrameric staining was performed with HLA-A2.1 specific HIVgag tetrameric molecules (Beckman Coulter) harboring the sequence SLYVTVATL SEQ ID NO:43 as a negative control. HER-2 specific tetramers were made with the sequences CLTSTVQLV (826 SEQ ID NO:7), KIFGSLAFL (835 SEQ ID NO:8), or VMAGVGFSPYV (861 SEQ ID NO:16) peptides. PE-labeled tetrameric HLA-A2.1-peptide complexes were used in conjunction with fluorescein isothiocyanate (FITC)-labeled anti-human CD8a (BD PharMagin) monoclonal antibodies to stain epitope-specific CD8+ T cells as described in package insert. Samples were analyzed by two-color flow cytometry on a Becton Dickinson FACScan, and gated CD8+ T cells were examined for staining with tetrameric HLA-A2.1-peptide complexes.

EXAMPLE 4

Generation of Additional Breast and Ovarian Specific CTLs with This Ex Vivo Stimulation Protocol We have demonstrated the ability to generate CTL responses to all known HLA-A2.1-restricted peptide epitopes for several tumor antigens of different tumor origins. Our initial studies focused on melanoma where we were able to demonstrate objective clinical responses in patients treated with CTLs specific for four different peptide epitopes specific for the MART-1, gp100 and tyrosinase melanoma-associated proteins [Richards et al., *Amer. Soc. Clip. Oncol.*, San Francisco, Calif. (2001, May)].

To extend the ability to raise CTLs to other tumor antigens present in a wide variety of other cancers we have selected published and novel sequences to tumor antigens common to several different tumor types. These include AES, MUC-1, CEA, FBP, C-Lectin, NY-ESO-1, Pec60, CA-125, MAGE-3, telomerase and G250. Table 10 describes these antigens, the frequency of expression and the cancers, which express them. The frequency of response to these peptides with our ex vivo stimulation protocol is listed in Table 9.

TABLE 9

Frequency of Response to Breast and Ovarian Peptide Epitopes in Normal Donors

| Donor | 879 | 893 | 894 | 899 | 900 | 901 | 902 | 903 | 906 | 907 | 908 | 909 | 910 | 911 | 912 | 913 | 914 |
|---|---|---|---|---|---|---|---|---|---|---|---|---|---|---|---|---|---|
| 248 | + | + | + | | | | | | | | | | | | | | |
| 249 | + | + | + | | | | | | | | | | | | | | |
| 250 | + | − | + | | | | | | | | | | | | | | |
| 251 | − | − | + | | | | | | | | | | | | | | |
| 252 | + | − | + | | | | | | | | | | | | | | |
| 253 | − | − | + | + | | | | | | | | | | | | | |
| 254 | + | − | + | + | | | | | | | | | | | | | |
| 255 | | | | | | − | + | + | − | + | + | + | + | | | | |
| 256 | | | | | | + | − | + | + | + | + | − | + | | | | |
| 257 | | | | | | | | | | | | | | + | + | + | |
| 259 | | | | | | | | | | | | | | + | − | − | |
| 260 | | | | | | − | − | − | − | | | | | | | + | |
| 261 | | | | | | | | | | + | + | + | + | | | | |
| 262 | | | | | | | | | | + | + | − | + | | | | − |
| 265 | + | + | + | + | − | − | − | − | + | | | | + | + | | − | |

TABLE 10

Tumor Antigen Descriptions

| Antigen | Description |
|---|---|
| CA-125 | Cancer Antigen 125 is an epithelial cell marker expressed by ovarian tumors and some ovarian cell lines. About 85% of ovarian cancer patients have an increased serum CA125 and is therefore commonly used as a serum tumor marker. (*Cancer Letters* (1999, October) 145(1-2) pg. 133-141) |
| MUC-1 | Mucin is a transmembrane glycoprotein expressed on both normal and malignant epithelium. The underglycosylated form of MUC-1 over-expressed on the cell surface of many human adenocarcinomas such as breast and ovarian cancer, as well as hematological malignancies including multiple myeloma and B-cell lymphoma. (*Blood* (1999, June) 93(12) pg. 4309-4317) |
| G250 | A renal cell carcinoma associated antigen expressed in 85% of RCC's but not normal kidney tissue. It is identical to the tumor-associated antigen MN/CAIX which is expressed in about 50% of invasive breast cancers. (*Cancer Research* (1999, November); 59(21) pg. 5554-5559) |
| FBP | Folate binding protein is a receptor involved in folate transport. It is over-expressed in over 90% of ovarian tumors and 20-50% of breast cancers. (*Anticancer Research* (1999 July-August) 19(4B) pg. 2907-2916) |
| HER-2/neu | A proto-oncogene (HER-2) encoding a transmembrane protein similar in sequence and structure to EGF-R. HER-2/neu is over-expressed as much as 200 fold over normal tissues in breast and ovarian tumors. It has also been identified in renal cell and lung carcinomas. (*J. Exp. Med.*(1995, June) Vol. 181, pg. 2109-2117) |
| NY-ESO-1 | A cancer-testes antigen found in 30% of breast, prostate and ovarian cancers, lung cancer, bladder cancer, head and neck cancer and melanoma. Patients who have cancers with tumors expressing this antigen usually have circulating antibodies against it as well. (*J. Immunology* (2000) vol. 165 pg. 948-955) |
| CEA | Carcinoembryonic antigen is a tumor-associated antigen frequently expressed in epithelial tumors (colon, breast, lung). CEA levels in the serum can correlate with disease stage and is used to monitor treatment and reoccurrence of disease. (*Human Immunology* (1998) vol. 59 pg. 1-14) |

TABLE 10-continued

Tumor Antigen Descriptions

| Antigen | Description |
|---|---|
| MAGE-3 | A cancer-testis antigen expressed on 70-80% of metastatic melanoma lesions and cell lines. It is a member of the family of melanoma associated or MAGE proteins. In addition, MAGE-3 has been found in 20-60% of epithelial tumors (colon, breast, lung, gastric carcinomas).<br>(*Human Immunology* (1998) vol. 59 pg. 1-14) |
| AES | The amino enhancer of split protein is part of a set of transcriptional repressors encoded by the Enhancer of split genes. This tumor antigen was identified in tumor-associated lymphocytes of ovarian and breast tumors.<br>(*Molecular Immunology* (1998) 35(17)pg. 1121-1133) |
| HTR | Telomerase(hTR) is a specialized type of reverse transcriptase (hTRT or hTERT) that catalyzes the synthesis and extension of telomeric DNA. The activity of this enzyme is elevated in about 90% of all human tumors including cancers of the breast, thyroid, bladder, cervix, prostate, colon, pancreas and stomach.<br>(*Cancer Research* (2001, December) 61(23)pg. 8366-8370) |

EXAMPLE 5

Treatment of Malignant Melanoma Using CTL Infusion Coupled with Interferon and Interleukin-2

Purpose of The Study

This example teaches the effectiveness of cytotoxic T cell infusions in the treatment of melanoma as assessed according to the following factors:

1. establish the efficacy of re-infused autologous CTLs after in vitro immunization with *Drosophila* cells, transfected with human class I and co-stimulatory molecules and loaded with melanoma-associated peptide epitopes;
2. establish the safety and tolerability of administration of interferon-α-2b (IFN-α), interleukin-2 (IL-2) and autologous CTLs generated ex vivo by immunization with *Drosophila* cells, at the doses and on the schedule prescribed;
3. determine if tumor-infiltrating T cells are present in tumor biopsies, post treatment;
4. demonstrate the presence and persistence of antigen-specific CD8 cells in the peripheral blood of treated patients;
5. confirm that five (5) consecutive, daily subcutaneous injections of IFNα (10Mu/m$^2$), can up-regulate Class I and melanoma-associated antigens on the surface of melanoma in vivo.

An outline of the clinical study CTL-03 is presented in FIG. 20.

Patient Populations

Eligibility for treatment required patients to have histologically-documented, unresectable malignant melanoma that was measurable and readily subject to evaluation. In addition, patients were required to have an HLA-A2 haplotype. Pre-treatment evaluation included radiologic evaluation of the brain by MRI or CT scan, CT scanning of the chest and abdomen, and physical examination, especially of the skin and lymph nodes. The total number of patients to be enrolled is 42. Twenty-one (21) patients are on the control cytokine only arm and twenty-one (21) patients are on the cytokine+T cell therapy arm. Thirty-one (31) patients have been enrolled to date (17 entered on the control arm and 14 have entered on the T cell treatment arm). Patients who progress on the control arm are offered a cross over to the T cell arm if they desire (11 patients crossed over). The total number of patients treated to date is thirty-one (31) (16 male, 15 female). The ages ranged from 27 to 80 years with an average of 52 years. Patients were screened for the HLA-A2 haplotype by FACS analysis with an HLA-A2 specific monoclonal antibody (ATCC: BB7.2).

Subtyping was performed by PCR analysis. All patients, with the exception of two, were HLA-A*0201-positive. The other HLA-A2 subtypes were HLA-A2*0202 and HLA-A2*0205.

Administration of Drugs

Interferon-α-2b (Intron-A®; recombinant interferon alfa-2b, Schering Corporation, Kenilworth, N.J.) was administered subcutaneously to the patient at 10 MU/m$^2$ for 5 consecutive days prior to the CTL infusion. Ex vivo *Drosophila* cell-activated autologous lymphocytes (1–10×10$^9$) were infused to the patient on the day after INF-α administration. Interleukin-2 (PROLEUKIN®; Aldesleukin, recombinant IL-2, Chiron Corporation, Emeryville, Calif.) was administered subcutaneously to the patient at 3 MIU daily immediately following the CTL infusion and continued for another 27 consecutive days.

Table 11 shows a comparison of the cytokine dose used in study CTL-03 with those used in FDA approved protocols for the single administration of IFN-α in the adjuvant setting (post surgical remove of all detectable tumor) or high dose IL-2.

TABLE 11

A Comparison of The Cytokine Dose Used in Study CTL-03 with Those Used in FDA Approved Protocols

| Study | IFN-α<br>(INTRON ®A; Interferon alfa-2b, recombinant) | IL-2<br>(PROLEUKIN ®;<br>Aldesleukin,<br>recombinant IL-2) |
|---|---|---|
| IFNα Adjuvant Therapy | 20M IU/m$^2$ IV, for 30 consecutive days,<br>10 MU/m$^2$ SC, 3X/Wk for 48 weeks | |
| IL-2 High Dose (HD) therapy | | 720 × 10$^3$ IU/kg IV every 8 hours until Grade III or IV toxicity reached |
| CTL-03 | 10M IU/m$^2$ SC, for 5 consecutive days; prior to a single T cell infusion | 3 MU SC, for 28 consecutive days; initiating immediately after a single T cell infusion |

In Vitro Immunization of Purified CD8 Cells

Primary Stimulation

Transfected *Drosophila* S2 cells are incubated in Schneider's medium (10$^6$ cells/mL) supplemented with 10% fetal calf serum and copper sulfate at 27-28° C. for 24-72 hours. S2 cells are harvested, washed and re-suspended in Insect X-press medium (BioWhittaker) containing 0.1 µg/mL of each peptide; human tyrosinase 369-377 (SEQ ID NO:1 YMNCTMSQV and SEQ ID NO: 2 YMDGTMSQV), gp100 209-217 (SEQ ID NO: 4 ITDQVPFSV), gp100 154-162 (SEQ ID NO: 5 KTWGQYWQV) and MART-1 27-35 (SEQ ID NO: 6 AAGIGILTV) and 5 µg/mL human β2 microglobulin. Following incubation at room temperature (23-25° C.) for three-four hours, the S2 cells are mixed with CD8+ cells at a ratio of 1:10 (in Roswell Park Memorial Institute (RPMI) medium (a defined medium, Gibco) supplemented with 5-10% autologous serum. The cell mixture is incubated for four days at 37° C. during which tine the *Drosophila* cells die off. On day four or five, IL-2 (20 U/mL) and IL-7 (30 U/mL) are added with a media change to selectively expand the antigen-specific CTL population consisting of cells with specificity for the melanoma-associated antigens (MART-1, gp100 and tyrosinase).

Restimulation

Autologous, CD8-depleted PBMCS, obtained at the time of leukapheresis and frozen for future use, are thawed, washed and resuspended at $10^6$-$10^7$ cells/mL (depending on the number of CD8-depleted PBMCs collected at the time of the CD8 isolation step) in RPMI medium containing 10% autologous serum, 5 µg/mL recombinant, human β2 microglobulin and 5-20 µg/mL (depending on the total number of peptides to be added) of tyrosinase, gp100 and MART-1 peptides that were used in the stimulation described supra. Following γ-irradiation (5,000 rads), the cells are incubated at 37° C. for two hours. Non-adherent cells are removed by washing with Dulbecco's PBS. Adherent monocytes are loaded with the five peptide epitopes described supra by incubation for 90 minutes in Leibowitz medium containing 5 µg/mL human β2 microglobulin in 1% HSA (in place of autologous serum, to avoid the possibility of introducing potential proteases, which might be present in the serum) and 5-10 µg/mL of each of the five peptide epitopes. The supernatant is removed and the *Drosophila*-activated CD8 cell suspension (2.5×10⁶ cells/mL in RPMI medium with 10% autologous serum) is added at a ratio of 10 CD8 cells to 1 adherent monocyte. After three to four days of culture at 37° C., IL-2 (20 U/mL) and IL-7 (30 U/mL) are added with a medium change to selectively expand the melanoma-specific CTL population. A total of two of such adherent cell, peptide-specific restimulation steps take place, one approximately one week after the primary stimulation, and the second approximately one week later. A non-specific expansion step occurs at the start of week 4 of the ex vivo protocol.

Non-specific Expansion

The CD8+ effector cells that have undergone two rounds of restimulation are expanded in cell culture bags along with feeder cells (irradiated non-CD8+ selected cells) after being stimulated with OKT3 antibody. Frozen non-CD8+ selected cells are thawed, washed and then gamma irradiated (3500 rads). A ratio of 4:1 (feeder:effector) is placed in T-225 flasks that have been coated with OKT3 antibody. OKT3 stimulation is performed ion complete RPMI medium containing 10% autologous serum supplemented with 20 U/mL of IL-2. Two days later the stimulated T cells are diluted with fresh media and transferred to cell culture bags for expansion. Fresh media and IL-2 are supplemented approximately every two days to feed the rapidly expanding T cells.

Phenotypic Analysis of CD8 Cells Post Ex Vivo Stimulation Protocol

Phenotypic analysis, as measured by flow cytometry, was performed on purified CD8+ cells on the day of isolation from the leukapheresis sample and on the day the cells were released for infusion back into the patient. A statistical analysis was performed with samples from patients and from normal donors, which had undergone the same ex vivo stimulation protocol. Statistical significant differences were found between the naïve CD8+ samples and the CD8+ effector cells obtained at the end of the ex vivo stimulation protocol, regardless if the samples were derived from patients or normal donors.

Activation markers (e.g., CD69, which is not expressed on resting lymphocytes but is rapidly induced upon activation; HLA-DR a class II molecule expressed on activated T cells), memory markers (e.g., CD45RO expressed on activated cells and most memory cells) integrin markers (e.g., CD49d/CD29, which is involved in the migration of lymphocytes from blood to tissues at sites of inflammation), accessory molecules (e.g., CD11a/CD18; which aids in cytotoxic lymphocyte killing and mediates adhesion to many cells including endothelium) and cytokine receptor markers (e.g., the functional high affinity IL-2R receptor is composed of a non-covalenty associated CD25/CD122/CD132 heterodimer) were all found to be upregulated on the CD8 effector cells following the completion of the ex vivo stimulation protocol. Table 12 summarizes the results of the analysis.

TABLE 12

Phenotypic Analysis of CD8+ Cells Post Ex Vivo Protocol

| Marker | Pairs | Fold change Naïve/FAA | 95% Confidence | | 99% Confidence | |
|---|---|---|---|---|---|---|
| | | | From | To | From | To |
| CD69-F | 51 | 7.35 | 5.78 | 9.33 | 5.33 | 10.00 |
| CD25-F | 51 | 5.64 | 4.97 | 6.40 | 4.76 | 6.68 |
| CD49d-PE | 51 | 4.79 | 4.29 | 5.33 | 4.13 | 5.53 |
| CD8-F | 50 | 4.59 | 3.98 | 5.31 | 4.13 | 5.12 |
| HLA DR-PE | 51 | 3.78 | 2.96 | 4.82 | 2.73 | 5.22 |
| CD11a-F | 51 | 3.56 | 3.24 | 3.92 | 3.13 | 4.05 |
| CD18-PE | 51 | 3.32 | 2.99 | 3.68 | 2.89 | 3.81 |
| CD45RO-F | 51 | 2.89 | 2.47 | 3.39 | 2.34 | 3.57 |
| CD29-F | 51 | 2.82 | 2.49 | 3.19 | 2.38 | 3.33 |
| CD132-PE | 22 | 2.75 | 2.17 | 3.49 | 1.99 | 3.81 |
| HLA ABC | 47 | 2.26 | 2.04 | 2.51 | 1.96 | 2.60 |
| CD3-F | 44 | 2.14 | 1.91 | 2.39 | 1.84 | 2.49 |
| TCRαβ | 50 | 2.05 | 1.78 | 2.37 | 1.69 | 2.49 |
| CD122-PE | 21 | 1.54 | 1.15 | 2.07 | 1.03 | 2.31 |
| CD44-F | 51 | 1.00 | 0.86 | 1.16 | 0.82 | 1.21 |
| CD28-F | 51 | 0.92 | 0.77 | 1.10 | 0.72 | 1.16 |
| CD62L-F | 51 | 0.77 | 0.63 | 0.94 | 0.59 | 1.00 |
| CD16-PE | 28 | 0.45 | 0.32 | 0.62 | 0.29 | 0.69 |
| CLA | 45 | 0.42 | 0.33 | 0.53 | 0.31 | 0.57 |
| CD45RA-F | 51 | 0.31 | 0.26 | 0.38 | 0.24 | 0.41 |

The results of the phenotypic analysis support that the CD8+ effector cells are activated by the ex vivo protocol described herein. These activated CD8+ effector cells are capable of migrating from blood to the tumor sites in vivo and are capable of killing the tumor target cells with exquisite sensitivity and potentially can proliferate in the presence of a low dose of IL-2 as the high affinity IL-2R is present on these cells. CD122 is constitutively expressed on a subpopulation of resting T cells. In table 12, the white areas are statistically significant values, which are upregulated after completion of the CD8+ ex vivo stimulation protocol. The light gray areas do not show significant upregulation or downregulation. The dark gray areas show a statistically significant downregulation of the reported molecules. Regulation of these markers is consistent with the induction of activated T cells fully capable of tracking and lysing tumor cells in vivo, as measured by phenotypic analysis.

Flow Cytometry Obtain approximately 1×10$^7$ of purified CD8+ cells from the donor leukapheresis. Place each sample in sterile tubes at 1×10$^6$ per 100 μl of wash buffer (PBS+1% BSA+0.02% NaN3). In each tube with 100 μl of cell suspension, add 10 μl of the appropriate antibody either directly labeled with FITC or PE or if primary antibody is unlabeled, follow with adding a labeled secondary antibody (goat anti-mouse IgG). Incubate each antibody step at 40° C. for 30 min. Wash with 1-2 mL of wash buffer between each antibody step. Pellet cells for 7 minutes at 600×g. Discard supernatant. Resuspend each cell pellet in 0.5 ml of 0.5% formaldehyde/PBS fixative and read on a FACScan (Becton Dickinson) flow cytometer at the appropriate settings.

Up-Regulation of Class I and Melanoma-Associated Antigens in Response to administration of IFN-α-2b From a clinical study described in Example 2 herein, it was noted that a five day course of IFN-α-2b (Intron-A®) administered subcutaneously at 10 MU/m$^2$ on days 17-21 of the clinical protocol was sufficient to up-regulate both HLA (class I) expression and melanoma-associated antigen expression, two key requirements for recognition and lysis by antigen-specific T cells. This finding was recorded in sequential biopsies obtained from a single patient (04-M) with multiple subcutaneous skin lesions available for analysis. The four samples were labeled (A) pretreatment; (B) post initiation of IFNα treatment (5 consecutive doses); (C) post CTL infusion 1 and (D) post infusion 2. Results from immunohistochemistry analysis on expression of HULA (HLA-A2.1) and melanoma-associated antigen (MART-1) from the four biopsy samples are summarized in Table 13, wherein higher number indicates a higher level of expression of the respective protein. The results showed that there was no additional increase in expression of HLA (HLA-A2.1) and melanoma-associated antigen (MART-1) after the first five consecutive days IFN-α treatment, indicating that interferon-α2b treatment beyond 5 consecutive days was not necessary to reach optimal levels of HLA-A2.1 and MART-1 expression.

TABLE 13

Five Consecutive Days Interferon-α-2b Treatment Was Sufficient to Obtain Optimal Levels of HLA-A2.1 And MART-1 Expression

| Patient | Biopsy Sample | Time Point | HLA-A2.1 | MART-1 |
|---|---|---|---|---|
| 04-MJ | A | Pretreatment (No IFNα) | 1-2$^+$ | 1$^+$ |
|  | B | Post 5 days IFNα; Pre T cell therapy | 4$^+$ | 4$^+$ |
|  | C | Post 11 days IFNα; Post a single T cell infusion | 4$^+$ | 4$^+$ |
|  | D | Post 17 days IFNα; Post 2 doses of T cell therapy | 4$^+$ | 4$^+$ |

Immunohistochemical staining Biopsy samples were shipped overnight at 4° C. in RPMI media. The tissue was placed in OCT® (Tissue-Tek) embedding medium for frozen tissue specimens. The tissue: OCT matrix was placed on filter paper prior to a quick-freezing step in liquid NO$_2$. Frozen samples were stored at −80° C., prior to sectioning. Cryostat sections (5 μm) were placed on Superfrost™ (Fisher) charged slides. Slides were fixed in cold acetone (−20° C.) and stored at −80° C. until stained. Endogenous peroxidase activity was blocked by incubating in 0.3% H$_2$O$_2$ in methanol for 10 minutes. Primary antibody was added for 1 hour in a humidified chamber. Biotinylated secondary antibody was added and incubated for 30 minutes at room temperature. Streptavidin-HRP was added under the same conditions. DAB substrate was added for up to 5 minutes and rinsed in water. Slides were hydrated through 4 cycles of alcohol (70-95-95-100%), followed by 3 cycles of xylene. Antibodies used in the immunohistochemical analysis were from ATCC (pan HLA class I, W6/32 and HLA-A2-specific, BB7.2), or NeoMarkers (MART-1, M2-7C10).

Increase in Cell Numbers with Repeat Cycles of Treatment

In clinical study CTL-03 it was noted that cell counts recorded at day 6 of the in vitro culturing cycles, increased rather than decreased, as was detected in CTL-02 at each cycle of treatment (FIG. 21). FIG. 21A represents a typical growth curve for the ex vivo generated CD8+ cells in the CTL-02 study. A typical drop at day 6 reflected the dying off of non-specific cells. The CD8 cells from each cycle of retreatment for patient 15-RT had similar growth curves, suggesting that there were no memory cells remaining in the peripheral blood after each cycle of treatment. This was not the case in study CTL-03. The typical drop in cell numbers is noted with 01-KN-1, reflecting the drop seen in the cells obtaining during the first cycle. However, when cell counts were performed on cells obtained at the start of cycle 2 and 3 (FIG. 21B; 01-KN-2 and 01-KN-3) the growth curves were more representative of the presence of memory cells. This was noted in all patient samples that were from second and third cycles of treatment in study CTL-03. This result can be attributed to the addition of IL-2 to patients at the time of the CTL infusion, and 27 days post the CTL infusion.

Cell Counts A 0.2% solution of Trypan Blue was prepared. Count cells were performed using a hemacytometer. Counts of at least 100 viable (unstained cells) in at least 1 full square (9, 1 mm squares total) were recorded. The number of live cells were recorded and the number of full 1 mm squares counted. The number of cells/square. The calculation for determining cells/mL is: (number of cells/1 mm square) (dilution factor) (1×10$^4$)=cells/mL.

Tetramer Analysis Confirms the Presence of Antigen-Specific T Cells Post CTL Infusion For study CTL-03, tetrameric molecules containing either MART-1 or gp100 melanoma-associated peptides were commercially available for analysis of antigen-specific T cells (Beckman Coulter; Immunomics). These tetrameric molecules were not available for study CTL-02. In six (6) patients who underwent a second cycle of therapy in study CTL-03, as shown in FIG. 22, 6/6 patients had increases in the level of MART-1 specific T cells from the time of the first leukapheresis sampling to the start of the second cycle of treatment, which is generally a two month period. When gp100 tetrameric molecules were used to evaluate antigen-specific T cells, 5/6 patients had elevated gp100 specific T cells at the time of the second leukapheresis (FIG. 22). Initiation of a leukapheresis procedure marks the start of a cell therapy cycle. In one patient (15-DC) a total of 6 cycles of T cell therapy was performed. While each cycle was separated by approximately two (2) months, the time frame between cycle 4 and 5 was five (5) months as the patient wanted to take time off for a vacation. The antigen-specific T cells for MART-I and gp100 at the start of cycle 4 were 0.26% and 0.65%, respectively. When the CD8 cells were evaluated at the start of cycle 5 the antigen-specific cells for MART-1 were 0.29% and 0.46% for gp100. This would suggest that the antigen specific cells were being maintained in vivo, even after the cytokine and cell therapy were suspended.

Tetrameric Staining Approximately $1 \times 10^7$ of purified CD8+ cells were obtained from the donor by leukapheresis. Each sample was placed in sterile tubes at $1 \times 10^6$ per 100 µl of wash buffer (PBS+1% BSA+0.02% NaN3). In each tube with 100 µl of cell suspension 5 µl of the HLA-A2.1-tetramer-streptavidin-phycoerythrin (SA-PE) labeled molecules (loaded with the peptide of interest (MART-1, gp100 or Tyrosinsase-specific) was added and was incubated at room temperature for 30 minutes. Anti-CD8+ monoclonal antibody (FITC-labeled) was added and the incubation was continued for an additional 30 minutes. 1-2 mL of wash buffer was used to wash the samples at the end of the incubation period. Cells were pelleted for 10 minutes at low speed (400×g) and the supernatant was discarded. Each cell pellet was resuspended in 0.5 ml of 0.5% formaldehyde/PBS fixative and read on a FACScan (Becton Dickinson) flow cytometer at the appropriate settings.

Correlation Among Three Different In Vitro Assays Used to Measure Cytolytic Activity, Antigen-Specificity and Cell Proliferation With the advent of the tetrameric technology to evaluated antigen-specific cells, many publications reported significant numbers of antigen-specific T cells in the peripheral blood of melanoma patients (Lee et al., *Nature Medicine* (1999) 5:677-685). When these antigen-specific cells were isolated and attempts made to expand the cells in an antigen-specific manner, there was a tremendous amount of failure. While tetrameric staining will allow one to detect the presence of antigen-specific T cells, additional assays such as CTL lysis assays are useful to determine if the cells can properly kill peptidespecific targets. Intracellular interferon gamma assays can be used to determine whether the cells can proliferate in response to antigen. These three assays were run on the final CD8+ T cell product (FIG. 23) to ensure that the number of antigen-specific T cells detected accurately reflects the number of T cells which are capable of lysis the tumor cells in vivo and will proliferate in response to antigenic stimulation.

Interferon GAMMA MEASURED in Cell Supernatants Post Primary Stimulation (Day 6) Increases with Repeat Cycles of T Cell Therapy Another indication that the IL-2 was having dramatic effects on T cell persistence in vivo was noted by measuring IFN gamma production in cell supernatants (FIG. 24). Six (6) days after the primary stimulation with *Drosophila* cells in each of the treatment cycles, cell supernatants were collected and evaluated for the level of interferon gamma, a cytokine released by CD8+ cells in response the antigen-specific stimulation. In repeat cycles of four (4) patients, it was noted that the level of IFN gamma production, at this time frame, increased with each round of T cell therapy. IFN gamma levels were low to non-detectable in all instances. With each additional round of T cell therapy, higher levels of IFN gamma were detected suggesting that greater number of antigen-specific T cells were present in the CD8+ populations, isolated at the time of each leukapheresis.

Detection of T Cells Infiltrating Tumor Cells

In one patient (04-AD), who had undergone three (3) cycles of cytokine and T cell therapy in the CTL-03 study, a biopsy of a skin lesion was obtained six (6) weeks following the end of the third cycle. The presence of Class I and melanoma-associated antigens MART-1 and gp100 were present on immunohistochemical staining analysis. The presence of infiltrating T cells (CD3+) was also noted. Positive immunohistochemical staining of the tumor suggests that the class I and melanoma-associated antigens were maintained and/or upregulated by the five (5) day dose of IFNα. The presence of these markers on the melanoma cells allows the antigen-specific T cells to lyse the tumor cells in an antigen-specific manner. The presence of infiltrating T cells within the tumor mass, six weeks after a T cell infusion suggests that the T cells are persisting in vivo, if indeed these T cells represent a subset population of the T cells infused.

In Vitro Cytotoxicity Assay Standard $^{51}$Cr-release assays were performed to determine CTL effector cell recognition of melanoma-associated peptide epitopes loaded onto T2 cells. $3 \times 10^6$ T2 cells (TAP-deficient, HLA-A2.1 positive) were grown in RPMI+10% FBS (media) and harvested. 100 mL of $^{51}$Cr per target was added and incubated at 37° C. in a water bath. Labeled cells were added to a volume of 10 mL of 4% wash (RPMI with 4% FBS) and pelleted. Washes were performed 2 additional times. The cells were resuspend in media to a final concentration of $0.2 \times 10^6$/mL and radioactivity of spontaneous versus maximum (detergent-lysed) cells was recorded. The cells were pulsed with the appropriate peptide(s) at 10-20 µg/mL for 30 minutes. 50 µL/96 well plate each containing CD8+ effector cells at different effector:target ratios. The mixture was incubated at 37° C. for 6 hours. Plates were spun and harvest supernatant. Radioactive supernatants were counted in a Cobra gamma counter. Specific $^{51}$Cr release was calculated using the formula ($^{51}$Cr release-Spontaneous release)/(Maximum release—Spontaneous release)×100.

Intracellular gamma interferon assay Effector cells are stimulated with peptide-pulsed T2 cells (ratio of CD8:T2 was 2:1) for 5 hours in the presence of GlogiStop (PharMingen). Stimulated cells were surfaced stained with anti-CDS-PE, fixed and permeabilized with Cytofix/Cytoperm (PharMingen Cat no 2076KK), followed by staining with anti-IFN□-FITC. The dual-labeled cells were analyzed by flow cytometry (Becton Dickson FACScan) and expressed as a percent of maximum expression. Maximum expression of IFN□□ was measured as the amount expressed in response to OKT3 (Orthoclone) activation of the same effector cells.

Toxicity Associated with Biological Response Modifiers

The aim of clinical research with biological response modifiers (e.g., IFNα and IL-2) is to determine the optimum conditions that maintain the benefit of treatment, while reducing toxicity to a minimum level. Although IFN-α-2b at currently approved doses and schedules of administration can significantly prolong survival in melanoma patients. Administration can also be associated with severe toxicity. High doses of IL-2 appears to be more effective than low dose continuous infusions, yet high doses of IL-2 are also more toxic. The most common side effects are flu-like symptoms. The most severe side effects are hypotension, capillary leak syndrome, and reduced organ perfusion. IL-2 has been used clinically for both renal cell carcinoma and malignant melanoma. The combination of IFN-α-2b and IL-2 in low dose, subcutaneous regimens has been described in other clinical settings (Pectasides et al., *Oncology* (1998) 55:10-15; Piga et al., *Cancer Immunol Immunotherapy* (1997) 44:348-351).

In one study (Pectasides, 1998, supra), IFN-α-2b and IL-2 were administered in a 3-drug combination immunochemotherapy regimen in metastatic renal cell cancer (RCC) patients. The phase II study was carried out to define the activity of low dose subcutaneous administration of IL-2 [4.5 mU×2/24 h thrice weekly for 2 wk] and IFN-α-2b [3MU/24 h thrice weekly (on alternating days with IL-2) for 2 wk] and vinblastine (VLB) [4 mg/m2 every 3 weeks]. Patients had a one-week rest from cytokines, at which time they received the VLB. Treatment was repeated every 3 weeks, with a maximum duration of 1 year. Toxicity was mild to moderate (Grade I and II), consisting of fever, anorexia, malaise and nausea-vomiting in >80% of the patients. None of the patients experienced major VLB-related toxicity. It was proposed that the 3-drug combination might be a promising regimen (overall response rate of 38.7%) with modest toxicity in advanced RCC.

In another study (Piga, 1997, supra) evaluating low dose IFN-α-2b and IL-2 in RCC, IFN-α-2b [3MU/m2 daily, intramuscularly continuously] and IL-2 (0.5MU/m2×2/24 h subcutaneously on days 1-5 for the first week and 1MU/m2×2/24 h for 5 days in the following 3 weeks were prescribed. Side effects were said to be low (Grade I and II) in most of the patients, with abnormalities in liver and renal function tests noted. While the regimen was said to be of moderate toxicity, low cost and required no hospitalization, the flu-like syndrome observed in most patients was sufficient enough to cause one-third of the patients to refuse subsequent treatment.

Side effects from the IFNα and IL-2 regimen described for the CTL-03 study was considered mild to moderate effects similar to those detected in the RCC studies mentioned above. However, our cytokine regimen lasts a total of 33 days (5 with IFNα and 28 with IL-2) making it more attractive if the desired results can be achieved in this shorter time frame. In clinical study CTL-02 we were able to reach our desired effect with a five (5) consecutive day dosing and the additional eleven doses were not needed. In study CTL-03, only one out of 31 patients enrolled in the study refused to complete a single cycle of cytokine therapy. Overall the IL-2 dose was well tolerated by most patients.

Amounts of Cytokines Required to Reach Desired Effects

In a phase I study, the minimum dose of IL-2, in a combined immunotherapy protocol administering granulocyte macrophage colony-stimulating factor (GM-CSF) and IFN-α-2b in addition to IL-2, was 2-4 MIU/m2, subcutaneously for 12 days every 3 weeks. Immune activation was monitored and significant increases in lymphocytes, activated CD4+ and CD8+ T cells, NK cells, and monocyte DR expression were found 27. The dosing of the IL-2 in this study was similar to what we have used in study CTL-03 (3MIU administered subcutaneously daily for four consecutive weeks), however, we have the added benefit of providing the patients with significant numbers of antigen-specific T cells at the initiation of the IL-2 treatment.

Another study was initiated to evaluate the influence of a concomitant administration of the pineal hormone melatonin (MLT) and low-dose IL-2 in cancer patients who had progressed during a previous immunotherapy with IL-2 alone. The advanced solid tumors included lung, kidney, stomach, liver and melanoma. The IL-2 was administered at a daily dose of 3MIU, subcutaneously for 6 days/week for 4 weeks; a dosing that is almost identical to the one used in CTL-03. The MLT was given orally at a daily dose of 40 mg/day, starting 7 days prior to IL-2. Objective tumor regression was noted in 3/14 patients (21%). Patients with stable disease, or demonstrating a response, were associated with significantly higher increases in lymphocyte and eosinophil mean numbers, with respect to patients with disease progression indicating that advanced solid neoplasms resistant to IL-2 might become responsive to IL-2 therapy by a concomitant administration of MLT. It is possible that MLT enhanced the anti-tumor immune effect of IL-2 and/or increased the susceptibility of the cancer cells to cytolysis mediated by IL-2 induced cytotoxic lymphocytes.

The timing and dosing of the IFN-α-2b and IL-2, as defined in study CTL-03, likely primes the melanoma cells for lysis by upregulating key tumor markers (class I and melanoma-associated antigen expression) and results in antigen-specific T cell persistence. This conclusion is supported by the observations that the: 1) presence of tetrameric-positive cells detected at the start of each successive cell therapy treatment were detected; 2) growth curves resembling secondary or memory responses were observed; and 3) interferon gamma was produced in culture supernatants evaluated at day 6 of the ex vivo protocol for each cycle of cell therapy. Advances in the understanding of the cellular and molecular biology of IL-2 and its receptor complex have provided rationale to better utilize IL-2 to expand and activate immune effectors in patients with cancer. The ex vivo protocol described herein to generate antigen-specific T cells results in a bulk CD8+ preparation that has all of the necessary surface molecules to traffic to the tumor site, recognize and lyse the tumor cells expressing the melanoma-associated antigens, with exquisite selectivity. The presence of the high affinity IL-2 receptor (CD25/CD122/CD132) on the surface of the CD8+ cells suggests that these cells are capable of responding to lower doses of IL-2 in vivo.

The combination of the cytokine therapy in conjunction with the added T cell therapy, represents a novel way to treat advanced, metastatic melanoma.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed:

1. A method for producing activated CD8+ T cells specific to one or more melanoma antigens for administration to a subject, comprising:
   a. harvesting CD8+ T cells and CD8-depeleted mononuclear cells from the subject;
   b. culturing said CD8+ T cells with a non-naturally occurring antigen-presenting cell line (nnAPC) presenting one or more melanoma antigenic peptides for a period of time sufficient for activation of CD8+ T cells that are specific for the melanoma antigenic peptides, wherein the melanoma antigenic peptides have the amino acid sequences of peptide fragments of one or more melanoma-associated antigens; wherein at least one of the melanoma-associated antigens is selected from the group consisting of tyrosinase, gp100, and MART-1, and wherein said melanoma antigenic peptides are each about six to twelve amino acids in length;
   c. adding said CD8+ T cells to media that contains at least one cytokine selected from the group consisting of IL-2, IL-7 or conditioned growth medium (CGM), wherein said cytokines can be used individually or in combination to expand the CD8+ T cells;
   d. irradiating said CD8-depeleted mononuclear cells with a sufficient dose of γ-radiation to prevent proliferation of said CD8-depeleted mononuclear cells;
   e. isolating adherent CD8-depeleted mononuclear cells from the irradiated cells;
   f. loading the CD8-depleted mononuclear cells with about 1 to 50 µg/ml of the melanoma antigenic peptides;
   g. restimulating said CD8+ T cells by mixing said CD8+ T cells with the peptide-loaded CD8-depleted mononuclear cells at a ratio of about ten CD8+ T cells to one CD8-depleted mononuclear cells;
   h. expanding the CD8+ T cells; and
   i. inoculating the subject with collecting the activated CD8+ T cells specific to melanoma antigenic peptides for administration to the subject.

2. The method of claim 1 wherein said nnAPC is capable of simultaneously presenting up to about ten different melanoma antigenic peptides.

3. The method of claim 1 wherein said melanoma antigenic peptides are about eight to ten amino acids in length.

4. The method of claim 1 wherein said melanoma antigenic peptides presented by said nnAPC are in a concentration range of about 10 nM to 100 µM.

5. The method of claim 1 wherein said media contains IL-2.

6. The method of claim 1 wherein said media contains IL-2 and IL-7.

7. The method of claim 1 wherein the dose of γ-radiation is 3,000 to 7,000 rads.

8. The method of claim 1 wherein the dose of γ-radiation is about 5,000 rads.

* * * * *

SEQUENCE LISTING

```
<160> NUMBER OF SEQ ID NOS: 43

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 1

Tyr Met Asn Gly Thr Met Ser Gln Val
1               5
```

```
<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 2

Tyr Met Asp Gly Thr Met Ser Gln Val
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 3

Phe Leu Pro Trp His Arg Leu Phe Leu Leu
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 4

Ile Thr Asp Gln Val Pro Phe Ser Val
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 5

Lys Thr Trp Gly Gln Tyr Trp Gln Val
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 6

Ala Ala Gly Ile Gly Ile Leu Thr Val
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 7
```

Cys Leu Thr Ser Thr Val Gln Leu Val
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 8

Lys Ile Phe Gly Ser Leu Ala Phe Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 9

Lys Met Ala Ser Arg Ser Met Arg Leu
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 10

Ala Leu Ala Leu Ala Ala Leu Leu Val Val
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 11

Ala Leu Leu Val Val Asp Arg Glu Val
1               5

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 12

Ala Ala Glu Gly Leu Asp Thr Gln Arg Phe Ser Gly
1               5                   10

<210> SEQ ID NO 13
<211> LENGTH: 9
<212> TYPE: PRT
<213> ORGANISM: Artificial Sequence

```
<220> FEATURE:
<223> OTHER INFORMATION: Description of Artificial Sequence: Synthetic
      construct

<400> SEQUENCE: 13

His Leu Tyr Gln Gly Cys Gln Val Val
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 14

Ile Ile Ser Ala Val Val Gly Ile Leu
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 15

Pro Leu Thr Ser Ile Ile Ser Ala Val
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 16

Val Met Ala Gly Val Gly Ser Pro Tyr Val
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 17

Val Leu Val Lys Ser Pro Asn His Val
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 18

Glu Leu Val Ser Glu Phe Ser Arg Met
1               5
```

-continued

```
<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 19

Gly Pro Leu Thr Pro Leu Pro Val
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 20

Ser Thr Ala Pro Val His Asn Val
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 21

Tyr Leu Ser Gly Ala Asn Leu Asn Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 22

Glu Ile Trp Thr His Ser Tyr Lys Val
1               5

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 23

Ser Ile Leu Ser Leu Lys Glu Ala Ser Thr
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
```

```
<400> SEQUENCE: 24

Ser Leu Leu Met Trp Ile Thr Gln Cys
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 25

Ser Leu Leu Met Trp Ile Thr Gln Val
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 26

Gln Leu Ser Leu Leu Met Trp Ile Thr
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 27

Tyr Leu Glu Thr Phe Arg Glu Gln Val
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 28

Val Leu Leu Lys Leu Arg Arg Pro Val
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 29

Gly Leu Gln Ser Pro Lys Ser Pro Leu
1               5

<210> SEQ ID NO 30
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      construct

<400> SEQUENCE: 30

Glu Leu Tyr Ile Pro Ser Val Asp Leu
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 31

Lys Ala Leu Phe Ala Gly Pro Pro Val
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 32

Phe Met Trp Gly Asn Leu Thr Leu Ala
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 33

Phe Leu Trp Gly Pro Arg Ala Leu Val
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 34

Ile Leu Ala Lys Phe Leu His Trp Leu
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 35

Arg Leu Val Asp Asp Phe Leu Leu Val
1               5
```

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 36

His Leu Ser Thr Ala Phe Ala Arg Val
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 37

Ser Ile Ser Gly Asp Leu His Ile Ile
1               5

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 38

Val Ala Ala Ser Val Asp Asn Pro His Val
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 39

Glu Leu Ile Ile Glu Phe Ser Lys Met
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 40

Cys Leu Thr Ser Thr Val Gln Leu Ile
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

```
<400> SEQUENCE: 41

Arg Leu Leu Gln Glu Thr Glu Leu Val
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 42

Arg Leu Leu Gln Glu Arg Glu Leu Val
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 43

Ser Leu Tyr Val Thr Val Ala Thr Leu
1               5
```